United States Patent [19]
Kishi et al.

[11] Patent Number: 5,436,238
[45] Date of Patent: Jul. 25, 1995

[54] HALICHONDRINS AND RELATED COMPOUNDS

[75] Inventors: Yoshito Kishi, Belmont, Mass.;
Francis G. Fang, Durham, N.C.;
Craig J. Forsyth, Roseville, Minn.;
Paul M. Scola, Watertown, Mass.;
Suk K. Yoon, Seoul, Rep. of Korea

[73] Assignee: President and Fellows of Harvard College, Cambridge, Mass.

[21] Appl. No.: 30,893

[22] Filed: Mar. 12, 1993

Related U.S. Application Data

[63] Continuation-in-part of Ser. No. 11,104, Jan. 29, 1993, Pat. No. 5,338,865, which is a continuation of Ser. No. 849,769, Mar. 12, 1992, abandoned.

[51] Int. Cl.⁶ ............................................. C07D 311/78
[52] U.S. Cl. ..................................... 514/214; 549/268
[58] Field of Search ............................... 549/214, 268

[56] References Cited

PUBLICATIONS

Aicher et al., "Synthetic Studies Towards Halichondrins", Tetrahedron Letters, vol. 28, No. 30, 1987, pp. 3463–3466.
Aicher et al., "Synthetic Studies Towards Halichondrin B", Dissertation Abstracts International, vol. 50, No. 12, 1990, p. 5619-B.
Angyal et al., "Complexes of Carbohydrates with Metal Cations. V* Syntheses of Methyl Glycosides in the Presence of Metal Ions", Australian Journal of Chemistry, vol. 28, No. 7, 1975, pp. 1541–1549.
Bai et al., "Halichondrin B and Homohalichondrin B, Marine Natural Products Binding in the Vinca Domain of Tubulin", The Journal of Biological Chemistry, vol. 266, No. 24, 1991, pp. 15882–15889.
Banaszek et al., "Oxyamination of Unsaturated Sugar Derivatives. Part II*. Synthesis of Alkyl 2-Deoxy- and 2,6-Dideoxy-2-p-Toluenesulfonamido- and 3-deoxy- and 3,6-dideoxy-3-p-Toluenesulfonamido-α-D-Manno- and Talo-Hexo-Pyranosides", Polish Journal of Chemistry, vol. 53, 1979, pp. 2029–2039.
Brimacombe et al., "A Synthesis of 2-O-Methyl-L-Lyxose, a Component of Everninomicins B and D", Journal of the Chemical Society, 1971, pp. 2911–2915.
Brimacombe et al., "The Oxidation of Some Carbohydrate Derivatives, Using Acid Anhydride-Methyl Sulphoxide Mixtures and the Pfitzner-Moffatt Reagent. Facile Synthesis of 3-Acetamido-3-Deoxy-D-Glucose and 3-Amino-3-Deoxy-D-Xylose", Carbohydrate Research, vol. 3, 1967, pp. 318–324.
Burke et al., "Synthesis of a C922)→C(34) Halichondrin Precursor via a Double Dioxanone-to-Dihydropyran Rearrangement", Tetrahedron Letters, vol. 32, No. 32, 1991, pp. 3961–3964.
Cannizzo et al., "In Situ Preparation of (μ-Chloro)(-μ-methylene)bis(cyclopentadienyl)(dimethylaluminum) Titanium (Tebbe's Reagent)", J. Org. Chem., vol. 50, 1985, pp. 2386–2387.
Carpita et al., "Stereocontrolled Synthesis of Naturally-Occurring Polyacetylenes Characterized By (E)-1-EN-3-YNE, (E)-1-EN-3,5-Diyne, (1E,5E)-1,-5-Dien-3-YNE, and (1E,7E)-1,7-Dien-3,5-Diyne Moieties(*)", Gazzetta Chimica Italiana, 117, 1987, pp. 481–489.
Colvin et al., "One-step Conversion of Carbonyl Compounds into Acetylenes", Journal of The Chemical Society, 5, 1973, pp. 151–152.
Colvin et al., "A Simple Procedure for the Elaboration of Carbonyl Compounds into Homologous Alkynes", Journal of The Chemical Society, 8, 1977, pp. 869–874.
Commercon et al., "Substitution Des Halogeno-1 Alcynes-1 Par Les Derives Organometalliques Du (List continued on next page.)

*Primary Examiner*—Johann Richter
*Assistant Examiner*—John Peabody
*Attorney, Agent, or Firm*—Fish & Richardson

[57] ABSTRACT

Novel chemical compounds that can be used to synthesize halichondrin B and norhalichondrin B, and related derivatives. The total synthesis of halichondrin B and norhalichondrin B is also disclosed.

11 Claims, 3 Drawing Sheets

PUBLICATIONS

Cuivre. Access A Une Nouvelle Classe de Synthons: Application a la synthese du Bombykol", Tetrahedron, vol. 36, No. 9, 1980, pp. 1215–1221.

Cooper et al., "Total Synthesis of Halichondrins: Enantioselective Construction of a Homochiral Pentacyclic C1–C15 Intermediate from D–Ribose", Tetrahedron Letters, vol. 31, No. 27, 1990, pp. 3813–3816.

Drouin et al., "Regiocontrolled Cyclisation of Acetylenic Ketones. First Example of Selective Desilylation of a Triple Bond in Presence of a Silyl Enol Ether", Tetrahedron Letters, vol. 28, No. 34, 1987, pp. 3923–3926.

Evans et al., "Monomolar Acetalations of Methyl Methyl α–D–Mannosides–Synthesis of Methyl α–D–Talopyranoside", Carbohydrate Research, vol. 54, No. 1., 1977, pp. 105–114.

Gilbert et al., "Elaboration of Aldehydes and Ketones to Alkynes: Improved Methodology," Journal of Organic Chemistry, vol. 44, No. 26, 1979, pp. 4997–4998.

Gorin, P. A. J. et al., "Hydrogenolysis of Carbohydrates: VIII. Comparative Studies on Methyl Glycopyranosides", Can. J. Chem., vol. 38, 1960, pp. 641–651.

Hirata, Yoshimasa et al., "Halichondrins–antitumor polyether macrolides from a marine sponge," Pure & Appl. Chem., vol. 58, No. 5, 1986, pp. 701–709.

Horton, Derek et al., "Selective silylation of 6–deoxyglycals", Carbohydrate Research, vol. 144, 1985, pp. 325–330.

Inanaga, Junji et al., "A Rapid Esterification by Means of Mixed Anhydride and Its Application to Large–ring Lactonization," Bulletin of The Chemical Society of Japan, vol. 52 (7), 1979, pp. 1989–1993.

Ireland, Robert E. et al., "3–Acyltetramic Acid Antibiotics. 2. Synthesis of (+)–Streptolic Acid", J. Am. Chem. Soc., vol. 110, 1988, pp. 854–860.

Ireland, Robert E. et al., "The Ester Enolate Claisen Rearrangement. Stereochemical Control through Stereoselective Enolate Formation," Journal of the American Chemical Society, May 12, 1976, pp. 2868–2877.

Ireland, Robert E. et al., "3–Acyltetramic Acid Antibiotics. 1. Synthesis of Tirandamycic Acid", Journal of the American Chemical Society, vol. 103, 1981, pp. 3205–3207.

Jin, Haolun et al., "Catalytic Effect of Nickel(II) Chloride and Palladium(II) Acetate on Chromium–(II)–Mediated Coupling Reaction of Iodo Olefins with Aldehydes", J. Am. Chem. Soc., vol. 108, 1986, pp. 5644–5646.

Jirousek, Michael Robert, Ph.D., "Part I. Halichondrin B: Studies on the total synthesis. Part II. Levuglandins: Generation from $PGH_2$ and binding with proteins", Dissertation Abstracts International, vol. 51, No. 2, Aug., 1990, pp. 751B–752B.

Katsuki et al., "The First Practical Method of Asymmetric Epoxidation", J. Am. Chem. Soc., 102, 1980, 5974–5976.

Kim, Seokchan et al., "Total Synthesis of Halichondrins: Highly Stereoselective Construction of a Homochiral Pentasubstituted H–ring Pyran Intermediate from α–D–Glucose", Tetrahdron Letters, vol. 30, No. 46, 1989, pp. 6279–6282.

Kinzy, Willy et al., "Direct 3,6–Di–O–Protection of Glucal and Galactal", Tetrahedron Letters, vol. 28, No. 18, 1987, pp. 1981–1984.

Kishi, Yoshito "Applications of Ni(II)/Cr(II)–mediated coupling reactions to natural products syntheses", Pure & Appl. Chem., vol. 64, No. 3, 1992, pp. 343–349.

Kishi, "Recent Developments in the Chemistry of Natural Products", Aldrichimica Acta, vol. 13, No. 2, 1980, pp. 23–30.

Kozikowski, Alan P. et al., "A Synthetic Approach to the Cis–Fused Marine Pyranopyrans, (3E)–and (3Z)––Dactomelyne, X–ray Structure of a Rare Organomercurial", J. Org. Chem., vol. 55, 1990, pp. 863–870.

Lewis et al., "Highly Stereoselective Approaches to α– and β–C–Glycopyranosides", J. Am. Chem. Soc. 104, 1982, pp. 4976–4978.

Mahoney, Wayne S. et al., "Selective Hydride–Mediated Conjugate Recution of α,β–Unsaturated Carbonyl Compounds Using $[Ph_3P)CuH]_6$", J. Am. Chem. Soc., vol. 110, 1988, pp. 291–293.

Mahoney, Wayne S. et al., "Hydride–Mediated Homogeneous Catalysis. Catalytic Reduction of α,β–Unsaturated Keytones Using $[Ph_3P)CuH]_6$", J. Am. Chem. Soc., vol. 111, 1989, pp. 8818–8823.

Mancuso et al., "Oxidation of Long–Chain and Related Alcohols to Carbonyls by Dimethyl Sulfoxide 'Activated' by Oxalyl Chloride", J. Org. Chem., vol. 43, No. 12, 1978, pp. 2480–2482.

(List continued on next page.)

PUBLICATIONS

Mitsunobo, Dyo, "The Use of Diethyl Azodicarboxylate and Triphenylphosphine in Synthesis and Transformation of Natural Products", Int'l. Journal of Methods in Synthetic Organic Chemistry, vol. 1/Jan., 1981, pp. 1-28.

Nakata et al., "Synthetic Studies of Rifamycins. II. Syntheses of Methyl 2,4,6,7-Tetra-deoxy-4-C-methyl-3-O-methyl-α-L-arabino-heptopyranosid-6-ulose and Its Derivatives Utilizable in the Construction of the Rifamycin Ansa Chain Portion", Bull. Chem. Soc. Jpn., 53, 1980, pp. 3252-3258.

Oikawa, Yuji et al., "Specific Removal of o-Methoxybenzyl Protection by DDQ Oxidation", Tetrahdron Letters, vol. 23, No. 8, 1982, pp. 885-888.

Oikawa, Yuji et al., "Protection of Hydroxy Groups By Intramolecular Oxidative Formation of Methoxybenzylidene Acetals with DDQ", Tetrahdron, vol. 23, No. 8, 1982, pp. 889-892.

Omura et al., "Oxidation of Alchols by 'Activated' Dimethyl sulfoxide. A Preparative Steric and Mechanistic Study", Tetrahedron, vol. 34, 1978, pp. 1651-1660.

Panek et al., "Oxygenated Allylic Silanes: Useful Homoenolate Equivalents for the Stereoselective C—Glycosidation of Pyranoside Derivative", J. Org. Chem. vol. 54, No. 9, 1989, pp. 2034-2038.

Sharpless et al. "High Stereo- and Regioselectivities in the Transition Metal Catalyzed Epoxidations of Olefinic Alcohols by tert-Butyl Hydroperoxide", J. Am. Chem. Soc., vol. 95, No., 1973, pp. 6136-6137.

Sharpless et al. "Olefin Synthesis. Rate Enhancement of the Elimination of Alkyl Aryl Selenoxides by Electron-Withdrawing Substituents", J. Org. Chem., vol. 40, No. 7, 1975, pp. 947-949.

Sharpless et al. "Metal-Catalyzed, Highly Selective Oxygenations of Olefins and Acetylenes with tert-Butyl Hydroperoxide, Practical Considerations and Mechanisms", Aldrichimica Acta, 12, 1979, pp. 63-74.

Sowden, "α-L-Glucose and L-Mannose", Methods in Carboyhydrate Chemistry, vol. 1, 1962, pp. 132-135.

Still et al., "Direct Synthesis of Z-Unsaturated Esters. A Useful Modification of the Horner-Emmons Olefination", Tetrahedron, vol. 24, No. 41, 1983, pp. 4405-4408.

Takai et al., "Reactions of Alkenylchromium Reagents Prepared from Alkenyl Trifluoromethanesulfonates (Triflates) with Chromium(II) Chloride under Nickel Catalysis," J. Am. Chem. Soc., 108, 1986, pp. 6048-6050.

Tanaka et al., "Stereoselective Epoxidations of Acyclic Allylic Alchols by Transition Metal-Hydroperoxide Reagents. Synthesis of dl-C18 Cecropia Juvenile Hormone from Farnesol", J. Am. Chem. Soc., vol. 96, No. 14, 1974, pp. 5254-5255.

Tebbe, F. N. et al., "Olefin Homologation with Titanium Methylene Compounds", Am. Chem. Society, vol. 100, No. 11, May 24, 1978, pp. 3611-3613.

Theander, Olof, "1,2:5,6-Di-O-isopropylidene Derivatives of D-Glucohexodialdose and D-Ribo-hexos-3-ulose", Acta Chem. Scand. vol. 18, No. 10, 1964, pp. 2209-2116.

Tomooka, Katsuhiko et al., "Lactols in Stereoselection 3. Highly anti-Cram Selective 1,2-Asymmetric Induction", Tetrahedron Letters, vol. 30, No. 12, 1989, pp. 1563-1566.

Uemura, Daisuke et al., "Norhalichondrin A: An Antitumor Polyether Macrolide from a Marine Sponge," J. Am. Chem. Soc., vol. 107, 1985, pp. 4796-4798.

VanRheenen et al., "An Improved Catalytic OsO4 Oxidation of Olefins to CIS-1,2-Glycols Using Tertiary Amine Oxides as the Oxidant", Tetrahedron, No. 23, 1976, pp. 1973-1976.

Vekemans et al., "Vitamin C and Isovitamin C Derived Chemistry. 3. Chiral Butenolides via Efficient 2,3-Didehydroxylations of L-Gulono-, D-Mannono-, and D-Ribono-1,4-lactones", J. Org. Chem. 53, 1988, pp. 627-633.

Wong, Margaret Y. H. et al., "2-Deoxypentoses Stereoselective Reduction of Ketene Dithioacetals," J. Am. Chem. Soc., vol. 100, No. 11, 1978, pp. 3548-3553.

Yamaguchi et al., "An Efficient Method for the Alkynylation of Oxiranes Using Alkynyl Boranes", Tetrahedron, vol. 24, No. 4, 1983, pp. 391-394.

HALICHONDRINS AND RELATED COMPOUNDS

STATEMENT AS TO FEDERALLY SPONSORED RESEARCH

This invention was made with support from the National Institutes of Health, National Cancer Institute (Grant No. 5 R37 CA22215). Accordingly, the U.S. government has certain rights in the invention.

CROSS REFERENCE TO RELATED APPLICATION

This application is a continuation-in-part of U.S. patent application Ser. No. 08/011,104, filed Jan. 29, 1993 now U.S. Pat. No. 5,338,865, which, in turn, is a continuation of U.S. patent application Ser. No. 07/849,769, filed Mar. 12, 1992, now abandoned.

BACKGROUND OF THE INVENTION

The invention relates to halichondrins and compounds related thereto, such as synthetic intermediates of halichondrins and derivatives of such intermediates.

Halichondrins are a class of polyether macrolides isolated originally from the marine sponge *Halichondria okadai* Kadota. Examples of halichondrins include halichondrin B, homohalichondrin B and homohalichondrin B, the structures of which have all been elucidated. Halichondrins exhibit an extraordinary in vitro and in vivo antitumor activity. However, the very limited supply of halichondrins from natural sources has prevented the full evaluation of their potential clinical applications.

SUMMARY OF THE INVENTION

One aspect of the present invention relates to novel compounds that can be used to synthesize halichondrin B and norhalichondrin B, as well as derivatives of these novel compounds.

One class of compounds of this invention has the following formula:

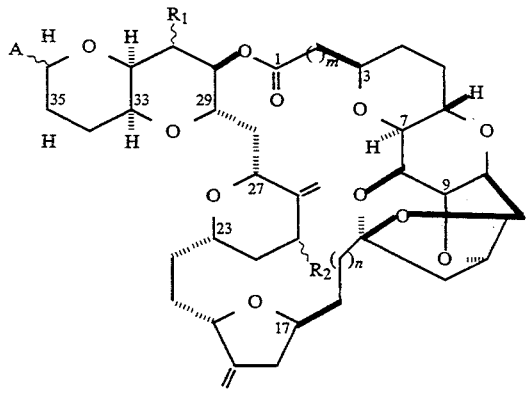

in which each of $R_1$ and $R_2$ is H— or $C_{1-10}$ alkyl, alkenyl or alkynyl (preferably, $C_{1-6}$ alkyl, e.g., methyl); and each of A and B is H—, HO— with or without an alcohol protecting group, an unsubstituted hydrocarbon, or a substituted hydrocarbon with or without an alcohol protecting group; wherein the total carbon number of A and B ranges from 0–18 (not counting the carbons in any alcohol protecting groups, if present); and each of m and n is 0–3 (preferably, 1). When both A and B are substituted or unsubstituted hydrocarbons, they may be joined together at one or more points.

Note that a line between two atoms in the structural formulas disclosed herein indicates a single bond unless otherwise stated.

The term "substituted hydrocarbon" or "substituted alkyl" refers to a hydrocarbon or an alkyl which contains a functional group, selected from the group consisting of ether, halogen, keto, aldehyde, ester, amino, and alcohol (—OH). When the functional group is —OH, it can be protected by an alcohol protecting group. Alcohol protecting groups include, but are not limited to, $R_5$—O—, $R_5$—CO—O—, $R_5$—O—CO—O—, or

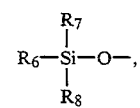

in which $R_5$ is $C_{1-10}$ alkyl, $C_{2-10}$ alkenyl, $C_{2-10}$ alkynyl, $C_{7-20}$ aralkyl, $C_{7-20}$ alkaryl, phenyl or tetrahydropyranyl, and each of $R_6$, $R_7$ and $R_8$ is $C_{1-6}$ alkyl, $C_{2-6}$ alkenyl or phenyl. Note that the oxygen at the right end of the above listed alcohol protecting groups refers to the same oxygen in an —OH which is intended to be protected.

Below are four examples of alcohol protecting groups:

p-methoxyphenylmethyl (MePhCH$_2$O— or "MPM"),

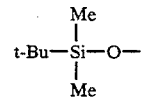

(t-butyldimethylsilyl or "TBS"), pivaloyl ("Pv") and CH$_2$=C—CH$_2$—O—CO—O—.

It is preferred that each of A and B in the above formula be HO—, HO— linked to an alcohol protecting group, or a substituted hydrocarbon selected from the group consisting of $R_3$—CO—$R_4$—, $R_3$—CH(OH)—$R_4$—, $R_3$—CH(OH)—$R_4$— linked to an alcohol protecting group, $R_3$—O—CO—, $R_3$—O—CO—$R_4$—, HO—$R_4$—, and HO—$R_4$— linked to an alcohol protecting group; each of $R_3$ (conovalent) and $R_4$ (divalent) is alkyl, alkenyl or alkynyl. It is also preferred that the total carbon number of A and B range from 0–15 or 0–12 (not counting the carbons in any alcohol protecting groups, if present) and each of m and n is 0–2.

In some preferred compounds of this class, each of A and B is HO—, HO— linked to an alcohol protecting group, HO—$R_4$—, or HO—$R_4$— linked to an alcohol protecting group. It is particularly preferred that A is HO—$R_4$— or HO—$R_4$— linked to an alcohol protecting group and B is HO— or HO— linked to an alcohol protecting group.

The compound of claim 1, wherein the respective stereo-chemistries of C.25, C.31, C.35 and C.36 are either R, S, R and R, or S, R, S and S.

A method of administering a therapeutically effective amount of one or more of the above-described compounds to inhibit the growth of tumor (e.g., melanoma, fibrosarcoma, monocytic leukemia, colon carcinoma, ovarian carcinoma, breast carcinoma, osteosarcoma or rastransforming fibroblast) in a mammal is also within the scope of this invention.

Another class of compounds of this invention has the following formula:

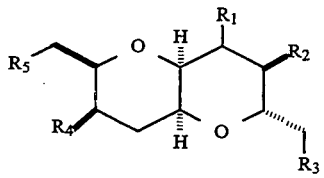

in which $R_1$ is H or $C_{1-10}$ alkyl (e.g., methyl), each of $R_2$ and $R_4$ is —OH or a protected —OH; $R_3$ is

—$CH_2$—B, —CO—O—D or —CH—O; and $R_5$ is —CHO, —$CH_2$—B or —CO—O—D; where B is —OH or a protected —OH, D being —H or $C_{1-10}$ alkyl and E is $C_{1-30}$ or $C_{1-10}$ substituted or unsubstituted alkyl. As examples, $R_2$ can be —OMPM, $R_4$ can be —OTBS and $R_5$ can be —$CH_2$—OTBS (i.e., —$CH_2$—B where B is —OTBS). $R_4$ is TBSO— and $R_5$ is TBSO—$CH_2$—.

In one example of this class of compound, $R_3$ is of the following formula:

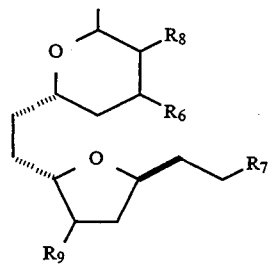

in which $R_6$ is —H or $C_{1-10}$ alkyl (e.g., methyl ); $R_7$ is —CHO, —$CH_2$—B, or —CO—O—D; and each of $R_8$ and $R_9$ is —H, methylidene (i.e., =$CH_2$), $C_{1-5}$ alkyl (e.g., methyl) or $C_{2-5}$ alkenyl. Preferably, $R_1$ is methyl and $R_5$ is $CH_2$—B. It is apparent that the line between $R_5$ (or $R_9$) and the carbon on the ring to which it is linked can be either a single bond (when $R_8/R_9$ is H) or a double bond (when $R_8/R_9$ is =$CH_2$).

Another example of this class of compounds is of the following formula:

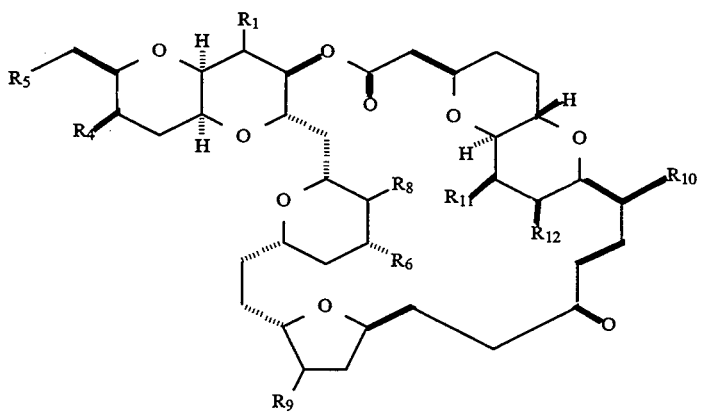

in which each of $R_{10}$, $R_{11}$ and $R_{12}$ is —OH of a protected —OH. Preferably, each of $R_1$ and $R_6$ is methyl, $R_4$ is a protected —OH, $R_5$ is —$CH_2$—B, and each of $R_8$ and $R_9$ is methyl or methylidene. It is particularly preferred that $R_4$ is TBSO— and $R_5$ is TBSO—$CH_2$—.

A further example of this class of compounds has the following formula:

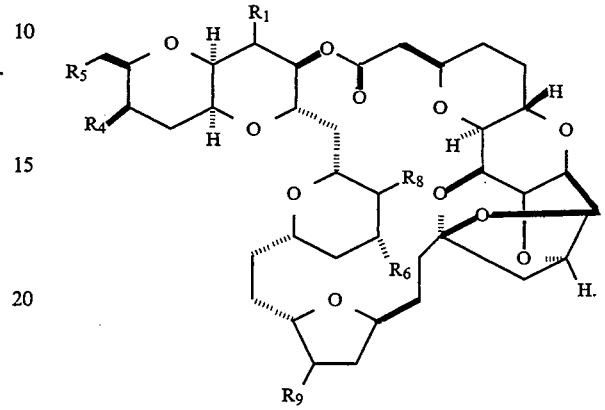

In the compound of the above formula, it is preferred that each of $R_1$ and $R_6$ is methyl, $R_4$ is a protected —OH (e.g., TBSO—), $R_5$ is —$CH_2$—B (e.g., TBSO—$CH_2$—), and each of $R_8$ and $R_9$ is methyl or methylidene.

Yet another class of compounds of this invention has the following structure:

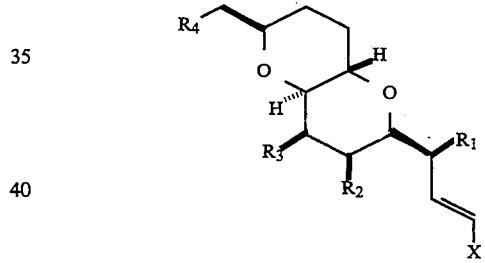

in which X is a halogen (e.g., —I or —Br) or an activated alcohol (e.g., —$OSO_2CF_3$); each of $R_1$, $R_2$ and $R_3$ is —OH or a protected —OH; and $R_4$ is —CHO, —$CH_2$—B, or —CO—O—D; where B is —OH or a protected —OH and D is —H or $C_{1-10}$ alkyl. Preferably, each of $R_1$, $R_2$ and $R_3$ is —OTBS, and $R_4$ is —CO—$OCH_3$.

Still another class of compounds of this invention has the following structure:

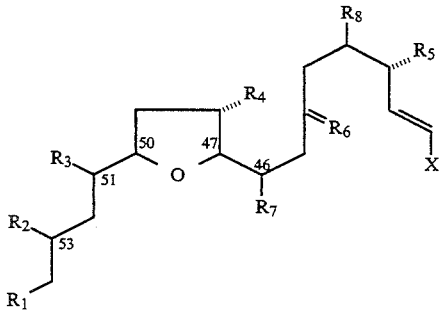

in which each of $R_1$, $R_2$, $R_3$, $R_4$ and $R_5$ is —OH or a protected —OH; $R_6$ is O or a protected ketone; each of $R_7$ and $R_8$ is —H, $C_{1-5}$ alkyl or $C_{2-5}$ alkenyl; and X is a halogen (—I or —Br) or an activated alcohol (e.g., —OSO$_2$CF$_3$). Examples of a suitable protected ketone in this invention include, but are not limited to, >C(OCH$_3$)$_2$ and >C(SCH$_3$) The carbon at the left end is the carbon of the ketone (i.e., >C=O) which is intended to be protected. In a preferred compound, each of $R_1$, $R_2$, $R_3$ and $R_4$ is TBSO—; $R_5$ is —OMPM; $R_6$ is O; each of $R_7$ and $R_8$ is methyl; and X is I. Preferably, the stereochemistries of C.46, C.47, C.50, C.51, and C.53 are S, S, S, S and R, respectively.

Still another class of compounds of this invention has the following structure:

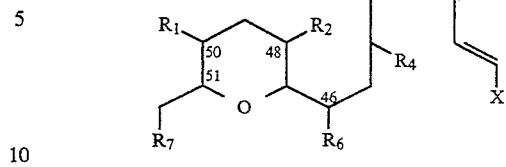

in which each of $R_1$, $R_2$ and $R_3$ is —OH or a protected —OH; $R_4$ is O or a protected ketone; each $R_5$ and $R_6$ is —H or $C_{1-5}$ alkyl; $R_7$ is —CH$_2$—B, —CHO or —CO—O—D; and X is a halogen or an activated alcohol; where B is —OH or a protected —OH and D is —H or $C_{1-10}$ alkyl. Preferably, the stereochemistries of C.42, C.48 and C.50 are S, S and R, respectively. In a particularly preferred compound, each of $R_1$ and $R_2$ is TBSO—; $R_3$ is —OMPM; $R_4$ is O; each $R_5$ and $R_6$ is methyl; $R_7$ is —CO—OCH$_3$; X is I; and the stereochemistries of C.46 and C.51 are S and R, respectively.

Another class of compounds of this invention has the following structure:

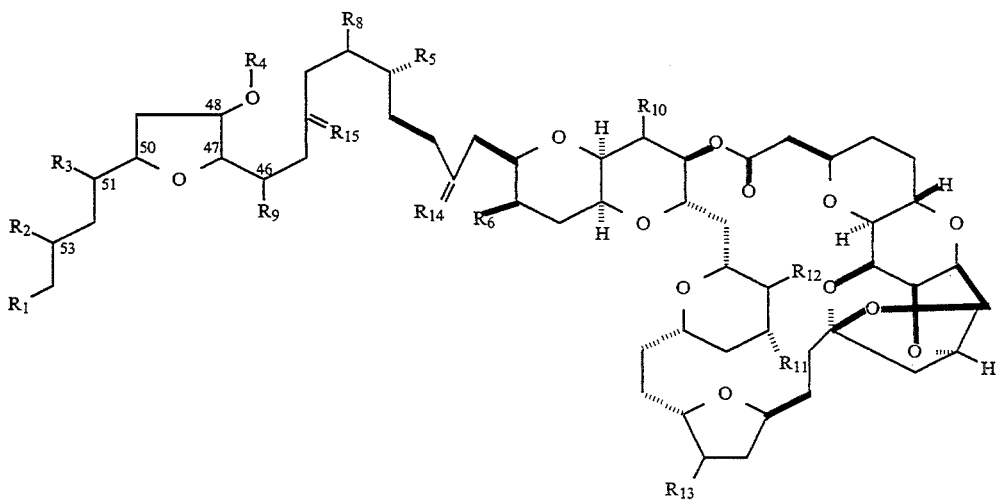

in which each of $R_1$, $R_2$, $R_3$, $R_4$, $R_5$ and $R_6$ is —OH or a protected —OH; each of $R_8$, $R_9$, $R_{10}$ and $R_{11}$ is —H, $C_{1-5}$alkyl or $C_{2-5}$ alkenyl; each of $R_{12}$ and $R_{13}$ is methyl or methylidene; and each of $R_{14}$ and $R_{15}$ is O or a protected ketone. Preferably, the stereochemistries of C.42, C.46, C.47, C.48, C.50, C.51 and C.53 are S, S, S, S, S, S and R, respectively. In a particularly preferred compound, each of $R_1$, $R_2$, $R_3$, $R_4$ and $R_6$ is TBSO—; $R_5$ is —OMPM; $R_7$ is O or a protected ketone; each of $R_8$, $R_9$, $R_{10}$ and $R_{11}$ is —H or $C_{1-5}$ alkyl; and each of $R_{12}$ and $R_{13}$ is methyl or methylidene.

Compounds covered by the following formula are also within the present invention:

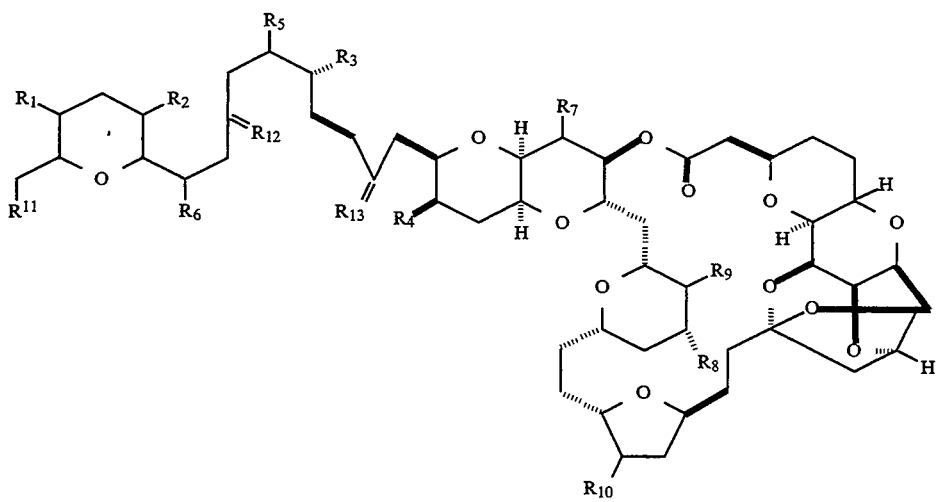

in which each of $R_1$, $R_2$, $R_3$ and $R_4$ is —OH or a protected —OH; each of $R_5$, $R_6$, $R_7$ and $R_8$ is —H, $C_{1-5}$ alkyl or $C_{2-5}$ alkenyl; each of $R_9$ and $R_{10}$ is methyl or methylidene; $R_{11}$ is —CHO, —$CH_2$—B or —CO—O—D; and each $R_{12}$ and $R_{13}$ is O or a protected ketone; where B is —OH or a protected —OH and D is —H or $C_{1-10}$ alkyl. Preferably, the stereochemistries of C.42, C.48 and C.50 are S, S and R, respectively. In a particularly preferred compound, each of $R_1$, $R_2$ and $R_4$ is TBSO—; $R_3$ is —OMPM; each of $R_5$, $R_6$, $R_7$ and $R_8$ is methyl; each of $R_9$ and $R_{10}$ is methylidene; and $R_{11}$ is —CO—$OCH_3$.

The invention also features methods of synthesizing the novel compounds and using the compounds in chemical synthesis. One particularly preferred method is the coupling of an aldehyde to a vinyl halide using Ni(II)/Cr(II) mediated reaction conditions. This technique results in the straightforward formation of a carbon-carbon bond between chemically unstable species. As will be shown below, for synthesis of halichondrin B and norhalichondrin B, the Ni(II)/Cr(II) mediated reaction can be used to form carbon-carbon bonds between $C_{11}$ and $C_{12}$, $C_{13}$ and $C_{14}$, $C_{26}$ and $C_{27}$, $C_{29}$ and $C_{30}$, and $C_{38}$ and $C_{39}$, with good yields.

The compounds and methods of the invention provide an approach to synthesizing halichondrins in relatively good yields. Sufficient quantities of the final materials can now be obtained so that the full spectrum of their biological activities can be studied. The approach allows the novel compounds to be isolated in pure form.

Other features and advantages of the present invention will be apparent from the following drawings and description of the preferred embodiments, and also from the appending claims.

BRIEF DESCRIPTION OF THE DRAWINGS

The drawings are first described.

DESCRIPTION OF THE PREFERRED EMBODIMENTS

Figure 1:
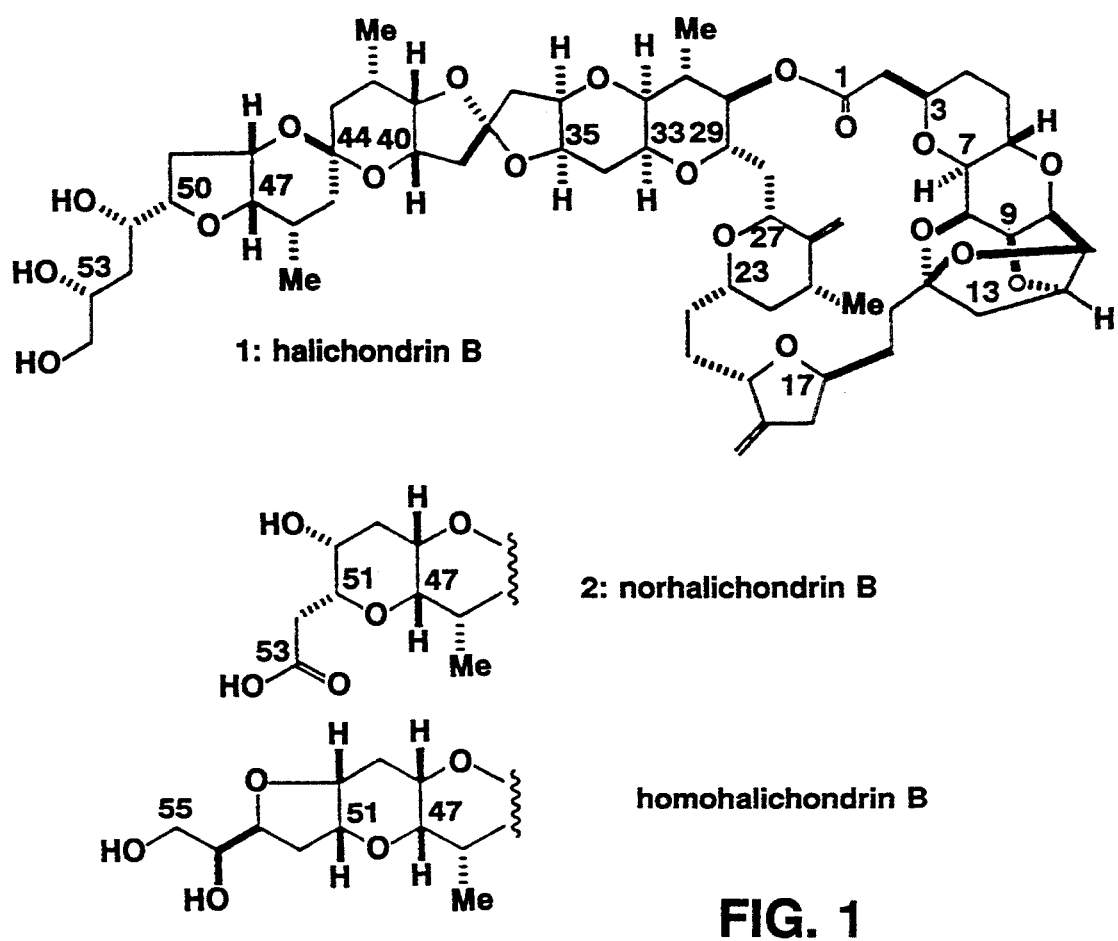
FIG. 1 shows the structures of halichondrin B, norhalichondrin B and homohalichondrin B.

Compounds of the present invention can be used to synthesize halichondrin B 1 and norhalichondrin B 2 (for structures, see FIG. 1).

Schemes 1 and 2, in combination, illustrate the general approach used to synthesize these two compounds. Persons skilled in the art will recognize that the preferred compounds can be modified, e.g., by using different conventional alcohol blocking groups, and still use the same general scheme to synthesize compounds 1 and 2. They also will recognize that the starting compounds can be modified slightly (e.g., by substituting an ethyl for a methyl group) in order to synthesize analogues of compounds 1 and 2.

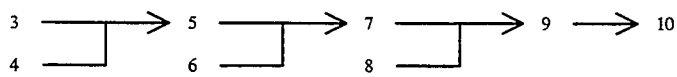

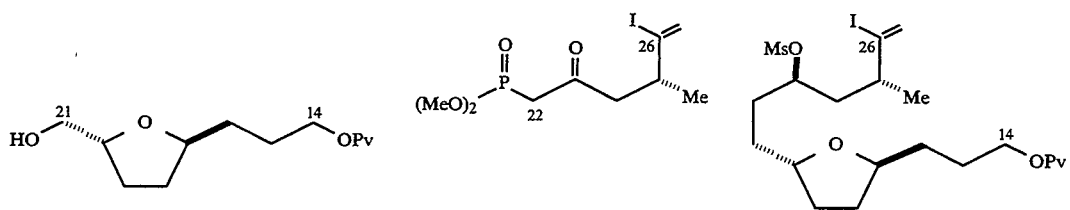

-continued
Scheme 1
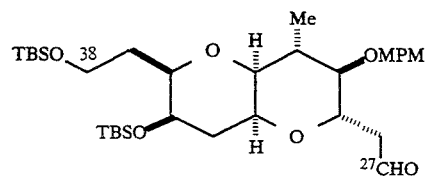
6 ($\alpha_D$ −35.9°)
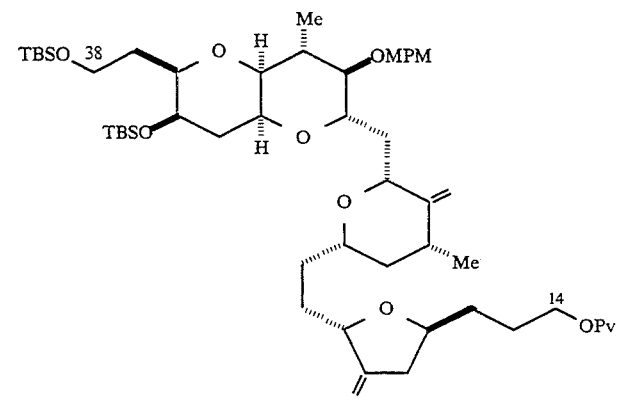
7 ($\alpha_D$ −20.0°)
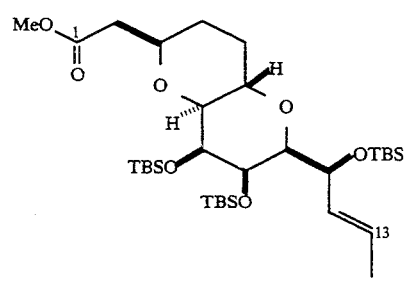
8 ($\alpha_D$ −50.1°)
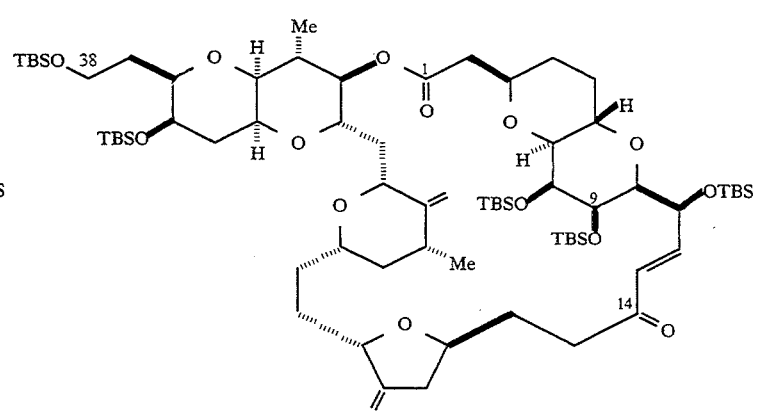
9 ($\alpha_D$ −35.9°)
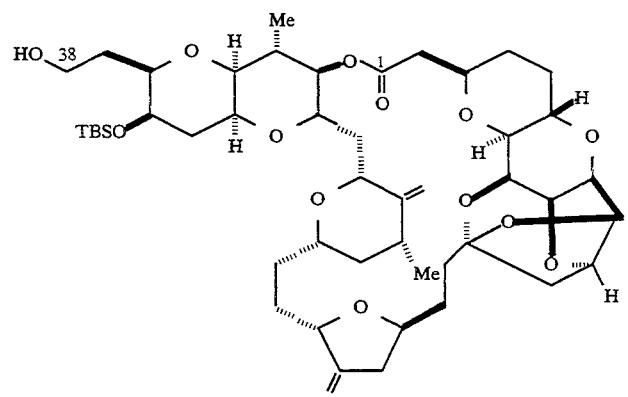
10 ($\alpha_D$ −46.4°)

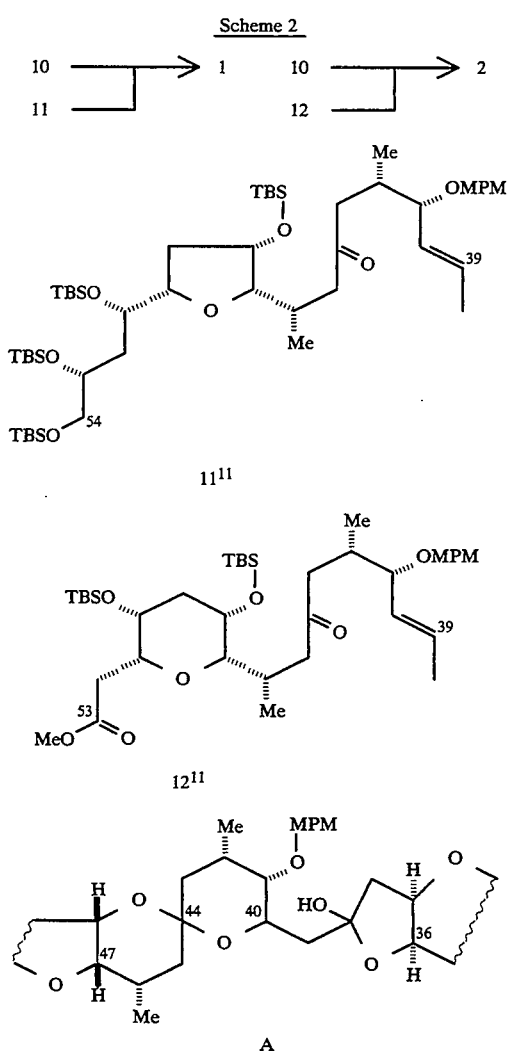

Scheme 1 outlines the synthesis of the right half of the halichondrin B series (i.e., halichondrin B, norhalichondrin B and homohalichondrin B). The C.21–C.22 bond (the bond between carbons at positions 21 and 22) can be accomplished via the preparation of the aldehyde from primary alcohol 3 by Dess-Martin oxidation, Horner-Emmons reaction under carefully controlled conditions, and the conjugate reduction of the resulting enone by the Stryker reagent, without double-bond isomerization. Hydride reduction of the resulting saturated ketone yields approximately a 1:1 mixture of the two possible diastereomers. Without establishing the stereochemistry of diastereomeric alcohols, both diastereomers are then transformed separately into the corresponding mesylates and used for the next coupling reaction. However, it is important to note that the two diastereomeric alcohols are readily interconvertible via the Mitsunobu reaction.

Coupling of compound 5 with compound 6 is accomplished by the Ni(II)/Cr(II)-mediated reaction, to yield approximately a 6:1 mixture of the two possible allylic alcohols, which are immediately subjected to base-induced cyclization to furnish the desired tetrahydropyran in 50–60% overall yield, along with a small amount of the undesired diastereomer. The stereochemistry at the C.23 and C.27 positions can be established by NOE experiments. Compound 5, a mesylate, is quite labile, presumably due to the participation of the C.20 ether oxygen with the mesylate group. Yet, compound 5 has been found to survive nicely under the Ni(II)/Cr(II)-coupling conditions.

The Ni(II)/Cr(II)-mediated coupling of the C.14 aldehyde derived from compound 7 with compound S, followed by Dess-Martin oxidation, gives trans-enone in 77% overall yield. After removal of the C.30 p-methoxyphenylmethyl ("MPM") group and hydrolysis of the C.1 methyl ester, this enone is lactonized under Yamaguchi conditions to afford lactone enone 9 in 63% overall yield.

The polycyclic ring system around the C.8–C.14 moiety is, cleanly and effectively, incorporated on treatment of compound 9 with (n-Bu)$_4$NF ("TBAF") then p-TsOH.Py ("PPTS") in 64% yield. The 1H NMR spectrum has shown the product at the TBAF step to be primarily a saturated ketone. The regioselectivity of the Michael reaction is exclusive for the desired five-membered ring-formation, whereas the stereoselectivity is approximately 5–6:1, favoring the desired diastereomer. The undesired Michael adduct, separated from the desired product after PPTS treatment, can be recycled under TBAF conditions. The adjustment of the protecting groups of the polycyclic product furnishes the right half 10 of the halichondrin B series. An alternative synthesis of the polycyclic ring system from compounds 7 and 8 is also set forth below. (See Example 2, under the subheading Compound 10.)

We now refer to Scheme 2. Coupling of the right half 10 of halichondrin B with the left half 11 is effected by Ni(II)/Cr(II)-mediated reaction to give, after Dess-Martin oxidation, the expected trans-enone in 60% overall yield (Scheme 2). The enone is successfully transformed into halichondrin B in 3 steps without isolation of the product(s) at each step. The 1H NMR spectrum has indicated the product of the TBAF step to have the partial structure A. This process involves deprotection of the C.48 t-butyldimethylsilyl ("TBS") group, hemiketal formation between the C.48 hydroxyl group and the C.44 ketone, and Michael addition of the hemiketal hydroxyl group onto the α,β-unsaturated ketone. The 5,5-spiroketal formation is then completed by deprotection of the C.41 MPM group, followed by acid treatment. The C.41 hydroxyl group needs to be protected differently from the others to avoid 5,6-spiroketal formation between the C.41 and C.48 hydroxyl groups and the C.44 ketone. Although this 3-step transformation introduces three new chiral centers, its stereoselectivity is very high. The overall yield of the 3-step transformation is 50–60%, and the synthetic halichondrin B has been confirmed to be identical with natural halichondrin B1 on comparison of spectroscopic (1H NMR, MS, IR, $[\alpha]_D^{21}$) and chromatographic data.

The synthesis of norhalichondrin B 2 is carried out in virtually the same way as for halichondrin B except that hydrolysis of the C.53 methyl ester is required as the very last step of the synthesis. The overall yield of the norhalichondrin B synthesis is comparable with that of halichondrin B. On comparison of spectroscopic (1H NMR, MS, IR, $[\alpha]_D^{21}$) and chromatographic data, the synthetic norhalichondrin B has been proven to be identical with natural norhalichondrin B 2.

The structure of halichondrin B, norhalichondrin B and homohalichondrin B were previously proposed primarily on the basis of three pieces of evidence: (1) comparison of their spectroscopic data with those of norhalichondrin A, the structure of which was unambiguously established by X-ray analysis, (2) biogenetic considerations of the c.50-and-beyond stereochemistry of halichondrin Bs, and (3) the absolute stereochemistry of halichondrin Bs was assumed to be the same as that of norhalichondrin A, which was deduced from the exciton chirality of its C.12,C.13-bis-p-bromobenzoates. The present synthetic work has established unambiguously the relative and absolute stereochemistry of halichondrin B and norhalichondrin B.

The detailed chemical procedures of total synthesis of both halichondrin B 1 and norhalichondrin B 2 are described below, which include preparation of various compounds within the scope of the present invention. Also provided below are the procedures to prepare other halichondrin-related compounds of this invention. Furthermore, results from biological tests showing of anti-tumor activity of some synthetic halichondrin-related compounds are presented. These results indicate that the anti-tumor activity of halichondrin Bs can be largely attributed to their right half moiety.

Note that same or similar reaction conditions are not repeated to avoid redundancy. In any event, a skilled person in the art can prepare the compounds of this invention based on the detailed description of numerous working examples below.

SYNTHESIS OF HALICHONDRIN B AND NORHALICHONDRIN B

Compound 1

Compound 1, halichondrin B, was prepared from compounds 10 and 11 by the following procedure.

(1) Preparation of C38 aldehyde

To a stirred solution of C38 alcohol, i.e., compound 10 which has a 38-carbon skeleton, (8.1 mg, 9.0 μmole) in $CH_2Cl_2$ (1.0 mL) at room temperature was added solid $NaHCO_3$ (50 mg) followed by the Dess-Martin periodinane reagent (15 mg, 36 μmole). Additional Dess-Martin reagent (15 mg, 36 μmole) was added after 30 min. After a total of 90 min, TLC (2:1 ethyl acetate/hexanes) showed no ether (5 mL) and an aqueous solution (5 mL) saturated with $NaHCO_3$ and containing 10% $Na_2S_2O_3$ by wt. The resulting biphasic mixture was stirred at room temperature for 20 min. The separated organic phase was washed with additional aqueous $NaHCO_3/Na_2S_2O_3$ for 10 min, $H_2O$, and brine (5 mL ea.). The organic phase was dried over $Na_2SO_4$, filtered through glass wool, and concentrated. The C38 aldehyde (8 mg, ca. 8.9 μmole) thus obtained was used directly without further purification.

(2) Preparation of halichondrin B enone (C38 ketone)

To a stirred solution of C38 aldehyde (8 mg, 8.9 μmole) and compound 11 (24 mg, 22 μmole) in DMF (ca. 1 mL) under nitrogen was added powdered $CrCl_2$ containing 0.1% $NiCl_2$ by mass (ca. 30 mg total). After stirring at room temperature for 11.5 h, TLC (hexanes/ethyl acetate/$CHCl_3$ 1:2:1) showed no remaining aidehyde. The mixture was diluted with saturated aqueous $NH_4Cl$ (10 mL) and $H_2O$ (2 mL) and extracted with ethyl acetate (4×5 mL). The combined ethyl acetate extracts were washed with $H_2O$ (2×10 mL) and brine (10 mL), dried over $Na_2SO_4$, filtered through glass wool, and concentrated. Purification of the residue by preparative TLC ("PTLC", hexanes/ethyl acetate/$CHCl_3$ 1:2:1) gave the C38 allylic alcohols (11 mg, 6.0 μmole, 67% yield) as a clear, colorless oil and in an approximate 1:1 ratio of diastereomers.

Figure 2:
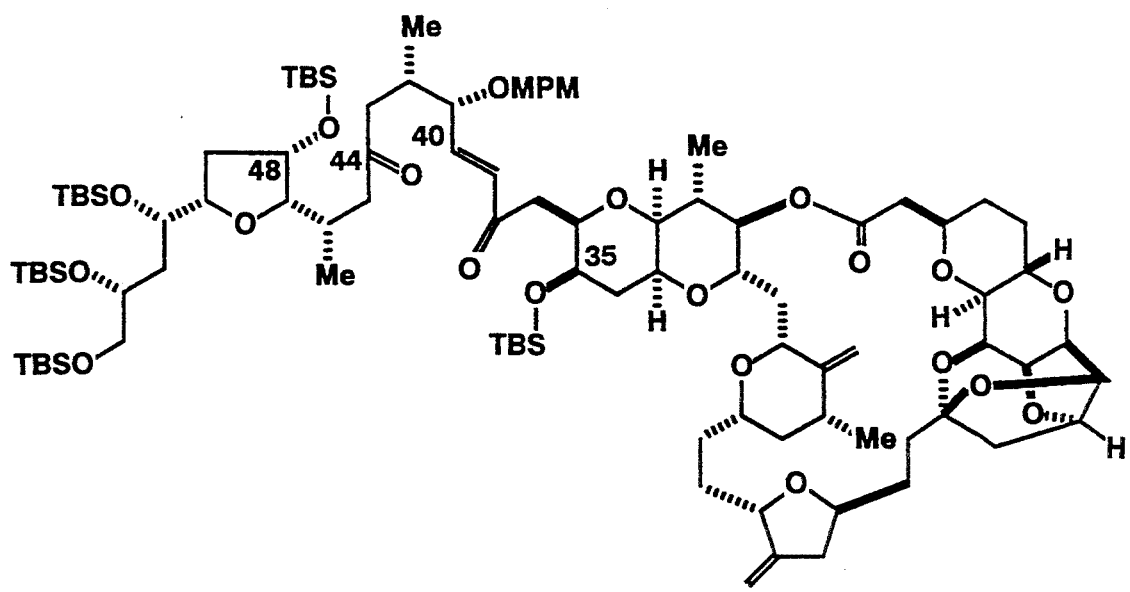
FIG. 2 shows the structures of a halichondrin B enone and a norhalichondrin enone.
Figure 2:
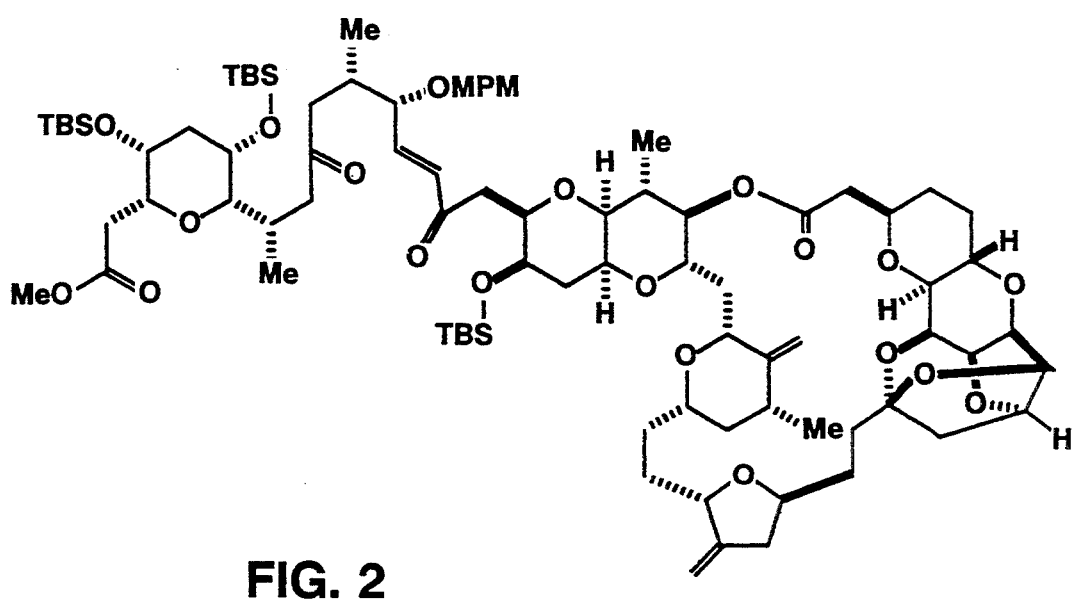

To a stirred solution of the C38 alcohols (8.0 mg, 4.4 μmole) in $CH_2Cl_2$ (2.00 mL) at room temperature was added solid $NaHCO_3$ (50 mg) followed by the Dess-Martin periodinane reagent (14.8 mg, 35 μmole). After stirring at room temperature for 1 h, additional Dess-Martin reagent (14.8 mg) was added. After 90 min total, the reaction mixture was diluted with diethyl ether (6 mL) and an aqueous solution (10 mL) saturated with $NaHCO_3$ and containing 10% $Na_2S_2O_3$ by wt. The resulting biphasic mixture was stirred at room temperature for 20 min. The separated organic phase was washed with additional aqueous $NaHCO_3/Na_2S_2O_3$ for 10 min, $H_2O$, and brine (10 mL ea.). The organic phase was dried over $Na_2SO_4$, filtered through glass wool, and concentrated. Purification of the residue by PTLC (1:1, hexanes/ethyl acetate gave the halichondrin B enone (7.4 mg, 4.1 μmole, 93% yield) as a clear, colorless oil. For the structure of this enone product, see FIG. 2, top.

(3) Preparation of halichondrin B (compound 1)

To a stirred solution of the enone (3.7 mg, 2.0 μmole) in DMF (750 μL) at room temperature was added anhydrous methyl acetate (50 μL) followed by an approximately 1 M solution of tetrabutylammonium fluoride ("TBAF") in THF (25 μL, pH ca. 7.6). The resulting solution was stirred at room temperature for 34 H, at which time high performance TLC ("HPTLC") (E. Merck Art. 5642 plates were spotted with reaction solution, dried on a high vacuum line for 20–30 min, then eluted with 10:1 ethyl acetate/methanol) showed a major spot at $R_f$ 0.53. The reaction solution was filtered through a 2 cm pad of silica gel 60 (230–400 mesh) with ethyl acetate to remove the TBAF. The filtrate was concentrated in vacuo to a yellow oil which was used without further purification. $^1H$ NMR of the crude product showed no α,β-unsaturated ketone proton resonances, but two major products in an approximate 2:1 ration. This compound corresponds to that having partial structure A (see Scheme 2 above).

The above product mixture was dissolved in a mixture of $CH_2CL_2$ (1.00 mL), aqueous phosphate buffer ($Na_2HPO_4/KH_2PO_4H_2O$, pH 7.00, 100 μL) and t-butanol (20 μL). To the resulting rapidly stirred mixture was added 2,3-dichloro-5,6-dicyanobenzoquinone (1.8 mg, 8 μmole). The mixture was sonicated in an $H_2O$ bath for 30 sec, stirred at room temperature without sonication for 3 min, sonicated for an additional 30 sec, and stirred for a final 16 min without sonication. HPTLC (10:1 ethyl acetate/methanol) showed no remaining starting material. The reaction mixture was washed with saturated aqueous $NaHCO_3$ (2×1 mL), $H_2O$, and brine (1 mL ea.). The combined aqueous fractions were extracted with $CH_2Cl_2$ (2×0.5 mL) and the combined organic fractions were dried over $NaSO_4$, filtered, and concentrated to an orange oil. The crude product was dried further on a high vacuum line for 1 h before being used directly in the following reaction.

The above product mixture was dissolved in anhydrous $CH_2Cl_2$ (1.00 mL) and to the stirred room temperature solution was added a solution of (+/−)-camphorsulfonic acid (CSA) in $CH_2Cl_2$ (10 μL of a 1.00 mg CSA/1.00 mL $CH_2Cl_2$ solution). After stirring 2 h at room temperature, HPTLC (10:1 ethyl acetate/methanol) showed essentially complete conversion to a major spot. The reaction solution was washed with saturated aqueous NaHCO₃ (2×0.5 mL), H₂O, and brine (0.5 mL ea). The combined aqueous fractions were extracted with CH₂Cl₂ (2×0.5 mL), and the combined organic fractions were dried over Na₂SO₄, filtered, and concentrated. The residue was chromatographed on HPTLC plates (10:1 ethyl acetate/methanol) to afford synthetic halichondrin B, i.e., compound 1, (1.27 mg, 1.1 μmole, 57% yield over three steps) as a colorless oil.

The synthetic product co-eluted with and was indistinguishable from a sample of the natural product on HPTLC plates in the following five solvent systems and with multiple elutions: (1) 10:1 ethyl acetate/methanol; (2) 10:1 ethyl acetate/CH₂Cl₂; (3) 10:5:1 ethyl acetate/CHCl₃/methanol; (4) 10:5:1 ethyl acetate/CH₂Cl₂/methanol; (5) 10:5:1 ethyl acetate/t-butylmethyl ether/methanol.

IR (cm⁻¹): 1017 cm⁻¹, 1073, 1187, 1737, 2852, 2923, 3438 (br).

¹HNMR (C₆D₆, 500 MHz):

HRMS (FAB): observed m/z=1111.5878 (M+), calcd for C₆₀H₈₆O₁₉ 1111.5841.

[α]$_D$: −51.2° (c 0.127, MeOH).

Compound 2

Compound 2, norhalichondrin B, was prepared from the C38 aldehyde (derived from compound 10 as described above) and compound 12, as follows.

(1) Preparation of norhalichondrin B enone (C38 ketone)

To a stirred solution of the C38 aldehyde (5.4 mg, 6.1 μmole) and compound 12 (13 mg, 12.2 μmole) in DMF (ca. 750 μL) under nitrogen was added powdered CrCl₂ containing 0.1% NiCl₂ by wt. (ca. 20 mg total). The resulting green mixture was stirred at room temperature for 16 h, at which time TLC (2:1:1 ethyl acetate/hexanes/CHCl₃) showed no remaining aldehyde. Saturated aqueous NH₄Cl (1 mL), H₂O (0.5 mL), and ethyl acetate (1mL) were added and the resulting mixture was stirred for 20 min. The upper organic layer was separated and the lower phase was extracted further with ethyl acetate (3×0.5 mL). The combined ethyl acetate fractions were washed with H₂O (2×1 mL) and brine (1 mL), dried over Na₂SO₄, filtered through glass wool, and concentrated. The residue was purified by PTLC (1:1:1, hexanes/ethyl acetate/CHCl₃) to afford the C38 allylic alcohols (8 mg, 5 μmole, 83% yield) as a clear colorless oil as an approximate 1:1 mixture of diastereomers.

To a stirred solution of the C38 alcohols (8 mg, 5 μmole) in CH₂Cl₂ (1.00 mL) at room temperature was added solid NaHCO₃ (50 mg) followed by the Dess-Martin periodinane reagent (17 mg, 40 μmole). After stirring at room temperature for 90 min, TLC (1:1:1 hexanes/ethyl acetate/CHCl₃) showed no remaining starting material. The reaction mixture was diluted with diethyl ether (3 mL) and stirred for 20 min with an aqueous solution (5 mL) saturated with NaHCO₃ and containing 10% Na₂S₂O₃ by wt. The separated organic phase was washed with additional aqueous NaHCO₃/NA₂S₂O₃ for 10 min, H₂O, and brine (5 mL ea.). The organic phase was dried over anhydrous Na₂SO₄, filtered through glass wool, and concentrated. Purification of the residue by PTLC (1:1:1, hexane/ethyl acetate/CHCl₃) gave the norhalichondrin B enone (6.3 mg, 3.9 μmole, 79% yield) as a clear, colorless oil. For the structure of this enone, see FIG. 2, bottom.

IR (cm⁻¹): 835 cm⁻¹, 1088, 1252, 1463, 1737, 2929, 2953.

¹HNMR (C₆D₆, 500 MHz):

HRMS (FAB): m/z=([M+Na]+), calcd for ([C₈₆H₁₃₆O₂₁Si₃+Na]+, 1611.8779; observed, 1611.8811.

[α]$_D$: −32° (C 0.56, MeOH).

(2) Preparation of norhalichondrin B methyl ester

To a stirred solution of the enone (3.15 mg, 2.4 μmole) in THF (400 μL) and anhydrous methyl acetate (200 μL) was added an approximately 1 M solution of tetrabutylammonium fluoride (TBAF) in THF (20 μL, pH ca. 7.6). The resulting solution was stirred at room temperature for 14.5 h, at which time HPTLC (E. Merck Art. 5642 plates were spotted with reaction solution, dried on a high vacuum line for 20–30 min, then eluted with ethyl acetate) showed one major spot at R$_f$ 0.45. The reaction solution was filtered through a 2 cm-pad of silica get 60 (230–400 mesh) with ethyl acetate to remove the TBAF. The filtrate was concentrated in vacuo to a yellow oil which was used without further purification.

The above product mixture was dissolved in CH₂Cl₂ (1.00 mL). Aqueous phosphate buffer (ph 7.00, 100 μL) and t-butanol (20 μL) were added, and to the resulting rapidly stirred mixture was added DDQ (1.8 mg, 8 μmole). The mixture was sonicated in an H₂O bath for 3×30 sec, with stirring at room temperature without sonication for 3–5 min intervals between sonications. TLC (ethyl acetate) at this point showed no remaining starting material. The reaction mixture was washed with saturated aqueous NaHCO₃ (2×1 mL), H₂O, and brine (1 mL ea). The combined aqueous fractions were extracted with CH₂Cl₂ (2×0.5 mL) and the combined organic fractions were dried over NaSO₄, filtered, and concentrated to an orange oil. The crude product was dried further on a high vacuum line for 30 min before being used directly in the following reaction.

The above product was dissolved in anhydrous CH₂Cl₂ (1.00 mL) and to the stirred solution at room temperature was added a solution of (+/−)-camphorsulfonic acid ("CSA") in CH₂Cl₂ (10 μL of a 1.00 mg CSA/1.00 mL CH₂Cl₂ solution). After 1 h, HPTLC (ethyl acetate) showed essentially complete reaction. The reaction solution was washed with saturated aqueous NaHCO₃ (2×0.5 mL), H₂O, and brine (0.5 mL ea.). The combined aqueous fractions were extracted with CH₂Cl₂ (2×0.5 mL), and the combined organic fractions were dried over anhydrous Na₂SO₄, filtered, and concentrated. The residue was chromatographed on HPTLC plates (ethyl acetate) to afford synthetic norhalichondrin B methyl ester (1.2 mg, 1.1 μmole, 45% yield over three steps) as a colorless oil.

The synthetic product co-eluted with and was indistinguishable from an authentic sample (obtained from treatment of natural norhalichondrin B with diazomethane in methanol) upon multiple elutions on HPTLC plates with the two following solvent systems: (1) ethyl acetate (2) 25:1 CH₂Cl₂/methanol.

IR (cm⁻¹): 1021, 1073, 1189, 1435, 1739, 2924, 3609.

HRMS (FAB): (m/z+([M+Na]+), calcd for [C₆₀H₈₄O₁₉+Na]+, 1131.5504; observed 1131.5502.

[α]$_D$: −46.4° (c 0.22, MeOH).

(3) Preparation of norhalichondrin B

To a stirred solution of the methyl ester (2.2 mg, 2.0 μmole) in THF (300 μL) at room temperature was added a 1 M aqueous LiOH solution (100 μL). After stirring for 90 min at room temperature, HPTLC (ethyl acetate) showed complete reaction. The THF was removed under a stream of $N_2$, and the resulting solution was diluted with $H_2O$ (200 μL) and cooled to 0° C. To the rapidly stirred solution was added 1 M aqueous HCl (100 μL). The mixture was extracted wtih ethyl acetate (4×0.5 mL), and the combined extracts were dried over $Na_2SO_4$, filtered through glass wool, and concentrated. The residue was purified on a TSK G 300S polystyrene column (a 2 cm column was equilibrated with $H_2O$, the carboxylic acid was loaded in 50% aqueous ethanol, and eluted with $H_2O$ →ethanol) to afford the carboxylic acid (1.3 mg, 1.2 μmole, 60% yield) as a colorless oil. This compound is norhalichondrin B (compound 2).

The procedures which were used to prepare the intermediates (compounds 3-12, Schemes 1 and 2) required for the above-described synthesis of halichondrin B 1 and norhalichondrin B 2 are set forth below.

Compound 3

Compound 3 was synthesized according to the following procedure.

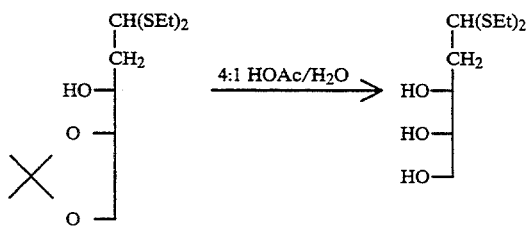

To the monoacetonide (50.4 g, 0.179 mol) was added 250 mL of 4:1 $HOAc/H_2O$ and stirred overnight at room temperature. The reaction mixture was concentrated under reduced pressure and purified by flash chromatography (100% EtOAc) to yield the triol (40.6 g, 94% yield).

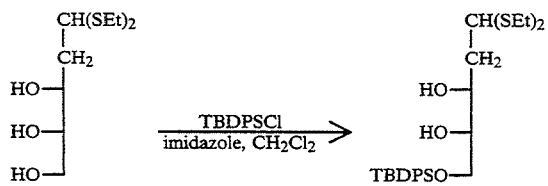

To the triol (40.6 g, 0.169 mol) in $CH_2Cl_2$ at 0° C. was added imidazole (50.0 g, 0.734 mol), t-butyldiphenylsilylchloride ("TBDPSCl" 51.0 g, 0.186 mol) then stirred for 1 h at 0° C. and 1 h at room temperature. The reaction mixture was diluted with $CH_2Cl_2$ and washed with aqueous $NaHCO_3$ (2x). The aqueous layer was back extracted with $CH_2Cl_2$ (4x), and the combined organic layers were dried over $Na_2SO_4$. Concentration under reduced pressure afforded an oil which was purified by flash chromatography (4:1 Hexanes/EtOAc) to yield the diol (75.7 g, 94% yield) as a colorless oil.

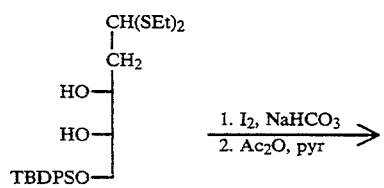

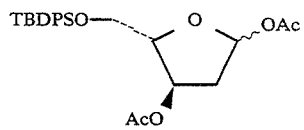

To a stirred solution of thioacetal (75.7 g, 0.158 mol) and $NaHCO_3$ (79.7 g, 0.949 mol) in acetone (550 mL) and $H_2O$ (90 mL) at 0° C. was added iodine (120.4 g, 0.474 mol). After 0.5 h TLC (1:1 hexanes/EtOAc) indicated complete absence of the starting thioacetal. The reaction mixture was quenched by addition of aqueous $Na_2S_2O_3$ and the acetone was removed under reduced pressure. The mixture was extracted with EtOAc (4x) and the combined organic layers were washed with brine (1x), $H_2O$ (1x) then dried over $Na_2SO_4$ and concentrated under reduced pressure to afford the furanose as a yellow oil. To the crude furanose was added pyridine (75 mL), $Ac_2O$ (80.5 g, 0.789 mol, 74 mL) and dimethylaminopyridine ("DMAP" 19 g, 0.0157 mol) at room temperature. The reaction was stirred overnight, concentrated under reduced pressure then purified by flash chromatography (3:1 hexanes/EtOAc) to afford the diacetate (67.7 g, 94% yield) and an oil IR (film) 606 cm$^{-1}$ 702, 997, 1113, 1230, 1742, 2932, 2958, 3072.

$^1$H NMR (CDCl$_3$): δ1.91 (OAC, s), 2.06 (OAc, s), 2.08 (OAc, s), 2.09 (OAC, s), 2.18 (0.5H, m), 2.27 (0.5H, m), 2.49 (0.5H, m), 2.56 (0.5H, m), 3.78 (1.5H, m), 3.86 (0.5H, dd), 4.18 (0.5H, m), 4.31 (0.5H, m), 5.37 (0.5H, dd), 5.42 (0.5H, m), 6.38 (0.5H, dd), 6.42 (0.5H, d), 7.39 (6H, m), 7.69 (4H, m).

HRMS (FAB) calcd for $C_{25}H_{32}O_6Si+Na$ 479.1866, found 479.1891.

$[α]_D$ −18.6° (C 1.81, MeOH).

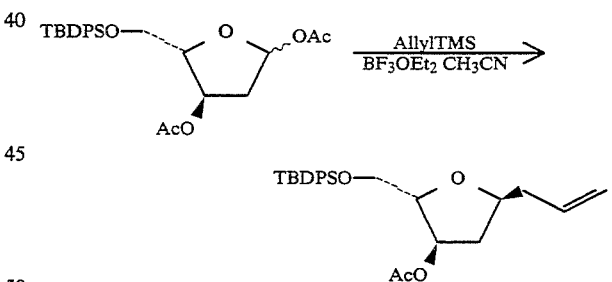

To an ice cold solution of the diacetate (67.7 g, 0.148 mol) and allyltrimethylsilane (50.8 g, 0.444 mol, 70.6 mL) in $CH_3CN$ was added $BF_3.OEt_2$ (21.0 g, 0.148 mol, 18.2 mL) dropwise over 10 min. The reaction mixture was stirred for an additional 15 min then quenched with dilute aqueous $NaHCO_3$. The mixture was extracted with EtOAc (3x) and the combined organic layers dried over $Na_2SO_4$. Concentration under reduced pressure and purification by flash chromatography (5:1 hexanes/EtOAc) afforded an oil (58.9 g, 90% yield).

IR (film) 702 cm$^{-1}$ 1113, 1247, 1759, 2867, 3079.

$^1$H NMR (CDCl$_3$, 500 MHz): δ1.05 (9H, s, t-Bu), 1.74 (1H, m), 2.06 (3H, s, O—CH$_3$), 2.31 (1H, m), 2.44 (1H, m), 2.49 (1H, m), 3.71 (1H, dd, J. 4.5, 10.9 Hz), 3.76 (1H, dd, J=3.7, 10.9 Hz), 4.09 (1H, m), 4.24 (1H, p, J=6.6 Hz), 5.09 (2H, m), 5.36 (1H, m, CH-OAc), 5.81 (1H, m), 7.39 (6H, m), 7.67 (4H, m).

HRMS (FAB) calcd for $C_{26}H_{34}O_4Si$ (M+Na)+ 461.2124, found 461.2138.

$[\alpha]_D$ −16.9° (C 1.25, MeOH).

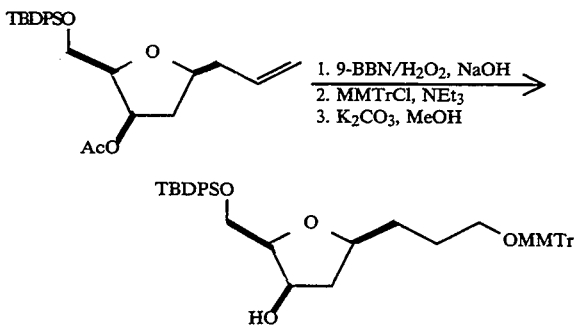

To a solution of olefin (24.1 g, 55 mmol) in THF (400 mL) at 0° C. was added 0.5 M 9-BBN in THF (142 mL, 71.5 mmol). The reaction mixture was allowed to warm to room temperature and stir overnight. The solution was cooled to 0° C. and 10% NaOH (90 mL) was added followed by 30% $H_2O_2$ (90 mL). After stirring for 2 h, the reaction was quenched by addition of aqueous $NH_4Cl$ and extracted with EtOAc (3×600 mL). The combined organic layers were washed with aqueous $K_2CO_3$ (2x), dried over $NaSO_4$ and concentrated under reduced pressure. Note that some hydrolysis of acetate was observed. Therefore the crude mixture was used for selective funtionalization of the primary alcohol without purification.

To a solution of the crude alcohol in $CH_2Cl_2$ (300 mL) was added $Et_3N$ (54 mL, 385 mmol) followed p-anisylchlorodiphenylmethane (18.7 g, 60.5 mmol) at 0° C. The reaction was stirred for 8 h then quenched with aqueous $NaHCO_3$ and extracted with $CH_2Cl_2$ (2×100 mL). The combined organic layers were dried over $Na_2SO_4$, concentrated under reduced pressure. Powdered $K_2CO_3$ (4 g) was added portionwise to a solution of the crude acetate in THF (10 mL) and MeOH (300 mL). The reaction was stirred for 2.5 h at room temperature then filtered through Celite and purified by flash chromatography with 20% EtOAc in hexanes to afford the desired product (26.7 g, 70.8% yield over 3 steps).

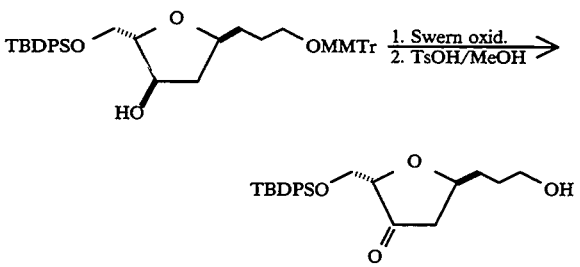

To a solution of oxalyl chloride (1.33 mL, 15.3 mmol) in $CH_2Cl_2$ (150 mL) was added DMSO (2.16 mL, 30.2 mmol) dropwise over 3 min at −78° C. After stirring for 10 min, a solution of alcohol in $CH_2Cl_2$ (10 mL) was added over 5 min. The empty flask was washed with additional $CH_2Cl_2$ (3 mL) and the solution was added to the reaction mixture. After stirring for 1 h, $NEt_3$ (8.55 mL, 60.4 mmol) was added to the reaction mixture. The reaction mixture was stirred for additional 15 min and warmed to room temperature over 45 min. The reaction mixture was quenched with saturated $NH_4Cl$ and the organic layer was separated. The organic layer was washed with water, brine, dried over $Na_2SO_4$, and concentrated. The residue was purified by column chromatography with 20% EtOAc in hexanes to give the ketone (2.37 g, 97% yield).

To a solution of MMTr-ketone (9.3 g, 13.5 mmol) in $CH_2Cl_2$ (200 mL) and MeOH (50 mL) was added TsOH (1 g) at room temperature. After stirring for 2 h, solid $NaHCO_3$ was added to the reaction mixture to neutralize TsOH. After stirring for 1 h, the reaction mixture was filtered, concentrated, and purified by column chromatography with 33% EtOAc in hexanes to afford the keto-alcohol (5.4 g, 96.6% yield).

IR (film) 703 $cm^{-1}$ 743, 823, 1077, 1113, 1428, 1759, 2893, 2930, 3071, 3438.

$^1H$ NMR ($CDCl_3$): δ1.01 (9H, s), 1.57 (1H, br s), 1.75 (2H, m), 1.80 (2H, m), 2.28 (1H, dd, J=8.3, 17.9 Hz), 2.66 (1H, dd, J=6.5, 17.9 Hz), 3.73 (2H, m), 3.87 (1H, dd, J=2.2, 11.1 Hz), 3.97 (1H, dd, J=2.4, 11.1 Hz), 4.03 (1H, br s), 4.73 (1H, m), 7.43 (6H, m), 7.68 (2H, m), 7.70 (2H, m).

HRMS (FAB) calcd for $C_{24}H_{32}O_4Si+Na$ 435.1968, found 435.1954.

$[\alpha]_D$ −19.2° (c 1.2, MeOH).

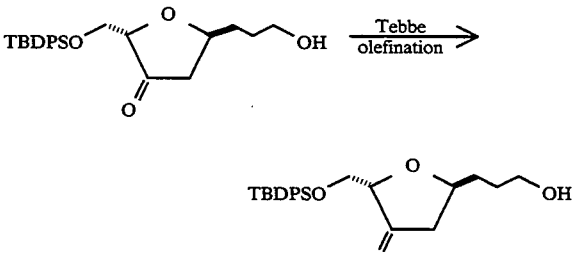

To a well-stirred solution of the keto alcohol (747 mg, 1.81 mmol) in a 3:1:1 mixture of toluene:THF:pyridine (11 mL) at 0° C. was added dropwise a freshly prepared solution of Tebbe reagent [prepared in situ according to the procedure of Grubbs: Grubbs, R. M.; Cannazzo, L. F. J. Org. Chem., 50, 2386 (1985)] (8.3 mL, about 3 eq) over 15 min. TLC (50% ethyl acetate/hexanes) indicated complete loss of starting material in about 0.5 h. The reaction was quenched by cautious addition of 0.1 N NaOH (10 mL) The mixture was diluted with ether and the solution vigorously stirred until the organic layer was light yellow. The layers were separated and the aqueous phase extracted with ether. The combined organic fractions were exhaustively washed with water to remove pyridine, then with brine. The organic layers were dried over sodium sulfate, and removed in vacuo. The residue was purified by flash chromatography (40% ethyl acetate/hexanes) to afford the exocyclic olefin (647 mg, 87% yield).

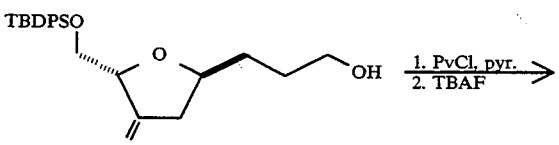

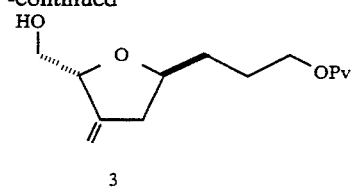

3

To a stirred solution of an alcohol (5.24 g, 12.8 mmol) in CH$_2$Cl$_2$ (90 mL) at room temperature was added pyridine (62 mL, 76.6 mmol), DMAP (50 mg), and pivaloyl chloride (8.3 mL, 67.7 mmol). After stirring for 1 h, the reaction mixture was quenched with saturated NHCl, diluted with CH$_2$Cl$_2$, and extracted. The combined organic layers were washed with 10% HCl, water, saturated NaHCO$_3$, brine, and dried over Na$_2$SO$_4$. The solvents were concentrated under reduced pressure.

To a solution of crude pivaloate in THF (140 mL) was added 1 M TBAF in THF (20 mL, 20 mmol) dropwise at room temperature. After stirring for 1.1 h, the reaction mixture was concentrated under reduced pressure, and the residue was purified by column chromatography with 15% EtOAc in hexanes to afford the desired product (2.98 g, 91% yield over 2 steps).

IR (film) 1157 cm$^{-1}$1284, 1480, 1727, 2872, 2959, 3078, 3453.

$^1$H NMR (CDCl$_3$): δ1.19 (9H, s), 1.55 (1H, m), 1.67 (2H, m), 1.77 (1H, m), 1.93 (1H, m), 2.29 (1H, dd), 2.70 (1H, dd), 3.61 (2H, m), 4.09 (3H, t, J=6.3 Hz), 4.50 (1H, br), 4.92 (1H, m), 5.08 (1H, m).

HRMS (CI) calcd for C$_{14}$H$_{24}$O$_4$+H (M+H)$^+$257,1753, found (M+H)$^+$257.1744.

[α]$_D$ −27.2° (C 1.1, MeOH).

Compound 4

Compound 4 was synthesized according to the following procedure.

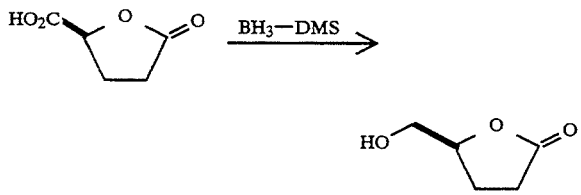

To a solution of the carboxylic acid (42 g, 0.32 mol) in dry THF (300 mL) was added at room temperature BH$_3$DMS (39 mL, neat, 0.39 mol) at such a rate as to maintain gentle reflux. After an additional 3 h, the mixture was cooled to 0° C., and cautiously quenched with excess methanol (500 mL). The solvents were removed by distillation at atmospheric pressure, and the residue purified by distillation in vacuo to afford 34.3 g of pure alcohol.

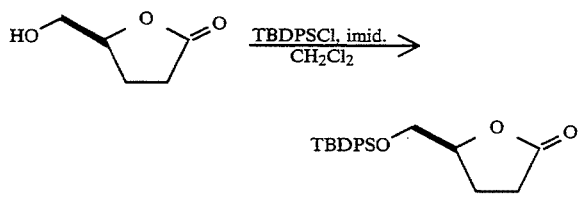

To a stirred solution of the lactone I (12.5 g, 108 mmol) and imidazole (15.6 g, 229 mmol) in CH$_2$Cl$_2$ 300 mL) at 0° C. was added t-butyldiphenylsilyl chloride (29.0 mL, 112 mmol). The mixture was allowed to stir at room temperature overnight. The mixture was diluted with CH$_2$Cl$_2$, then washed with saturated NaHCO$_3$, water, brine, dried (Na$_2$SO$_4$), and concentrated under reduced pressure. The mixture was purified by crystallization from hexane, yielding the silyl ether II (30.05 g in the first crop, and an additional 5.40 g in the second crop; 93% combined yield, mp 84° C.).

IR (film): 3072 cm$^{-1}$ 3049, 2998, 2931, 2893, 2858, 1777, 1590, 1473, 1461, 1427, 1391, 1346, 1174, 1113, 1084, 1032, 995, 941, 858, 822, 741, 703.

$^1$H NMR (CDCl$_3$): δ1.07 m), (9H, S), 2.19-2.34 (2H, 2.52 (1H, m), 2.69 (1H, m), 3.70 (1H, dd, J=3.3, 11.3 Hz), 3.90 (1H, dd, J=3.2, 11.3 Hz), 4.61 (1H, m), 7.30-7.50 (6H, m), 7.60-7.80 (4H, m).

$^{13}$C NMR (CDCl$_3$): δ19.22, 23.65, 26.78, 28.55, 65.45, 79.89, 127.70, 129.77, 135.38, 135.47, 177.37.

[α]$_D$: +24.9° (C 5.91, CHCl$_3$).

Analysis calcl for C$_{21}$H$_{26}$O$_3$Si: C 71.15, H 7.39; found: C 70.91, H 7.42.

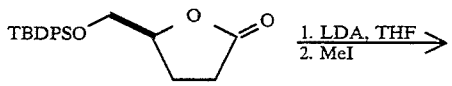

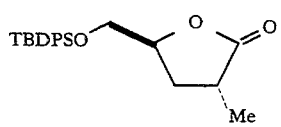

To a stirred solution of diisopropylamine (3.88 mL, 27.69 mmol) in THF (10 mL) at −78° C. was added a 2.35 M solution of n-butyllithium in hexane (11.8 mL, 27.69 mmol). After stirring the resulting mixture for 20 min, a solution of the lactone II (9.347 g, 26.4 mmol) in THF (20 mL) was slowly added via cannula. After stirring the mixture 25 min at −78° C., methyl iodide (4.85 mL, 77.9 mmol) was added. After 35 min, the reaction was quenched by the careful addition of saturated NH$_4$Cl. The mixture was allowed to warm to 0° C., and then diluted with ether. The layers were separated, and the aqueous layer was reextracted with ether. The combined organic layers were washed with water, brine, dried over Na$_2$SO$_4$), and concentrated under reduced pressure. Crystallization with hexane yielded the major methylated product III (mp 84° C., 7.3 g, 75% yield). The mother liquor contained 1.4 g of a mixture of the two methylated compounds.

IR (film): 3072 cm$^{-1}$ 3051, 2958, 2932, 2859, 1774, 1473, 1462, 1428, 1362, 1349, 1202, 1173, 1113, 1067, 1022, 998, 954, 935, 822, 742, 727, 702, 623.

$^1$H NMR (CDCl$_3$): δ1.06 (9H, s), 1.27 (3H, d, J=7.1 Hz), 1.98 (1H, m), 2.47 (1H, m), 2.86 (1H, m), 3.67 (1H, dd, J=3.3, 11.3 Hz), 3.88 (1H, dd, J=3.5, 11.3 Hz), 4.56 (1H, m), 7.30-7.50 (6H, m), 7.70-7.80 (4H, m).

$^{13}$C NMR (CDCl$_3$): δ16.47, 19.25, 26.84, 32.27, 34.24, 65.57, 77.49, 127.74, 129.81, 132.49, 132.87, 135.42, 135.51, 179.82.

MS (FAB): 369 amu (M$^+$+H, rel. intensity 2%), 313 (6), 312 (18), 311 (74), 293 (7), 292 (24), 291 (100), 233 (17), 199 (29), 197 (36), 163 (27), 135 (86).

[α]$_D$: +1.3° (C 1.43, CHCl$_3$).

Analysis calcd for C$_{22}$H$_{28}$O$_3$Si.¼ H$_2$O: C 71.70, H 7.66; found: C 70.84, H 7.54.

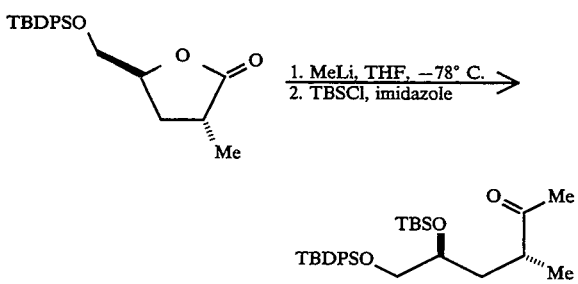

To a solution of lactone (46.2 g, 0.125 mol) in THF (400 mL) was added 1.4 M MeLi in ether (89.5 mL, 0.125 mol) over 10 min at −78° C. After stirring for 10 min, the reaction mixture was poured into saturated NH4Cl solution (300 mL) and extracted with EtOAc (3×300 mL). The combined organic layers were washed with brine (200 mL), dried over Na2SO4, and concentrated under reduced pressure.

To a solution of crude hemiketal in CH2Cl2 (600 mL) was added imidazole (22.2 g, 0.150 mol), followed by t-butyldimethylsilyl chloride (TBDMSCl, 22.2 g, 0.325 mol). The resulting reaction mixture was stirred for 36 h at room temperature. The reaction mixture was washed with saturated NaHCO3, water, and brine. The organic layer dried over Na2SO4, and concentrated under reduced pressure. The residue was purified by column chromatography with 10% EtOAc in hexanes to afford 51.3 g of disilyl ether (82.4% yield) as a colorless oil.

IR (film) 1112 cm$^{-1}$ 1254, 1462, 1473, 1716, 2886, 2930, 2957.

$^1$H NMR (CDCl3): δ−1.20 (3H, s), −0.50 (3H, s), 0.81 (9H, s), 1.06 (9H, s), 1.11 (3H, d, J=7.1 Hz), 1.47 (1H, m), 2.12 (3H, s), 2.15 (1H, m), 2.71 (1H, m), 3.46 (1H, dd, J=7.2, 10.1 Hz), 3.57 (1H, dd, J=4.6, 10.1 Hz), 3.70 (1H, m), 7.42 (6H, m), 7.66 (4H, m).

HRMS (FAB) calcd C29H46O3Si2+Na 521.2853, found 521.2885.

[α]$_D$−13.0° (C 1.15, MeOH).

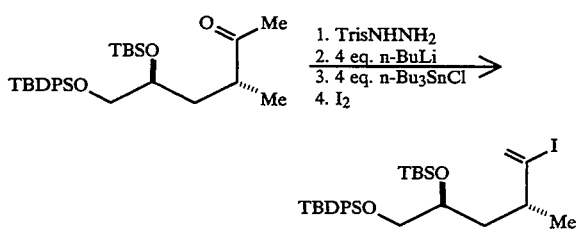

To a solution of ketone (7.1 g, 14.26 mmol) in THF (16 mL) was added TrisNHNH2 (5.1 g, 1.2 eq) followed by 1 drop of conc. HCl. After stirring for 4 h, the reaction mixture was directly concentrated, further dried by azeotropic removal of water with benzene (×2) and then under high vacuum. The crude hydrazone was dissolved in TMEDA/pentane (30/120 mL) and cooled to −78° C. and the reaction mixture was treated with 2.06 M n-BuLi (27.5 mL, 4 eq) for 30 min. The reaction mixture was then warmed to 0° C. and held under ice bath for 10 min (red to yellow). The vinyl lithium solution was cooled to −78° C. and n-Bu3SnCl (15 mL, 3.9 eq) was added very slowly. When the stirring was hard, temperature was adjusted to −15° C. and the reaction mixture was stirred for 1 h at the same temperature and for 1 h at 0° C. (almost colorless solution). The reaction mixture was diluted with ether (100 mL) and washed with saturated NH4Cl, water, and brine. The organic layer was dried over Na2SO4, concentrated, and purified by column chromatography with hexanes to 10% toluene in hexanes to afford the vinyl tin compound.

The vinyl tin compound was dissolved in CH2Cl2 (100 mL) and titrated with a solution of iodine until it showed purple color at 0° C. The reaction mixture was washed with NaHSO3 solution, water, and brine. The organic layer was concentrated and the residue was purified by column chromatography with 10% toluene in hexanes to afford 6.76 g of vinyl iodide compound with 78% yield.

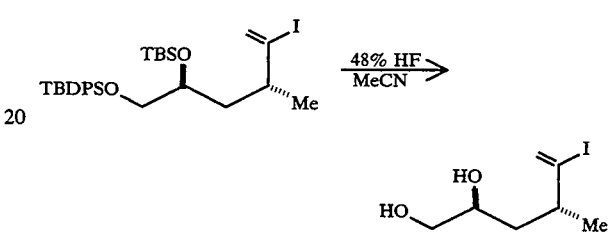

To a solution of silyl ether in MeCN (90 mL) and THF (10 mL) was added 48% HF (1.2 mL, 3 eq). After stirring for 10 h, solid NaHCO3 (5 g) and EtOAc (300 mL) was added and stirred until bubbling was stopped. Filtered, concentrated, and purified by column chromatography with gradient elution of 10 % EtOAc in CHCl3 to EtOAc to afford 1.79 g of diol (70% yield). Because of volatility of diol, this yield was low. One does not need to dry diol rigorously to get better yield, since the next step will be done in aqueous media.

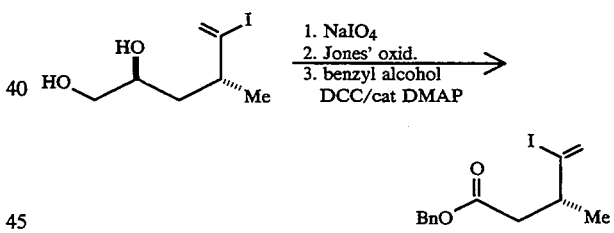

To a solution of diol (1.79 g, 7.02 mmol) in THF (15 mL) and water (7 mL) was added NaIO4 at room temperature. After stirring for 1 h, the reaction mixture was diluted with water until it formed a clear solution, followed by extraction with ether (2×20 mL). The organic layer was washed with NaHSO3 solution to remove excess oxidant. The organic layer was concentrated under reduced pressure without drying. The crude aldehyde was diluted with acetone (50 mL). The resulting solution was cooled to 0° C. and treated with Jones reagent. After the reaction was complete, the excess Jones reagent was quenched with isopropanol. The reaction mixture was filtered through Celite, concentrated, diluted with ether, and washed with water and brine. The organic layer was dried over MgSO4, concentrated, and further dried by azeotropic removal of water with benzene (×2).

To a solution of crude acid in CH2Cl2 (20 mL) was added benzyl alcohol (1 mL, 1.4 eq) followed by diisopropylcarbodiimide ("DCC" 1.74 g, 12 eq) with a catalytic amount of DMAP (5%) at room temperature. After stirring for 12 h, extra DCC (0.5 g, 0.34 eq) along with benzyl alcohol (0.5 mL, 0.7 eq) was added to the reaction mixture. After 6 h, the reaction mixture was concentrated, diluted with ether (5 mL), and filtered through Celite. The filtrate was concentrated and purified by column chromatography with 9% EtOAc in hexanes to afford the benzyl ester (2.16 g, 93.5% yield).

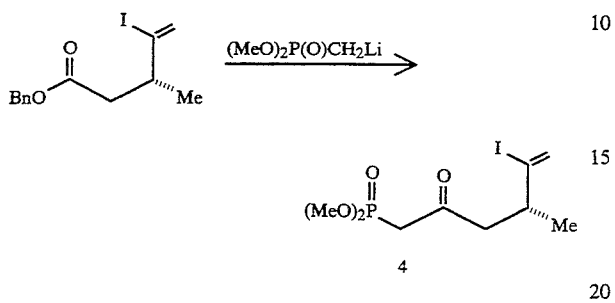

To a solution of phosphonate (3.4 g, 27.2 mmol) in THF (16 mL) was added 2.13 M n-BuLi at −78° C. After stirring for 1 h, the benzoate (2.5 g, 7.58 mmol) in THF (4 mL) was added dropwise. After 20 min, the reaction mixture was quenched with saturated NH$_4$Cl and extracted with EtOAc (3×20 mL). After drying over Na$_2$SO$_4$ and concentration, the residue was purified by column chromatography with EtOAc in hexanes (50% to 80%) to afford 1.90 g of ketophophonate (78.4% yield) along with 249 mg of recovered benzoate (10% yield). Yield based on recovered starting material was 87%.

IR (film) 1028 cm$^{-1}$ 1262, 1613, 1715, 2959.

$^1$H NMR (CDCl$_3$): δ1.03 (3H, d, J=6.1 Hz), 2.57 (2H, m), 2.81 (1H, m), 3.08 (2H, m), 3.78 (3H, s, -OMe), 3.80 (3H, s, -OMe), 5.72 (1H, d, J=1.4 Hz), 6.19 (1H, s).

HRMS (FAB) calcd for C$_9$H$_{16}$O$_4$PI+Na 368.9729, found 368.9744.

[α]$_D$−2.4° (C 4.9, MeOH).

Compound 5

Compound 5 was synthesized according to the following procedure.

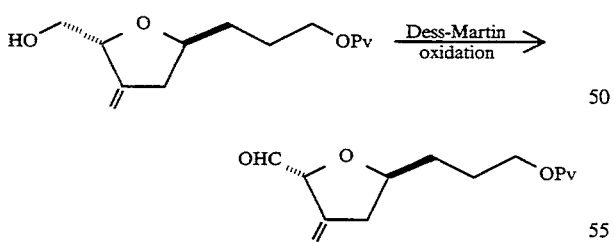

To a solution of the alcohol (180 mg, 0.706 mmol) in dichloromethane (12 mL) at room temperature was added Dess-Martin reagent (449 mg, 1.5 eq) along with 3Å molecular sieves (2 g). After stirring for 25 min, the reaction mixture was diluted with ether (60 mL) and filtered through Celite. The filtrate was washed with 6 eq of sodium dithionate solution in saturated NaHCO$_3$ solution (20 mL), saturated NaHCO$_3$, water and brine. The organic layer was dried concentrated and further dried by azeotrope. The crude aldehyde was used in the next step without further purification.

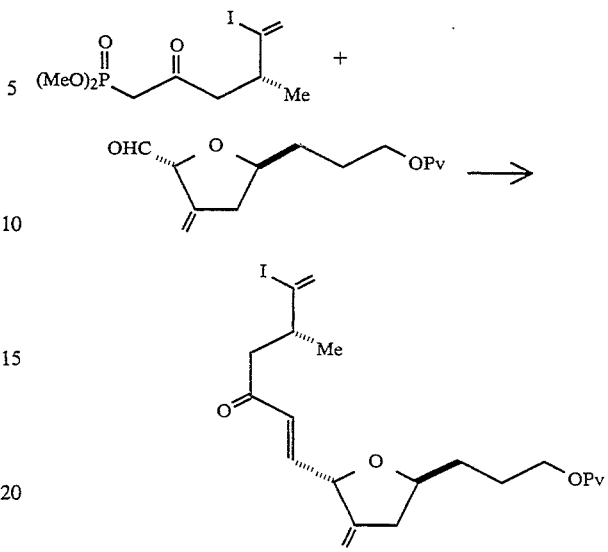

To a solution of the ketophosphonate (333 mg, 1.06 mmol) in dry THF (4 mL) at 0° C. was added NaH (38 mg, 0.95 mmol). After stirring for 0.5 h, the aldehyde in THF (2 mL) was added dropwise over 5 min. After stirring for an additional 0.5 h the reaction was quenched with saturated ammonium chloride, and extracted with ethyl acetate. The organic layers were dried over sodium sulfate, and concentrated in vacuo. Purification via flash chromatography (20% ethyl acetate/hexanes) afforded the pure enone (295 mg, yield).

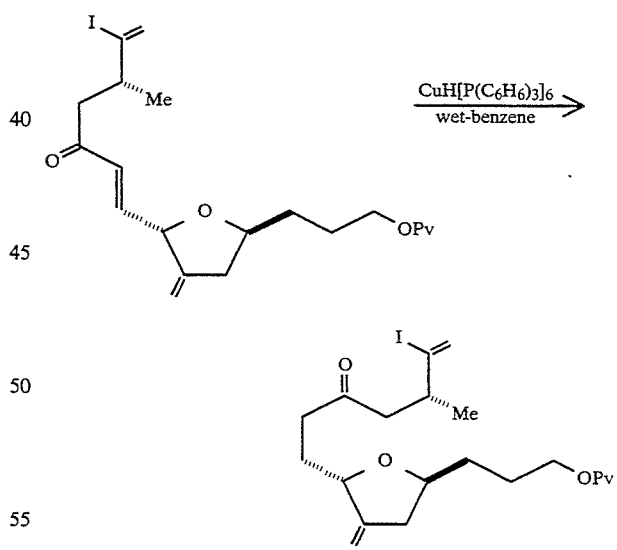

To a solution of enone (650 mg, 1.37 mmol) in 65 mL of degassed benzene and 0.4 mL (16 eq) of degassed water was added [CuH(Ph$_3$P)]$_6$ (806 mg, 1.8 eq). The red reaction mixture was stirred for 3 h under argon and then the reaction vessel was opened to air to decompose excess reagent. After 1 h, the black reaction mixture was filtered through Celite. The filtrate was concentrated under reduced pressure and purified by column chromatography with 6% ethyl acetate in hexanes to afford the ketone in (605 mg, 93% yield).

IR (film) 898 cm$^{-1}$ 1174, 1336, 1726, 2934, 2962.

¹H NMR (CDCl₃): δ1.02 (3H, d, J=6.5 Hz, CH₃), 1.58 (9H, s, -OPv), 1.50 (1H, m), 1.61 (2H, m), 1.72 (2H, m), 1.87 (1H, m), 2.25 (1H, m), 2.33 (1H, dd, J=6.9, 16.3 Hz), 2.54 (3H, m), 2.67 (2H, m), 3.99 (1H, m), 4.06 (2H, m), 4.35 (1H, m), 4.87 (1H, d, J=2.0 Hz), 5.00 (1H, d, J=2.1 Hz), 5.70 (1H, d, J=1.7 Hz), 6.17 (1H, d, J=1.3 Hz).

HRMS (FAB) calcd for C₂₁H₃₃O₄I+Na 499.1323, found 499.1334.

[α]$_D$ −37.0° (c 1.01, MeOH).

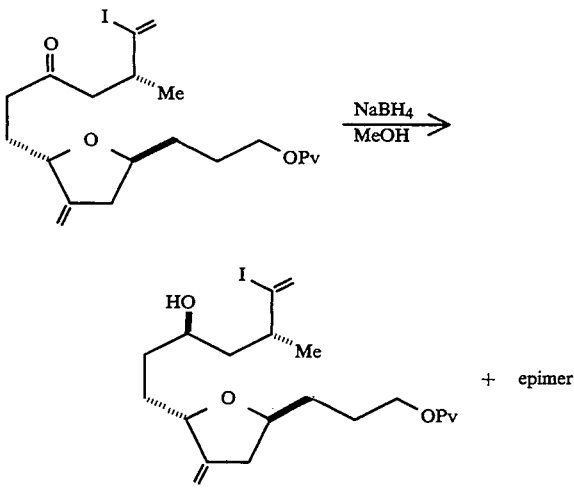

To a solution of ketone (1.26 g, 2.65 mmol) in MeOH (20 mL) at 0° C. was added NaBH₄ (130 mg, 3.38 mmol). After stirring for 20 min at the same temperature, the reaction mixture was quenched with saturated NH₄Cl and extracted with EtOAc (3×20 mL). The combined organic layers were dried over Na₂SO₄, concentrated, and purified by column chromatography with 8/2/1 (hexanes/EtOAc/CHCl₃) to afford a desired higher Rf alcohol (877 mg, 69.6% yield), an undesired lower Rf alcohol (372 mg, 29.5% yield), and a mixed fraction (56 mg, 4.4% yield).

IR (film) 1157 cm⁻¹ 1285, 1728, 2930, 2959, 3440.

¹H NMR (CDCl₃): δ0.98 (3H, d, J=6.5 Hz), 1.19 (9H, s, -OPv), 1.25–1.70 (11H, m), 2.08 (1H, m), 2.27 (1H, m), 2.47 (1H, br s), 2.70 (1H, m), 3.58 (1H, m), 4.07 (2H, m), 4.39 (1H, m), 4.86 (1H, m), 5.00 (1H, m), 5.75 (1H, d, J=1.3 Hz), 6.24 (1H, br s).

HRMS (FAB) calcd for C₂₁H₃₅O₄I+Na 501.1480, found 501.1485.

[α]$_D$−82.2° (c 0.9, MeOH).

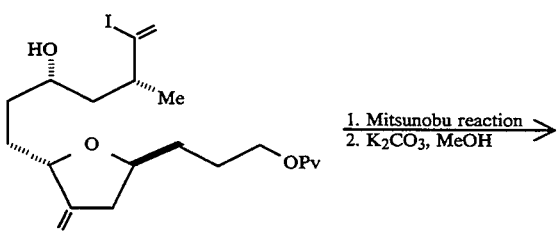

-continued

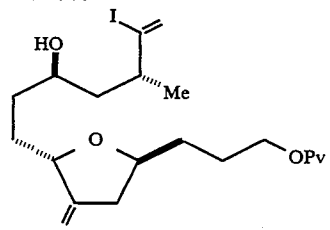

To a solution of alcohol (364 mg, 0.76 mmol) in ether (16 mL) were added Ph₃P (478 mg, 2.4 eq), and p-nitrobenzoic acid (280 mg, 2.4 eq), followed by diethyl azodicarboxylate (250 μL, 2.4 eq). The reaction mixture was stirred for 1 h and hexanes (20 mL) was added. The reaction mixture was filtered through SiO₂ eluting with 30% ethyl acetate in hexanes to remove excess reagents. The filtrate was concentrated and the residue was dissolved in benzene. The suspension was applied to a silica gel column through a glass wool plug to remove insolubles. Purification by column chromatography with 10% ethyl acetate in hexanes gave the benzoate (422 mg, 88.9% yield).

The benzoate was dissolved in MeOH (20 mL) with K₂CO₃ (2 mg). The reaction mixture was stirred until the starting material was completely consumed. HOAc (1 or 2 drops) was added to neutralize or acidify the reaction mixture. After stirring for 10 min, the reaction mixture was concentrated and purified by column chromatography with 13% EtOAc in hexanes to give the inverted alcohol (319 mg, 99% yield).

IR (film) 1157 cm⁻¹ 1285, 1728, 2930, 2959, 3440.

¹H NMR (CDCl₃):. δ0.98 (3H, d, J=6.5 Hz), 1.19 (9H, s, -OPv) 1.25–1.70 (11H, m), 2.08 (1H, m), 2.27 (1H, m), 2.47 (1H, br s), 2.70 (1H, m), 3.58 (1H, m), 4.07 (2H, m), 4.39 (1H, m), 4.86 (1H, m), 5.00 (1H, m), 5.75 (1H, d, J=1.3 Hz), 6.24 (1H, br s).

HRMS (FAB) calcd for C₂₁H₃₅O₄I+Na 501.1480, found 501.1485.

[α]$_D$−82.2° (c 0.9, MeOH).

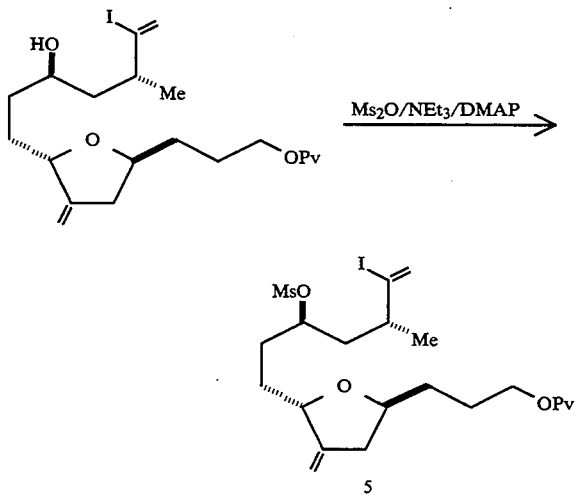

To a solution of alcohol (14.6 mg, 0.03 mmol) in CH₂Cl₂ (1 mL) was added catalytic DMAP, NEt₃ (7.7 μL, 1.8 eq), and Ms₂O (7.5 mg, 1.5 eq). After 30 min, the reaction mixture was quenched with saturated NaHCO₃ solution and extracted with ethyl acetate (2×5 mL). The combined organic layers were washed with brine, dried, and concentrated. The crude residue was briefly filtered through SiO₂ plug with 25% ethyl acetate in hexanes to give 16.3 mg of the mesylate, compound 5, in 96% yield.

IR (film) 898 cm⁻¹ 1173, 1337, 1355, 1725, 2871, 2934, 2962.

¹H NMR (CDCl₃): δ1.01 (3H, d, J=6.5 Hz), 1.19 (9H, s), 1.45–1.80 (9H, m), 1.84 (1H, m), 1.90 (1H, m), 2.27 (1H, dd, J=5.7, 15.3 Hz), 2.68 (1H, dd, J=6.4, 15.3 Hz), 3.02 (1H, s), 4.05 (1H, m), 4.07 (1H, m), 4.37 (1H, m), 4.69 (1H, m), 4.88 (1H, s), 5.01 (1H, s), 5.85 (1H, s), 6.36 (1H, s).

Compound 6

Compound 6 was synthesized according to the following procedure.

(1) Preparation of
3,5-Di-O-tert-butyldimethylsily-D-galactal (after: Kinzy, W. wt al. Tetrahedron Letters 28:1981–1984, 1987; and Horton, D. et al. O. Carbohydrate Research 144:325–330, 1990)

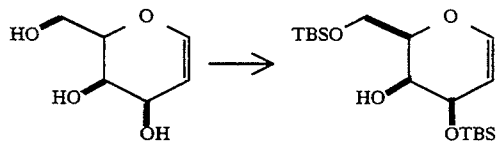

To a stirred solution of D-galactal (Kozikowski, A. P.; Lee, J. J. Org. Chem. 55:863–870, 1990) (18.188 g, 125 mmol) in dry N,N-dimethylformamide (62 mL) at room temperature was added imidazole (42.35 g, 622.9 mmol) followed by tert-butyldimethylsilyl chloride (41.36 g, 274 mmol). The resulting mixture was stirred at room temperature for 2.2 h, at which time TLC (hexanes/ethyl acetate/chloroform; 2:1:1) showed complete disilylation. The reaction mixture was poured into H₂O (1 L) and the resulting mixture was extracted with hexanes (3×500 mL). The combined extracts were washed with H₂O and brine (500 mL ea). The organic phase was dried over MgSO₄, filtered, and concentrated to give the crude disilyl ether (46.93 g) as a clear oil. This material was benzylated without further purification.

(2) Preparation of
4-O-Benzyl-3,5-di-O-tert-butyldimethylsilyl-D-galactal

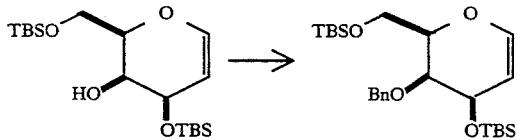

To a stirred 0° C. solution of the crude alcohol (46.93 g, ca. 125 mmol) in a mixture of THF and DMF (4:1 v/v, 500 mL total) was added benzyl bromide (29.7 mL, 249 mmol) under argon. A 50% suspension of NaH in mineral oil (15 g, 312.5 mmol) was added portionwise over 1 h. The resulting mixture was allowed to warm to room temperature with stirring. TLC showed no starting material after 2 h from the complete addition of NaH. The mixture was cooled to 0° C. and anhydrous methanol (20 mL) was cautiously added over 30 min. The resulting mixture was allowed to stir for an additional 30 min while warming to room temperature. H₂O (100 mL) was added and the mixture was poured into additional H₂O (900 mL) and extracted with diethyl ether (3 ×500 mL). The combined ether extracts were sequentially washed with H₂O and brine, dried over MgSO₄, filtered and concentrated to a yellow oil (ca. 80 g). This material was used without further purification.

(3) Preparation of
4-O-Benzyl-3,5-dipropionyl-D-galactal

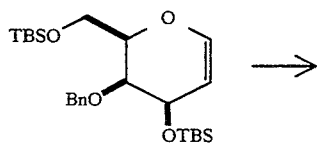

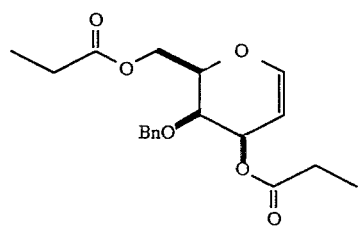

To a solution of the crude 4-O-Benzyl-3,5-di-O-tert-butyldimethylsilyl-D-galactal (ca. 80 g) in THF (200 mL) was slowly added a 1.0 M solution of tetrabutylammonium fluoride in THF (275 mL, 275 mmol). The resulting clear, orange solution was stirred at room temperature for 2 h, at which time TLC showed no remaining silyl ether. The mixture was concentrated by rotary evaporation and the residue was acylated directly.

The crude diol was dissolved in CH₂Cl₂ (500 mL) and the resulting stirred solution was cooled to 0° C. under argon. Triethylamine (104.5 mL, 750 mmol), N,N-dimethylaminopyridine (1.00 g), and propionic anhydride (48.1 mL) were sequentially added, the latter over ca. 15 min. The resulting solution was stirred at 0° C. for 30 min, then allowed to warm to room temperature. Additional triethylamine (33 mL) and propionic anhydride (15 mL) were added after 1 h, and after an additional 4.5 h the reaction mixture was washed with saturated aqueous NaHCO₃ (500 mL) and concentrated. The residue was suspended in diethyl ether (500 mL) and washed with saturated aqueous NaHCO₃ (3×500 mL), H₂O (2×500 mL), and brine (500 mL). The organic phase was dried over MgSO₄, filtered and concentrated. The residue was chromatographed (hexanes/ethyl acetate; 10:1 to 1:1) to afford the dipropionyl compound (ca. 60 g) and the monopropionyl by-product (3.4 g).

(4) Preparation of carboxylic acid (after: Ireland R. E. et al. J. Am. Chem. Soc. 110:854–860, 1988)

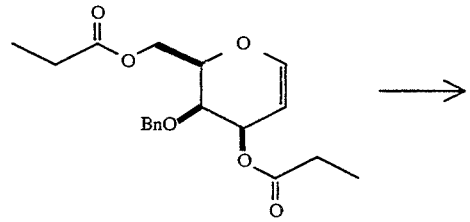

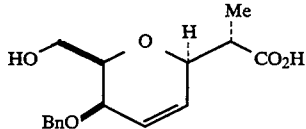

A solution of n-butyllithium in hexanes (63.4 mL of 2.5 M, 158.5 mmol) was added over ca. 10 min to a stirred solution of hexamethyldisilazane (35.9 mL, 172.2 mmol) in THF (320 mL) at −78° C. and under nitrogen. The resulting solution was stirred for 30 min at −78° C. before a solution of t-butyldimethylsilyl chloride (25.88 g, 172.5 mmol) in hexamethylphosphoramide (85 mL) was added over ca. 10 min. The resulting solution was stirred for 5 min before a solution of the dipropionate (20.00 g, 57.4 mmol) in THF (80 mL) was added dropwise over 25 min. The resulting solution was stirred at −78° C. for an additional 5 min, then allowed to slowly warm to ca 0° C. at which point it was poured into a separatory funnel containing a 0° C. mixture of ice-water (1 L) and petroleum ether (1.5 L, bp 40°–60° C.). The mixture was shaken and the organic phase was separated and washed with a 0° C. saturated aqueous solution of NaCl (500 mL), dried over Na2SO4, filtered, and concentrated at 25°–30° C. by rotary evaporation. The resulting yellow oil was dissolved in benzene (1 L) and the solution was heated at reflux for 6 h. After partial cooling, the solution was concentrated by rotary evaporation and the residue was dissolved in a mixture of THF and H2O (250 mL ea) and the resulting mixture was stirred at room temperature for 24 h. (This step can be omitted.) The THF was removed by rotary evaporation, a 1 M aqueous NaOH solution was added and the suspension was stirred for 3 h at room temperature. The mixture was extracted with diethyl ether (2×250 mL), and the aqueous phase was acidified to ca. pH 2.5 with aqueous 1 M HCl (200 mL). The resultant suspension was extracted with diethyl ether (3×250 mL) then with ethyl acetate (2×250 mL). The combined organic extracts were dried over Na2SO4, filtered, and concentrated to afford the crude carboxylic acid as a clear oil (18.74 g).

(5) Preparation of iodolactone

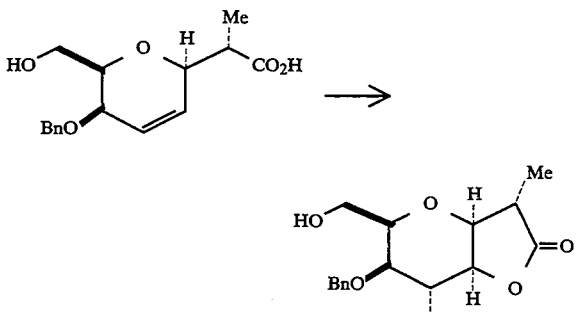

To a mechanically stirred solution of the crude carboxylate (30.12 g, ca. 86 mmol) in saturated aqueous NaHCO3 (1.00 L) at room temperature was added a solution of (59.25 g, 234 mmol) and KI (220.5 g, 1.329 mole) in H2O (375 mL). The resulting mixture was stirred at room temperature for 14 h, at which time TLC (hexanes/ethyl acetate; 1:1) showed no remaining starting material. A saturated aqueous solution of Na2S2O3 (400 mL) was added and the resulting mixture was extracted with ethyl acetate (4×500 mL). The combined organic extracts were dried over Na2SO4, filtered, and concentrated to a yellow oil. This crude iodolactone was used without further purification. In a separate experiment, a 6 h reaction time was sufficient. Note that the diastereometric methyl epimers may be chromatographically separated by silica gel chromatography (hexanes/ethyl acetate; 70:30) at this stage.

(6) Preparation of lactone

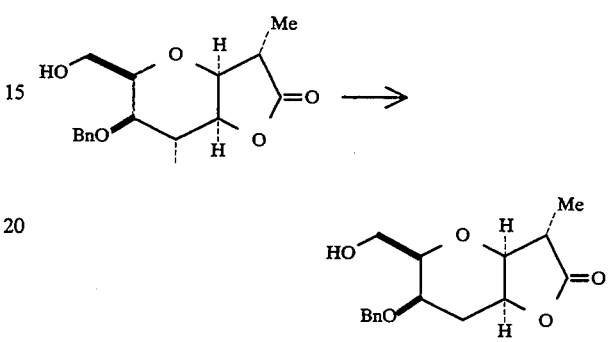

A stirred solution of the iodolactone, tri-n-butyltin hydride (28.0 mL, 104 mmol), and 2,2′-azobisisobutyronitrile ("AIBN", 100 mg) in benzene (500 mL) and under nitrogen was immersed in an 80° C. oil bath and maintained at reflux for 1 h. TLC (hexanes-/ethyl acetate; 1:1) showed no remaining starting material. The solution was cooled to room temperature and concentrated by rotary evaporation. The residue was chromatographed(toluene to ethyl acetate) to afford the lactone (23.30 g, 79.7 mmol, 92.2% yield from the dipropionate) as a colorless crystalline solid.

(7) Preparation of methyl acetals

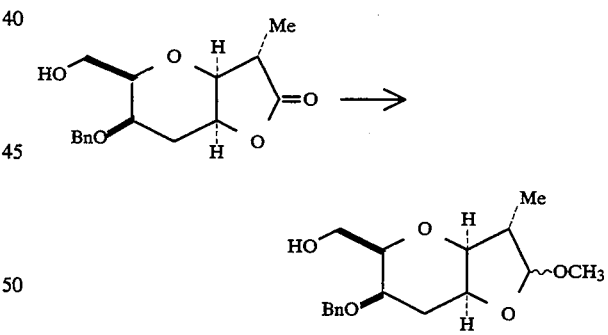

To a stirred solution of the lactone (23.25 g, 79 mmol) in THF (500 mL) at −78° C. and under nitrogen was added a 1 M solution of diisobutylaluminim hydride in hexane (258 mL, 258 mmol) by addition funnel over ca. 30 min. After an additional 1 h at −78° C., anhydrous methanol (90 mL) was cautiously added over 15 min, then saturated aqueous NH4Cl (90 mL) was added. The cooling bath was removed, diethyl ether (500 mL) was added, and the stirred mixture was allowed to warm to room temperature. The white gelatinous suspension was filtered through Celite and the residue was washed with ether (4×250 mL) and ethyl acetate (2×250 mL). The combined filtrate and washings were concentrated to a yellow oil. Dry toluene (500 mL) was added and the solution was reconcentrated by rotary evaporation to give the crude hemiacetal (18.46 g, ca. 0.8 mmol, 79% yield) as a clear, yellow oil.

The crude hemiacetal was dissolved in anhydrous methanol (1 L) and p-toluenesulfonic acid monohydrate (200 mg) was added. The resulting solution was stirred at room temperature for 14 h. TLC (hexanes/ethyl acetate/chloroform; 1:1:1) showed three products. Solid NaHCO₃ (2 g) was added and the mixture was concentrated by rotovap. The residue was applied directly to a silica gel column and eluted with hexanes-/ethyl acetate (1:1 to 0:1) to give a mixture of the two least polar products (13.98 g, 45.39 mmol, 72% yield) and the separate most polar product (4.65 g, 15.1 mmol, 24% yield). The least and most polar products (A and C) had the desired methyl configuration, while the intermediate $R_f$ product (B) had the undesired methyl configuration.

(8) Preparation of nitrile

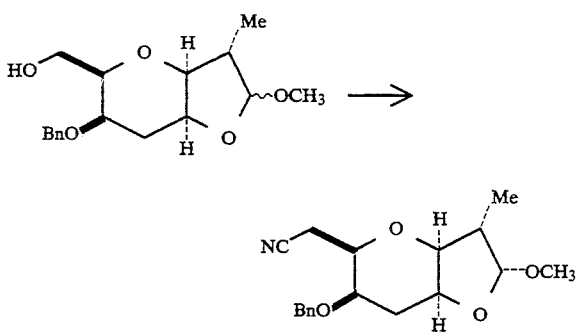

To a stirred solution of the alcohol (2.70 g, 8.77 mmol) in CH₂Cl₂ (200 mL) at −42° C. and under argon was added pyridine (1.56 mL, 19.3 mmol) followed by the dropwise addition over 5 min. of trifluoromethanesulfonic anhydride (2.22 mL, 13.15 mmol). The resulting mixture was stirred at −42° C. for 40 min, at which time TLC showed no starting material. Saturated aqueous NaHCO₃ (250 mL) and diethyl ether (400 mL) were added and the separated organic layer was washed with H₂O (2×400 mL) and brine (200 mL). Drying over Na₂SO₄, filtration, and rotary evaporation at near room temperature gave the crude triflate as a clear, yellow oil. This was concentrated further on a vacuum line for 10 min before being used directly in the next step.

The crude triflate was dissolved in N,N-dimethylformamide (40 mL) at 0° C. and under argon. To the stirred clear, pale yellow solution was added NaCN (1.718 g, 35.05 mmol). As the resulting mixture was allowed to warm to room temperature and stir over 40 min, it became dark. TLC at this point showed no remaining starting material. Saturated aqueous NaHCO₃ (200 mL) and diethyl ether (250 mL) were added and the separated organic phase was washed with H₂O (2×250 mL). The combined aqueous phases were extracted with diethyl ether (2×250 mL) and the combined organic fractions were washed with H₂O (2×250 mL) and brine (200 mL). Drying over Na₂SO₄, filtration, concentration, and silica gel chromatography gave the nitrile (1.211 g, 3.82 mmol, 44% yield over two steps) as a clear oil.

(9) Preparation of C38-primary alcohol

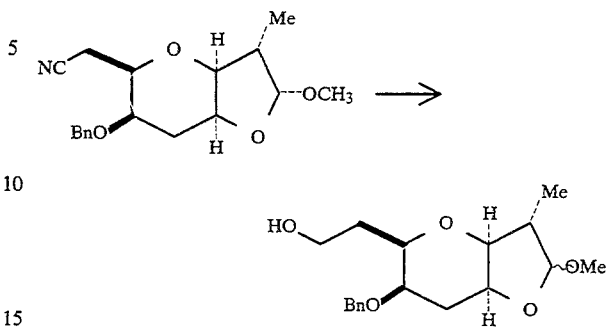

To a stirred solution of the nitrile (5.29 g, 16.7 mmol) in CH₂Cl₂ (250 mL) at −78° C. and under argon was added a 1 M solution of diisobutylaluminum hydride in hexane (25.0 mL, 25.0 mmol) over 15 min. The resulting solution was stirred at −78° C. for an additional 45 min before 1 M aqueous HCl (50 mL) was added. The cooling bath was removed and the resulting mixture was allowed to warm to 0° C. over 30 min. Diethyl ether (600 mL) was added and the mixture was washed with additional 1 M HCl then brine (50 mL ea.). The combined aqueous phases were extracted with ether (2×50 mL) and the combined organic fractions were dried over Na₂SO₄, filtered, and concentrated to a yellow oil. This material was used directly without further purification.

The crude aldehyde was dissolved in methanol (100 mL) and the stirred solution was cooled to 0° C. before NaBH₄ (1.00 g, 26.7 mmol) was added. The cooling bath was removed and after 10 min, the solvent was removed by rotary evaporation. The residue was suspended in H₂O (100 mL) and extracted with ethyl acetate (4×100 mL). The combined extracts were washed with brine (100 mL), dried over Na₂SO₄, filtered, concentrated and chromatographed to give the primary alcohol (4.384 g, 13.6 mmol, 81% yield over two steps) as a clear, colorless oil.

(10) Preparation of Diol

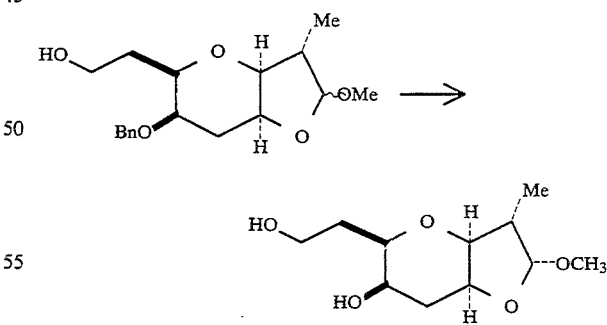

To a stirred solution of the primary alcohol thus prepared (5.27 g, 16.3 mmol) in methanol (200 mL) was added 10% Pd(OH)₂ on carbon (1 g). The rapidly stirred mixture was evacuated and refilled with H₂ four times, then stirred under 1 atom of H₂ for 13 h. TLC at this point showed no remaining benzyl ether. The mixture was filtered through Celite along with methanol washes, and the combined filtrate and washes were concentrated to a clear oil (3,685 g, 15.9 mmol, 97% yield).

(11) Preparation of Dimethyl acetal

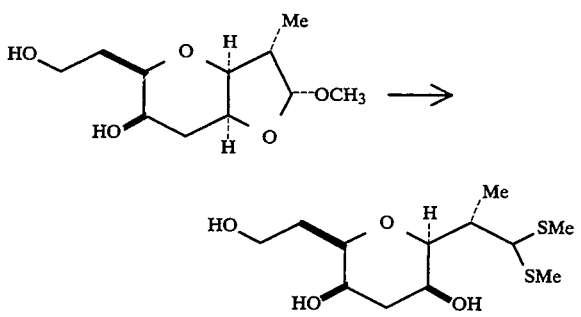

To a stirred solution of the methyl acetal (3.571 g, 15.37 mmol) in $CH_2Cl_2$ (60 mL) at $-78°$ C. and under argon was condenses methyl mercaptan (ca. 20 mL). The resulting solution was warmed to $0°$ C. and $BF_3·OEt_2$ (2 mL) was added. After stirring for 30 min. at $0°$ C., TLC (ethyl acetate) showed complete conversion to one higher $R_f$ spot. Saturated aqueous $NaHCO_3$ (50 mL) was cautiously added dropwise, $H_2O$ (50 mL) was added and the separated aqueous phase was extracted with $CH_2Cl_2$ ($4\times 150$ mL). The combined organic fractions were dried over anhydrous $K_2CO_3$, filtered, and concentrated to give the dithioacetal (4.206 g, 14.19 mmol, 92.3% yield) as a clear, colorless foam.

(12) Preparation of Trisilylether-dimethyl acetal

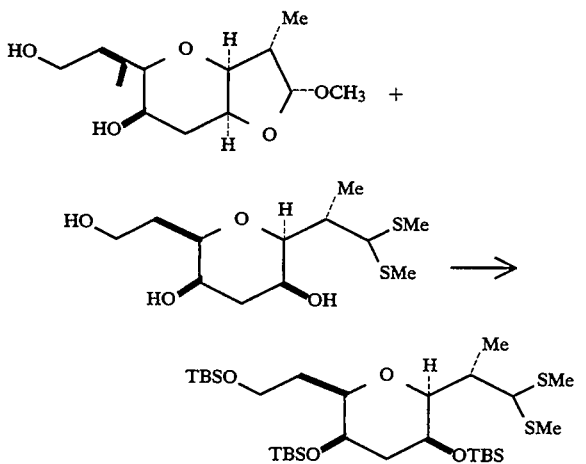

To a solution of the triol (1.26 g, 4.29 mmol) in methylene chloride (30 mL) at $0°$ C. was added triethylamine (4.5 mL, 32.2 mmol) followed by t-butyldimethylsilyltriflate (3.7 mL, 16.2 mmol). After 1 h, TLC analysis (hexanes/EtOAc; 20:1) showed the presence of starting material in addition to mono- , di- and trisyliated adducts. At this time, additional triethylamine (4.5 mL, 32.2 mmol) and t-butyldimethylsilyltriflate (3.7 mL, 16.2 mmol) was added to the reaction mixture and the resulting solution was stirred for 2 h. The reaction was then quenched by the addition of saturated aqueous sodium bicarbonate (50 mL). The resulting mixture was thoroughly extracted with ethyl acetate and the combined organics were washed with brine,m dried over sodium sulfate and concentrated in vacuo. The residual oil was purified by flash chromatography (hexanes/ethyl acetate; 50:1) to provide the trisilylether (2.2 g, 80% yield) as a light yellow oil.

(13) Preparation of aldehyde

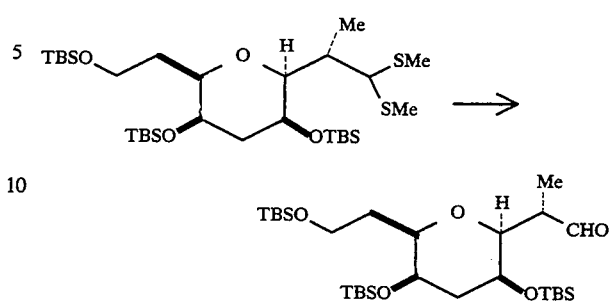

To a stirred solution of the dithioacetal (640 mg, 1.00 mmol) in acetone/$H_2O$ (9:1 v/v, 50 mL) at room temperature was added solid $NaHCO_3$ (252 mg, 1 mmol) followed by $I_2$ (254 mg, 1 mmol). After 30 min, the red reaction mixture was cooled to $0°$ C. and additional $NaHCO_3$ (252 mg) and $I_2$ (254 mg) were added. After an additional 30 min at $0°$ C., additional $NaHCO_3$ (252 mg) and $I_2$ (254 mg) were added and the mixture was allowed to warm to room temperature. After a total of 190 min, TLC showed no remaining starting material. The reaction mixture was poured into a separatory funnel containing ethyl acetate (50 mL) and 10% aqueous $Na_2S_2O_3$ (50 mL). After shaking and removal of the aqueous phase, the clear, colorless organic phase was washed with $H_2O$ and brine (50 mL ea.). The combined aqueous fractions were extracted with ethyl acetate ($2\times 50$ mL) and the combined organic fractions were dried over $Na_2SO_4$, filtered, and concentrated. Silica gel chromatography (hexanes/ethyl acetate; 10:1) of the residue gave the aldehyde (509 mg, 907 $\mu$mol, 91% yield) as a clear, colorless oil.

(14) Preparation of methyl acrylates

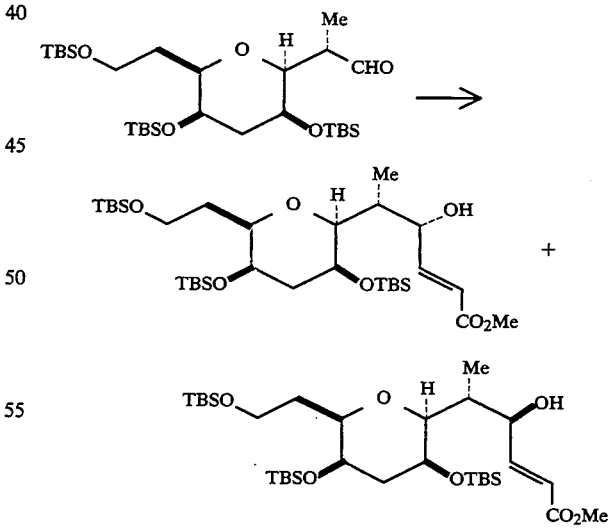

A mixture of the aldehyde (989 mg, 1.75 mmol) and trans-$\beta$-iodo-methylacrylate (1.85 g, 8.74 mmol) was dissolved in THF (10 mL) under nitrogen. To the stirred room temperature solution was added powdered $CrCl_2$ containing 1% $NiCl_2$ by mass (ca. 750 mg total). After 50 min, additional 1% $NiCl_2/CrCl_2$ (ca. 500 mg) was added to the pale green suspension, and the resulting mixture was stirred for 22 h at room temperature.

The reaction mixture was diluted with saturated aqueous NH₄Cl (20 mL) and extracted with diethyl ether (4×10 mL) then with ethyl acetate (2×10 mL). The combined extracts were concentrated by rotary evaporation, and the residue was suspended in ethyl acetate (20 mL) and washed with H₂O (2×20 mL) and brine (10 mL). The ethyl acetate solution was dried over Na₂SO₄, filtered, and concentrated. Repeated silica gel chromatography of the residue (ca. 150 g SiO₂, hexanes/tert-butylmethyl ether; 6:1; then hexanes/ethyl acetate/CHCl₃, 5:1:1) gave the two diastereomeric products (912 mg, 1.47 mmol, 84% combined yield).

(15) C30 inversion

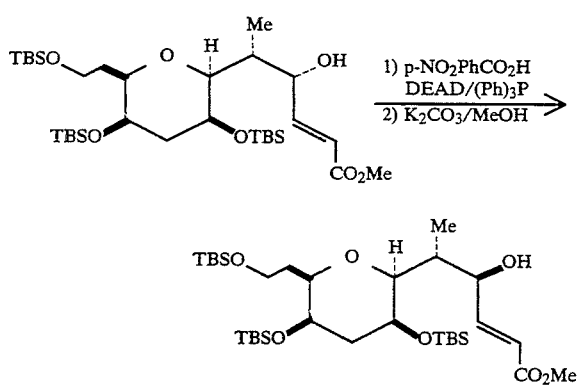

To a stirred solution of triphenylphosphine (373 mg, 1.42 mmol) and p-nitrobenzoic acid (238 mg, 1.42 mmol) in diethyl ether (20 mL) and toluene (10 mL) at room temperature was added a solution of the alcohol (441 mg, 712 μmol) in diethyl ether/toluene (2:1 v/v, 10 mL). To the resulting clear solution was added diethylazidodicarboxylate (224 μL, 1.42 mmol) dropwise. The resulting clear, yellow solution was stirred at room temperature for 4 h, at which time TLC (hexanes/ethyl acetate/chloroform; 5:1:1) showed no remaining starting material. Saturated aqueous NH₄Cl (30 mL) was added and the separated organic phase was washed with saturated aqueous NaHCO₃, H₂O, and brine (10 mL ea). The organic phase was dried over Na₂SO₄, filtered, concentrated and chromatographed to give the p-nitrobenzoate as a clear, yellow oil (522 mg).

To a stirred 0° C. solution of the p-nitrobenzoate (522 mg) in methanol (10 mL) was added K₂CO₃ (5 mg). After stirring for 30 min, TLC showed no remaining starting material. Acetic acid (5 μL) was added and the resulting mixture was concentrated and the residue chromatographed to give the alcohol (404 mg, 91% yield) as a colorless oil.

(16) Methoxyphenylmethylether Formation

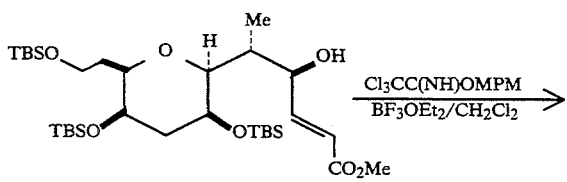

-continued

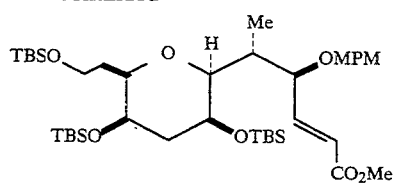

To a stirred 0° C. solution of the alcohol (755 mg, 1.22 mmol) and p-methoxybenzyltrichloroacetimidate (3.446 g, 12.2 mmol) in CH₂Cl₂ (120 mL) at 0° C. was added a 0.1 M solution of BF₃.OEt₂ in CH₂Cl₂ (50 μL). The resulting orange solution was stirred for 10 min, at which time TLC showed no remaining starting material. Saturated aqueous NaHCO₃ (40 mL) was added, and after vigorous mixing the separated organic phase was dried over Na₂SO₄, filtered, and concentrated. The residue was chromatographed on silica gel (hexanes/ethyl acetate; 5:1) to give the p-methoxybenzyl ether (866 mg, 1.17 mmol, 96% yield) as a clear oil.

(17) Preparation of Triol

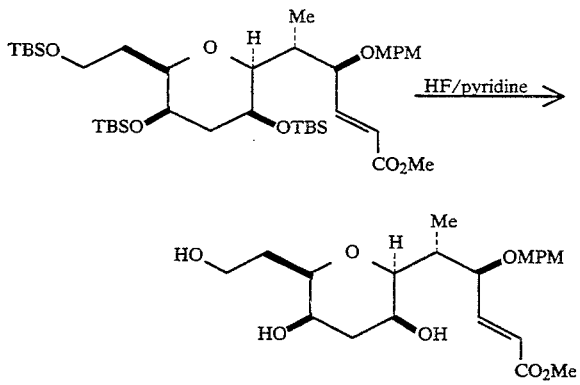

To a stirred solution of the p-methoxybenzyl ether (986 mg, 1.33 mmol) in acetonitrile (25 mL) at 0° C. was added pyridine (500 μL) followed by the HF.pyridine reagent (5.0 mL, Aldrich) over 1 min. After 75 min, TLC (ethyl acetate) showed essentially complete reaction. Saturated aqueous NaHCO₃ (200 mL) was cautiously added portionwise. The resulting mixture was extracted with ethyl acetate (3×200 mL), and the combined extracts were dried over Na₂SO₄, filtered and concentrated to give the crude triol (590 mg) as a clear, orange oil.

$[\alpha]_D^{RT} = +29.7°$ (c=3.4mg/mL, MeOH) .

(18) Preparation of acetonide

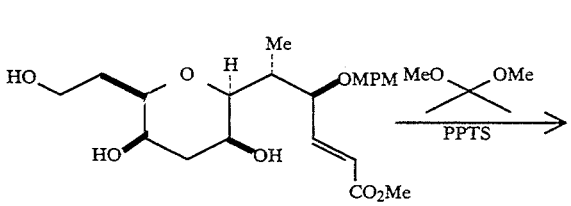

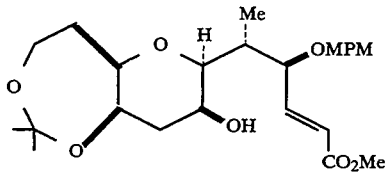

To a solution of the crude triol (560 mg, ca. 1.3 mmol) in CH2Cl2 (10 mL) at room temperature was added 2,2-dimethoxypropane (327 μL, 2.66 mmol) followed by pyridinium p-toluenesulfonate ("PPTS" 5 mg) After 1 h, additional 2,2-dimethoxypropane (327 μL, 2.66 mmol) was added. The reaction solution was allowed to stir for a total of 24 h, at which time TLC showed complete conversion to a single higher $R_f$ spot. The reaction mixture was washed with saturated aqueous NaHCO3, H2O, and brine (50 mL ea), and the resulting organic phase was dried over Na2SO4, filtered, concentrated and the residue chromatographed (ethyl acetate/hexanes/triethylamine; 1:1:0.001 to 1:0:0.001) to give the 7-membered acetonide (516 mg) as a colorless foam.

(19) Michael-type Addition

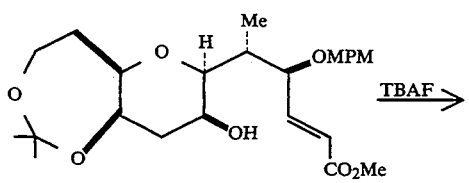

To a stirred 0° C. solution of the hydroxy acrylate (420 mg, 904 μmol) in THF (36 mL) and anhydrous methyl acetate (4 mL) was added a 1 M solution of tetrabutylammonium fluoride (TBAF) in the THF (9 mL, 9 mmol, Aldrich). Additional methyl acetate (4 mL) and TBAF solution (4.5 mL) were added after 1 h. After a total of 6 h at 0° C., the reaction solution was diluted with saturated aqueous NaHCO3 (175 mL) and brine (175 mL) and extracted with ethyl acetate (3×100 mL). The combined extracts were washed with H2O and brine (250 mL ea), dried over Na2SO4, filtered and concentrated. The residue was chromatographed on silica gel to give, in order of elution, starting material (57 mg), the desired cyclized product (336 mg, 723 μmol, 80% yield), and the undesired C29 epimeric cyclized product (16 mg) all as clear oils.

(20) Preparation of diol

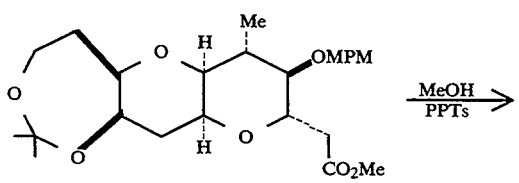

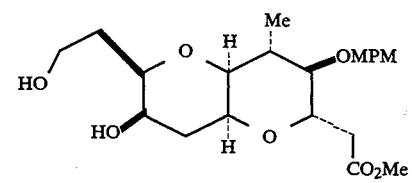

To a stirred solution of the acetonide (268 mg, 577 μmol) in methanol (10 mL) at room temperature was added pyridinium para-toluenesulfonate (5 mg). After 20 min of stirring at room temperature, TLC showed no remaining starting material. Solid NaHCO3 (50 mg) was added and the mixture was concentrated by rotary evaporation. The residue was filtered through a short pad of silica gel with ethyl acetate, and the filtrate was concentrated to give the crude diol (232 mg, 547 μmol, 95% yield) as a clear, colorless oil. This was used without further purification.

(21) Preparation of disilyl ether

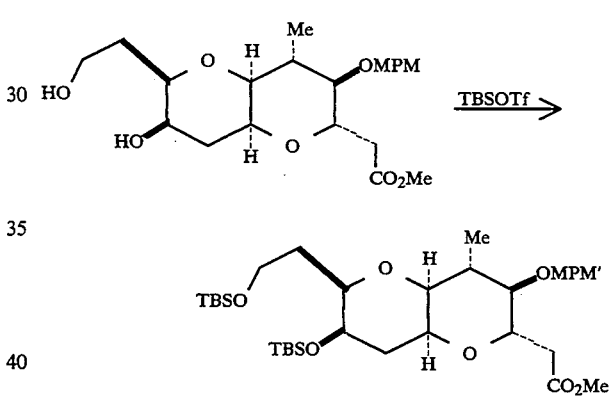

To a stirred solution of the diol (230 mg, 542 μmol) at 0° C. and under argon was added triethylamine (605 μL, 4.33 mmol) followed by t-butyldimethylsilyltrifluoromethane sulfonate (498 μL, 2.17 mmol). Additional triethylamine (303 μL) and tert-butyldimethylsilyltrifluoromethane sulfonate (249 μL) were added after 1 h. After 2 h total, the reaction mixture was washed with saturated aqueous NaHCO3, dried over Na2SO4, filtered, and concentrated. The residue was chromatographed on silica gel (hexanes/ethyl acetate; 5:1) to give the disilyl ether (308.8 mg, 473 μmol, 87% yield) as a clear, colorless oil.

(22) Preparation of disilyl alcohol

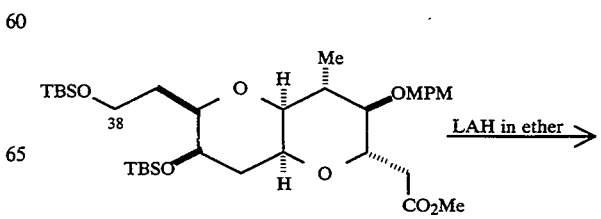

-continued

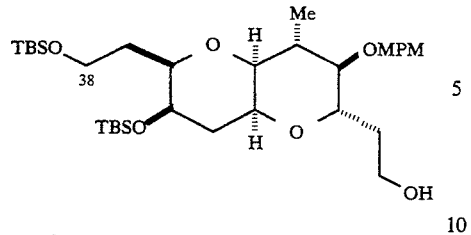

To a solution of ester (306 mg, 0.480 mmol) in ether (10 mL) at 0° C. was added a 1.6 M solution of lithium aluminum hydride (0.60 mL, 2 eq) in diethyl ether. After 5 min, an aqueous solution saturated with Rochelle's salt and NH4Cl was added and the resulting mixture was stirred vigorously until it formed two clear phases. The mixture was extracted with ethyl acetate (2×10 mL), and the combined extracts were dried over Na2SO4, filtered, and concentrated under reduced pressure. The residue was purified by silica gel column chromatography with hexanes/ethyl acetate/chloroform (5:1:1) to afford the alcohol (278 mg, 95.2% yield).

IR (film) 775 cm$^{-1}$ 835, 1251, 1472, 1514, 2930, 2956, 3453.

$^1$H NMR (CDCl3): δ0.47 (6 H, s), 0.53 (3 H, s), 0.80 (3 H, s), 0.89 (9 H, s, t-Bu), 0.90 (9 H, s, t-Bu), 1.15 (3 H, d, J=7.1 Hz), 1.60 (1 H, m), 1.76 (2 H, m), 1.82 (1 H, m), 1.93 (1 H, m), 2.08 (2 H, m), 2.98 (1 H, br s), 3.06 (1 H, m), 3.37 (1 H, t, J=4.2 Hz), 3.50 (1 H, m), 3.71 (2 H, m), 3.79 (1 H, m), 3.80 (3 H, s, -OMe), 4.13 (1 H, m), 4.45 (2 H, d, J=10.9 Hz), 4.56 (2 H, d, J=10.9 Hz), 6.87 (2 H, d, J=8.5 Hz), 7.24 (2 H, d, J=8.5 Hz).

HRMS (FAB) calcd for C33H60O7Si2+Na 647.3775, found 647.3763.

[α]$_D$−20.2° (C 0.99, MeOH).

(23) Preparation of disilyl aldehyde (compound 6)

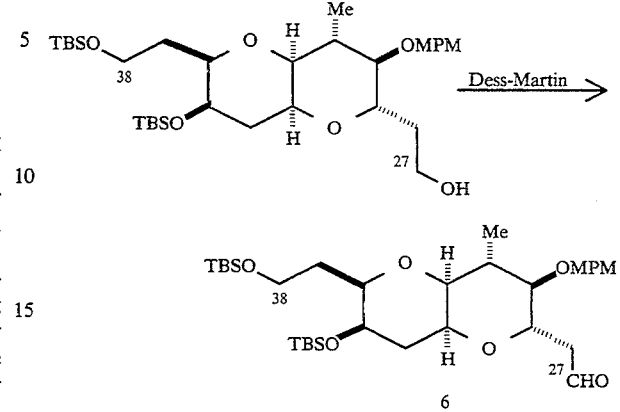

To a stirred solution of alcohol (100 mg, 0.164 mmol) in dichloromethane (5 mL) was added the Dess-Martin periodinane reagent (150 mg, 2.5 eq) at room temperature. After ca. 1 h, TLC showed no remaining starting material. The reaction mixture was diluted with diethyl ether (25 mL) and an aqueous solution of sodium thiosulfate and NaHCO3 (saturated) was added. The resulting mixture was stirred until two clear phases formed, then it was extracted with diethyl ether (2×15 mL). The combined extracts were dried over anhydrous Na2SO4, filtered, and concentrated. The residue was purified by silica gel column chromatography with 12% ethyl acetate in hexanes to give the aldehyde (92.5 mg, 92.8% yield).

Compound 7

Compound 7 was synthesized according to the following procedure.

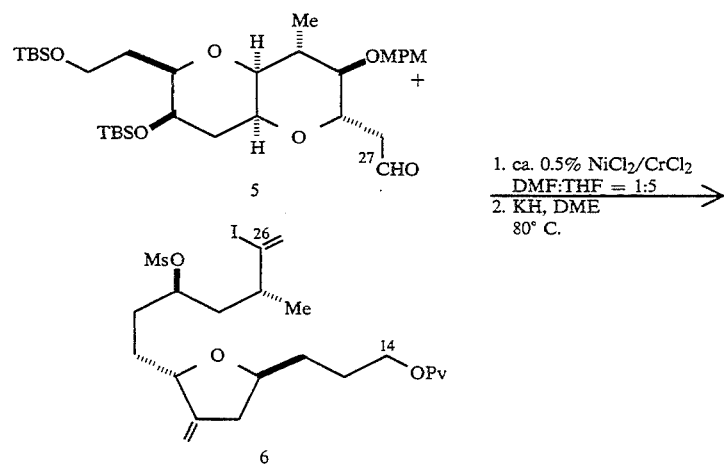

-continued

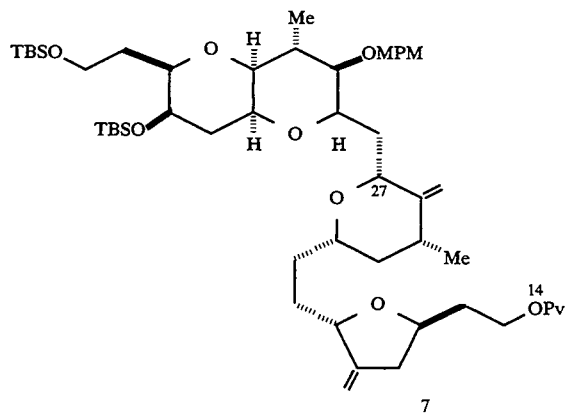

To a solution of aldehyde (102 mg, 0.168 mmol) and mesylate (141.6 mg, 0.255 mmol) in 17% (v/v) DMF in THF (2.08 mL) was added ca. 20 mg of 0.1% NiCl₂ in CrCl₂ and ca. 10 mg of 1% NiCl₂ in CrCl₂. The metal reagents were added in the same proportions four more times over 26 h. The reaction mixture was diluted with saturated aqueous NH₄Cl (8 mL), and extracted with ethyl acetate (3×10 mL). The combined organic layers were dried over anhydrous Na₂SO₄ and concentrated under reduced pressure. The crude residue was dried by azeotropic removal of water with benzene, and dried further under high vacuum. The residue was dissolved in 1,2-dimethoxyethane (25 mL) and a 35% by weight dispersion of KH (ca. 10 mg) in mineral oil was added. The reaction flask was immersed in an 80° C. oil bath for 2.5 min, then cooled to 0° C. in an ice-water bath. The reaction mixture was diluted with anhydrous ether (30 mL), filtered through a silica gel pad along with additional anhydrous ether (30 mL) washes. The filtrate was concentrated and the residue was purified by silica gel column chromatography with 12% ethyl acetate in hexanes to give the product (86 mg, 53% yield).

IR (film) 722 cm⁻¹ 835, 1040, 1250, 1463, 1514, 1755, 2854, 2926.

$[\alpha]_D$: −20° C. (C 3.3, MeOH).

HRMS (FAB) calcd for $C_{54l}H_{92}O_{10}Si_2$+Na 979.6124, found 979.6149.

¹H NMR (C₆D₆): δ0.04 (3 H, s), 0.10 (3 H, s), 0.11 (3 H, s), 0.14 (3 H, s), 0.97 (3 H, d, J=6.5 Hz), 1.00 (9 H, s), 1.02 (9 H, s), 1.11 (1 H, m), 1.16 (9 H, s), 1.26 (4 H, m), 1.51–1.90 (11 H, m), 1.98–2.20 (5 H, m), 2.27 (2 H, m), 2.39 (1 H, m), 2.45 (1 H, m), 3.23 (2 H, t, J=9.0 Hz), 3.31 (3 H, s), 3.53 (1 H, m), 3.68 (2 H, m), 3.75 (1 H, m), 3.86 (1 H, m), 3.93 (1 H, m), 4.02 (2 H, m), 4.19 (1 H, m), 4.31 (1 H, m), 4.44 (1 H, m), 4.54 (2 H, q, J=7.9 Hz), 4.83 (1 H, s), 4.86 (1 H, br d), 4.91 (1 H, br d), 5.14 (1 H, s), 6.80 (2 H, d, J=8.4 Hz), 7.28 (2 H, d, J=8.4 Hz).

To a solution of C₁₄-pivaloate (27.8 mg, 0.029 mmol) in anhydrous ether (2 mL) was added a 1.6 M solution of lithium aluminum hydride in diethyl ether (38 μL, 61 μmol) at 0° C. The reaction mixture was stirred for 5 min, diluted with EtOAc (4 mL), and an aqueous solution saturated with Rochelle's salt and NH₄Cl was added. The reaction mixture was stirred until it formed a clear aqueous layer. The organic layer was separated and the aqueous layer was extracted with EtOAc (2×4 mL). The combined organic layers were dried over Na₂SO₄ and concentrated under reduced pressure. The oily residue was purified by column chromatography with 50% hexanes in ethyl acetate to afford the C14 alcohol (25 mg, 98.5% yield).

Compound 8

Compound 8 was synthesized from diacetone glucose according to either of the two following procedures.

Example 1

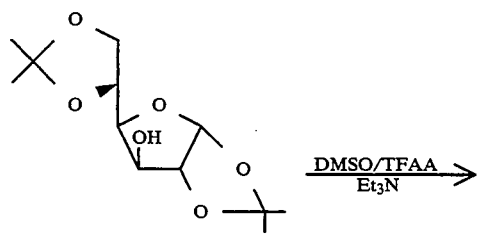

Diacetone D-glucose

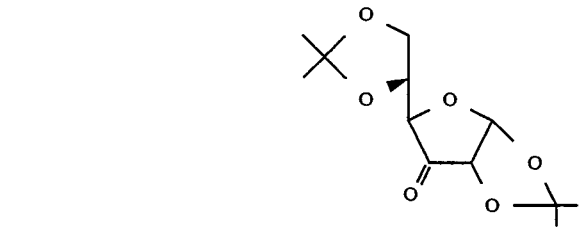

To a stirred solution of DMSO (10.65 mL, 150.1 mmol) in CH₂Cl₂ (300 mL) at −78° C. under argon was added trifluoroacetic anhydride ("TFAA" 16.00 mL, 113 3 mmol) dropwise. The resulting white suspension was stirred at −78° C. for 10 min before a solution of 1,2:5,6-di-O-isopropylidene-α-D-glucofuranose was slowly added by cannula. The resulting mixture was stirred at −78° C. for 1 h before triethylamine (30.4 mL, 218 mmol) was slowly added and the reaction mixture allowed to warm to room temperature. Saturated aqueous NH₄Cl (100 mL) was added and the organic phase was separated and washed with cold 1M aqueous HCl (2×100 mL), H₂O (100 mL), saturated aqueous NaHCO₃ (100 mL), H₂O (100 mL), and saturated aqueous NaCl (100 mL). The organic phase was dried, filtered and concentrated to give the crude ketone (1,2:5,6-di-O-isopropylidene-α-D-ribo-hexofuranos-3-ulose, 22.3 g) as a pale yellow oil. This material was used directly without further purification.

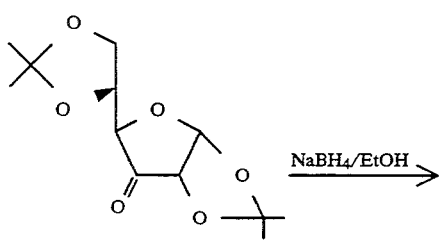

To a stirred solution of the crude ketone (22.3 g, ca. 75 mmol) in 95% ethanol (200 mL) at 0° C. was added NaBH4 (5.8 g, 154 mmol) portionwise over 20 min. After stirring an additional 10 min, TLC showed no remaining starting material. The solvent was removed by rotory evaporation and the residue was suspended in ethyl acetate (200 mL) and washed with H2O (2×100 mL) and saturated aqueous NaCl (100 mL). The organic phase was dried over Na2SO4, filtered, and concentrated to give the crude 1,2:5,6-di-O-isopropylidene-α-D-allofuranoseallose as a white solid (19.64 g, ca. 75 mmol, 98% yield over two steps).

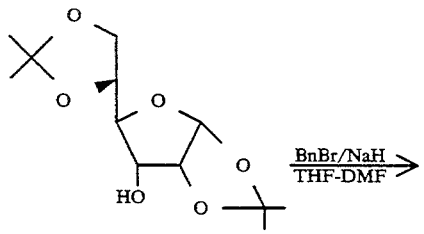

To a stirred solution of the allose diacetonide (19.6 g, ca. 75 mmol) in THF-DMF (500 mL, 4:1 v/v) at and under argon was added a 60% sodium hydride dispersion in mineral oil (6.0 g, 150 mmol) portionwise over 30 min. The resulting mixture was allowed to warm to room temperature over 1h, then it was recooled to 0° C. before benzyl bromide (25.7 g, 17.9 mL, 150 mmol) and t-n-butylammonium iodide (1.0 g) were added. The resulting mixture was allowed to warm to room temperature and stir for 16 h. The reaction mixture was cooled to 0° C. and anhydrous methanol (20 mL) was cautiously added over 30 min. The resulting mixture was allowed to warm to room temperature and stir for 1 h before the THF was removed by rotary evaporation. The residue was suspended in H2O (250 mL) and extracted with ethyl acetate (4×200 mL). The combined organic fractions were washed with H2O (500 mL) and brine (200 mL), dried over Na2SO4, filtered, and concentrated to give the crude 3-O-benzyl-1,2:5,6-di-O-isopropylidene-α-D-allofuranose as a clear, yellow oil (46.8 g). This material was used without further purification.

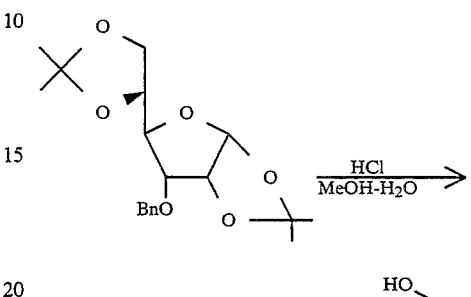

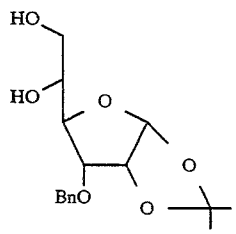

To a stirred mixture of the crude benzyl etherdiacetonide (46.8 g, ca. 75 mmol) in methanol-H2O (500 mL, 4:1 v/v) at 0° C. was added 1M aqueous HCl (50 mL). The resulting mixture was allowed to warm to room temperature and stir for 7.5 h, before being neutralized by the portionwise addition of solid NaHCO3 (20 g). The methanol was removed by rotary evaporation, and the resulting aqueous suspension was extracted with ethyl acetate (6×100 mL). The combined organic fractions were dried over Na2SO4, filtered, and concentrated to give the crude 3-O-Benzyl-1,2-O-isopropylidene-α-D-allofuranose as a clear, yellow oil. This material was used without further purification.

IR (film): 3420 cm−1, 3070, 3065, 3032, 2986, 2934, 2901, 1498, 1454, 1434, 1423, 1409, 1382, 1373, 1316, 1250, 1214, 1167, 1137, 1122, 1095, 1025, 697.

1H NMR (CDCl3): δ1.35 (3H, s), 1.58 (3H, s), 2.71 (1H, bt, J=5.7 Hz), 2.82 (1H, d, J=3.5 Hz), 3.67 (2H, m), 3.93 (1H, dd, J=4.3, 8.9 Hz), 4.00 (1H, m), 4.09 (1H, dd, J=3.2, 8.9 Hz), 4.55 (1H, d, J=11.4 Hz), 4.61 (1H, m), 4.77 (1H, d, J=11.4 Hz), 5.75 (1H, d, J=3.8 Hz), 7.25–7.50 (5H, m).

13C NMR (CDCl3): 26.56, 26.74, 63.05, 71.00, 72.13, 77.00, 77.33, 79.06, 104.21, 113.15, 128.20, 128.53, 136.85.

[α]D: +107.3° (C 6.65, CHCl3).

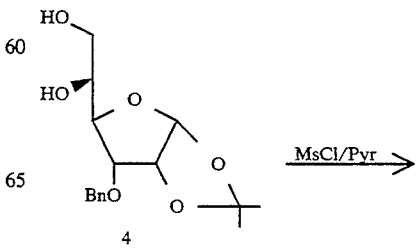

4

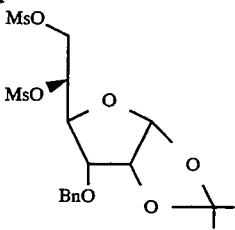

To a solution of the crude diol (ca. 75 mmol) in CH$_2$Cl$_2$ (300 mL) at 0° C. was added pyridine (90 mL, 1.1 mol) followed by methanesulfonyl chloride (30 mL, 388 mmol). The resulting solution was stirred at 0° C. for 1 h, then allowed to warm to room temperature and stir over an additional 3 h. Saturated aqueous NaHCO$_3$ (100 mL) was cautiously added portion-wise over 30 min. The organic phase was separated and washed with saturated aqueous NaHCO$_3$ (100 mL), 1 M aqueous HCl (2×100 mL), H$_2$O (100 mL), and brine (100 mL). The organic phase was dried over Na$_2$SO$_4$, filtered, and concentrated to an orange oil. The crude dimesylate, i.e., 3-O-Benzyl-1,2-O-isopropylidene-5,6-di-O-methanesulfonyl-α-D-allofuranose was as used without further purification. [After: Brimacombe, J. S.; Mofti, A. M.; Tucker, L. C. N. J. Chem. Soc. (C) 1971, 2911–2915; where they used the 3-O-methyl analogue.]

IR (film): 3032 cm$^{-1}$ 2970, 2939, 1455, 1361, 1247, 1241, 1219, 1176, 1135, 1122, 1104, 1093, 1027, 1010, 972, 924, 872, 831, 797, 746, 701, 665.

$^1$H NMR (CDCl$_3$): δ1.36 (3H, s), 1.58 (3H, s), 3.00 (3H, s), 3.03 (3H, s), 3.95 (1H, dd, J=4.3, 8.8 Hz), 4.20 (1H, dd, J=3.2, 8.8 Hz), 4.39 (2H, d, J=3.5 Hz), 4.56 (1H, d, J=11.2 Hz), 4.59 (1H, m), 4.75 (1H, d, J=11.2 Hz), 5.10 (1H, m), 5.75 (1H, d, J=3.6 Hz), 7.25–7.50 (5H, m).

$^{13}$C NMR (CDCl$_3$): 26.53, 26.83, 37.78, 38.74, 66.67, 72.29, 76.46, 77.11, 77.65, 104.34, 113.70, 128.41, 128.61.

[α]$_D$: +70.0° (C 2.86, CHCl$_3$).

To a solution of the crude dimesylate (ca. 75 mmol) in DMF (350 mL) was added powdered potassium acetate (20 g, 204 mmol). The resulting mixture was stirred at room temperature for 1 h, then it was heated to 145°–151° C. for 18 h. TLC showed no starting material, but three products. The mixture was cooled to near room temperature, diluted with H$_2$O (1.4 L), and extracted with ethyl acetate (4×500 mL). The combined extracts were washed with H$_2$O and brine, dried over Na$_2$SO$_4$, filtered, and concentrated to a dark brown oil. This material was dissolved in anhydrous methanol (250 mL), and the resulting solution was cooled to 0° C. while stirring under nitrogen. A freshly prepared solution of sodium (5 g) in methanol (200 mL) was slowly added via cannula, and the resulting solution was stirred at 0° C. for 1 h, then allowed to warm to room temperature with stirring over 3 h. Solid NH$_4$Cl (10 g) was added and the solvent was removed by rotary evaporation. The residue was suspended in ethyl acetate (100 mL) and filtered through a glass frit. The solid residue was washed with ethyl acetate (50 mL), and the combined filtrate and washes were concentrated to a brown oil. Silica gel chromatography (ethyl acetate-hexanes, 4:1 to 4:0) afforded the diol, i.e., 3-O-Benzyl-1,2-O-isopropylidene-α-L-talofuranose (6)$^6$, as a clear, colorless oil: 14.6 g (47.2 mmol, 63% yield over five steps).

IR (film): 3431 cm$^{-1}$ 3064, 3032, 2987, 2935, 1653, 1496, 1454, 1382, 1373, 1309, 1216, 1168, 1129, 1102, 1075, 1025, 921, 872, 739, 699, 666.

$^1$H NMR (CDCl$_3$): δ1.38 (3H, S), 1.59 (3H, S), 2.51 (2H, bs), 3.64–3.80 (3H, m), 3.93 (1H, dd, J=4.3, 8.9 Hz), 4.05 (1H, dd, J=2.2, 9.0 Hz), 4.53 (1H, m), 4.58 (1H, d, J=11.7 Hz), 4.76 (1H, d, J=11.7 Hz), 5.73 (1H, d, J=3.6 Hz), 7.25–7.50 (5H, m).

$^{13}$C NMR (CDCl$_3$): δ26.55, 26.84, 64.84, 69.85, 72.33, 77.18, 77.68, 79.75, 104.41, 113.13, 127.94, 128.36, 137.25.

[α]$_D$: +93.1° (C 9.99, CHCl$_3$).

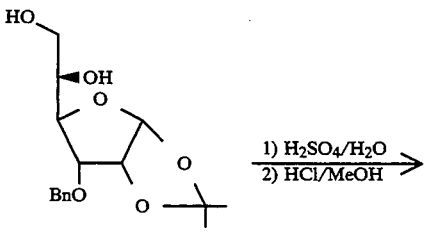

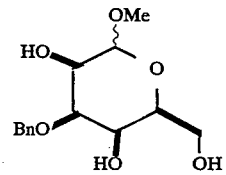

A stirred solution of the acetonide (14.6 g, 47.2 mmol) in 0.25 M aqueous H$_2$SO$_4$ (500 mL) was heated at 60° C. for 1 h, then allowed to cool to room temperature with stirring over an additional 3 h. The solution was carefully neutralized with portion-wise additions of solid BaCO$_3$ (12.33 g, 62.5 mmol). The suspension was filtered through a fritted glass funnel along with H$_2$O washes. The combined filtrate and washes were concentrated by rotovap to a syrup which was dried further on a vacuum line overnight to give 12.7 g (ca. 47.2 mmol) of crude L-3-O-benzyltalose.

To a solution of the L-3-O-benzyltalose (11.7 g, 43.5 mmol) in anhydrous methanol (250 mL) was cautiously added acetyl chloride (3.0 mL, 34.6 mmol) dropwise. The resulting solution was heated at reflux for 72 h, then cooled to room temperature. Solid NaHCO$_3$ (5 g) was added and the solvent was removed by rotary evaporation. The residue was suspended in ethyl acetate (250 mL) and filtered. The solids were washed with

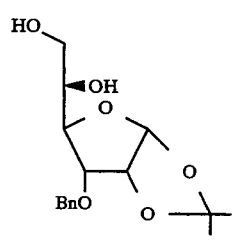

additional ethyl acetate, and the combined washes and filtrate were concentrated to give L-talopyranosides as an orange oil: 10.87 g (38.4 mmol, 81% yield).

Lit.: α-D-methyl-talopyranoside: $[\alpha]_D{:}^{24}+98°$ (C 1.3, H₂O). β-D-methyl-talopyranoside: $[\alpha]D{:}^{24}+28.5°$ (c 1.5, H₂O). See Angyal, S. J.; Bodkin, C. L.; Parrish, F. W. Aust. J. Chem. 28:1541–1549, 1975.

Lit.: α-D-methyl-talopyranoside: $[\alpha]_D{:}$ +105° (H₂O). See Gorin, P. A. J. Can. J. Chem. 38:641–651, 1960.

Lit.: α-D-methyl-talopyranoside: $[\alpha]_D{:}$ +106.5° (c 0.97, H₂O). See Evans, M. E. et al. Carb. Res. 54:105–114, 1977.

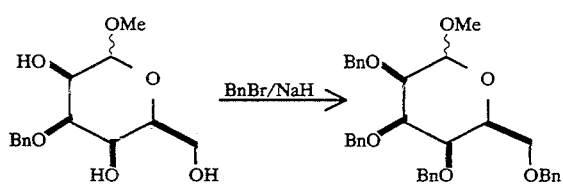

To a stirred solution of the crude methyl talosides (23.8 g, 84 mmol) in DMF (250 mL) at 0° C. under argon was added sodium hydride (15.2 g of a 60% dispersion in mineral oil, 380 mmol) portionwise over 30 min. The resulting mixture was allowed to warm to room temperature with stirring over 1 h, then it was recooled to 0° C. Benzyl bromide (38 mL, 318 mmol) was added dropwise over 20 min, and after an additional 20 min, tetra-n-butyl ammonium iodide (TBAI, 2 g) was added. The mixture was stirred at 0° C. for 30 min, then allowed to warm to room temperature and stir for 18 h. TLC at this point showed remaining starting material. The mixture was re-cooled to 0° C., and additional sodium hydride (5.1 g of 60 % dispersion, 128 mmol), benzyl bromide (12.7 mL, 106 mmol), and TBAI (2 g) were added sequentially. The mixture was again allowed to warm to room temperature and stir for 6 h. After a total of 24 h reaction time, the reaction mixture was cooled to 0° C., anhydrous methanol (20 mL) was cautiously added, and the mixture stirred for 1 h. The reaction mixture was then diluted with H₂O (1 L) and extracted with diethyl ether (4×500 mL). The combined organic extracts were washed with H₂O and brine (500 mL ea.), dried over Na₂SO₄, filtered and concentrated. Silica gel chromatography of the residue gave α,β-L-methyl-2,3,4,6-tetra-O-benzyltalopyranosides as a clear oil: 44.31 g (80 mmol, 95% yield).

IR (CCl₄): 3064 cm⁻¹ 3030, 2897, 1497, 1454, 1360, 1134, 1101, 1028, 735, 697,

¹H NMR (CDCl₃): δ3.34 (3H, s), 3.71–3.76 (4H, m), 3.91 (1H, bs), 3.93 (1H, m), 4.49 (1H, J=11.8 Hz), 4.52 (2H, s), 4.56 (1H, d, J=11.8 Hz), 4.75 (2H, d, J=11.7 Hz), 4.87 (1H, d, J=1.5 Hz), 4.88 (1H, d, J=11.7 Hz), 4.97 (1H, d, J=11.7 Hz), 7.20–7.50 (20H, m).

¹³C NMR (CDCl₃): 55.94 ppm, 69.57, 70.61, 71.04, 73.07, 73.28, 73.52, 73.70, 74.18, 100.23, 127.14, 127.24, 127.36, 127.45, 127.58, 127.75, 128.03, 128.14, 128.19, 128.32, 138.24, 138.36, 138.70, 139.06.

$[\alpha]_D$: −24.8° (c 0.81, CHCl₃).

Lit.: (α-D-anologue) 1HNMR (CDCl₃) 4.79 (J₁,₂ 1.8 Hz, H1), 5.08 (H2), 5.25 (H4), 4.22 (H5), 4.22 (H6), 3.42 (OCH₃), 2.00, 2.08, 2.16. See Banaszek, A. et al. Pol. J. Chem. 2029–2039, 1979.

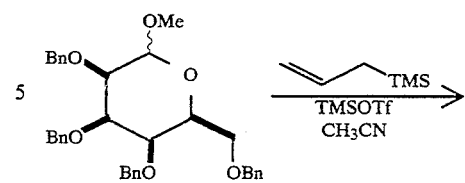

To a stirred solution of the methyl taloside (20.00 g, 36.1 mmol) in acetonitrile (220 mL) at 0° C. under argon was added allyltrimethylsilane (23 mL, 145 mmol) followed by trimethylsilyl trifluoromethanesulfonate (7.1 mL, 37 mmol) dropwise. The resulting clear, yellow solution was stirred at 0° C. for 10 min, then allowed to warm to room temperature. After 1 h, TLC showed no remaining starting material. The reaction mixture was diluted with diethyl ether (400 mL) and washed with saturated aqueous NaHCO₃ (2×200 mL), H₂O (200 mL), and brine (200 mL). The organic phase was dried over Na₂SO₄, filtered, concentrated, and the residue was chromatographed (SiO₂, hexanes-ethyle acetate; 7:1) to give the major allylated product as a clear, colorless oil: 16,207 g (28.74 mmol, 80% yield).

IR (film): 3064 cm⁻¹ 3030, 2898, 1453, 1093, 1074, 913, 734, 696.

¹H NMR (CDCl₃): δ2.23 (1H, dt, J=7.7, 14.3 Hz), 2.59 (1H, m), 3.13 (1H, dd, J=2.6, 9.4 Hz), 3.60 (1H, dd, J=2.3, 6.3 Hz), 3.81 (1H, dd, J=1.8, 12.0 Hz), 3.92 (1H, m), 4.12 (1H, t, J=2.3 Hz), 4.17 (1H, dd, J=8.8, 12.0 Hz), 4.31 (1H, m), 4.37 (1H, d, J=11.5 Hz), 4.51 (1H, d, J=11.5 Hz), 4.53–4.61 (4H, m), 4.69–4.77 (2H, m), 5.06 (1H, dd, J=0.8, 10.1 Hz), 5.10 (1H, dd, J=0.8, 17.2 Hz), 5.89 (1H, m), 7.20–7.42 (20H, m).

¹³C NMR (CDCl₃): 35.72 ppm, 66.31, 67.33, 71.00, 71.28, 73.11, 73.91, 75.06, 76.87, 78.01, 116.90, 127.32, 127.40, 127.71, 127.75, 127.78, 127.84, 128.15, 128.28, 128.39, 128.42, 134.89, 137.82, 138.01, 138.72, 138.81.

$[\alpha]_D$: −24.8° (C 0.81, CHCl₃).

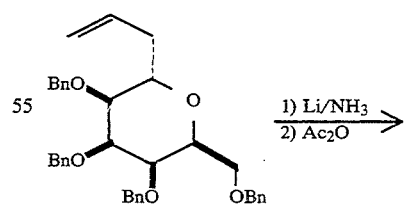

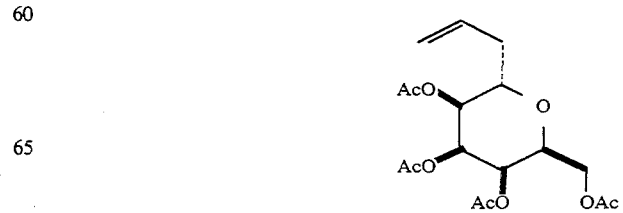

Lithium (4.5 g, 652 mmol) was added piece-wise to liquid NH₃ (1 L) at −78° C. under nitrogen. The resulting blue solution was allowed to stir for 20 min before a solution of the allylated product (32.07 g, 56.86 mmol) in THF (200 mL) was added via cannula. The resulting blue solution was stirred at −78° C. for 30 min, then anhydrous methanol was added dropwise just until the blue color disappeared. The cooling bath was removed and the solvents were evaporated under a stream of nitrogen. The residue was suspended in CH₂Cl₂ (500 mL) and cooled to 0° C. under nitrogen. To the stirred suspension were added triethylamine (178.4 mL, 1.28 mmol), acetic anhydride (60 mL, 640 mmol), and N,N-dimethylaminopyridine (1.2 g). The resulting mixture was allowed to warm to room temperature and stir for 12 h. The mixture was washed with H₂O (2×500 mL) and brine (500 mL), dried over Na₂SO₄, filtered, and concentrated. The residue was chromatographed on silica gel to give the alkene tetraacetate as a clear oil: 19.34 g (51.9 mmol, 91.4% yield over two steps).

IR (film): 3077 cm⁻¹ 2941, 1749, 1643, 1497, 1434, 1372, 1226, 1116, 1074, 1043, 915.

¹H NMR (CDCl₃): δ2.03 (3H, s), 2.06 (3H, s), 2.07 (3H, s), 2.10 (3H, s), 2.27–2.38 (2H, m), 4.02 (1H, ddd, J=4.5, 7.5, 7.5 Hz), 4.10 (1H, dd, J=3.6, 12.2 Hz), 4.20 (1H, ddd, J=3.6, 5.1, 8.9 Hz), 4.63 (1H, dd, J=8.9, 12.2 Hz), 4.84 (1H, dd, J=3.2, 7.3 Hz), 5.08 (1H, t, J=1.3 Hz), 5.11 (1H, m), 5.19 (1H, dd, J=3.2, 5.1 Hz), 5.45 (1H, t, J=3.2 Hz), 5.78 (1H, m).

¹³C NMR (CDCl₃): 20.60 ppm, 20.78, 34.75, 60.47, 66.54, 67.27, 68.82, 69.32, 70.61, 117.79, 132.96, 169.47, 169.58, 169.73, 170.77.

MS (FAB): 374 amu (rel. intensity 12%), 373 (M++H, 91), 331 (9), 313 (38), 271 (7), 154 (76), 136 (78), 91 (98), 77 (100), 63 (70), 51 (97).

[α]_D²: −31.6 (C 0.93, CHCl₃).

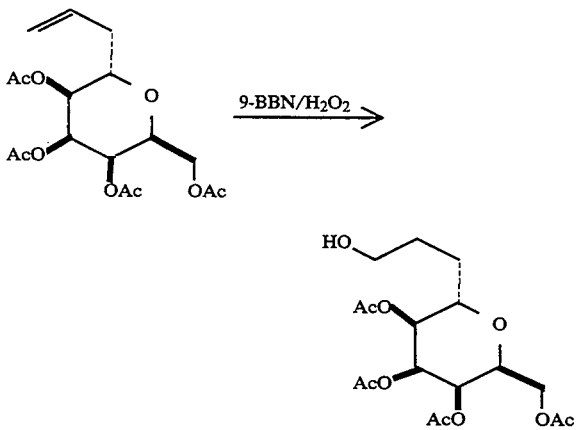

To a stirred solution of the alkene tetraacetate (20.30 g, 54.55 mol) in THF (200 mL) at 0° C. and under argon was added a 0.5 M solution of 9-borabicyclo[3-3.1]nonane ("9-BBN") in THF (185 mL, 92.5 mmol). The resulting solution was allowed to warm to room temperature and stir for 3 h, at which point TLC showed no starting material. The reaction mixture was cooled to 0° C. and 10% aqueous NaOH (25 mL) and 30% aqueous H₂O₂ (25 mL) were sequentially added dropwise. The resulting mixture was stirred at 0° C. for 1.5 h before saturated aqueous NH₄Cl (1 L) was added and the mixture was extacted with ethyl acetate (500 mL). The ethyl acetate phase was washed with saturated aqueous NaCl (500 mL), and the combined aqueous phases were extracted with additional ethyl acetate (2×500 mL). The combined ethyl acetate extracts were dried over Na₂SO₄, filtered, concentrated, and chromatographed (SiO₂, hexanes-ethyl acetate, 1:2→0:1) to give the primary alcohol 11 (16.102 g, 41.25 mmol, 75.6% yield) as a clear oil.

IR (film): 3510 cm⁻¹ 3020, 3012, 2940, 2877, 1745, 1451, 1432, 1402, 1371, 1227, 1118, 1091, 1046, 991, 965.

¹H NMR (CDCl₃): δ1.53–1.72 (4H, m), 2.05 (3H, s), 2.08 (6H, s), 2.10 (3H, s), 3.63 (2H, bt), 3.96 (1H, m), 4.08 (1H, dd, J=3.6, 12.2 Hz), 4.19 (1H, ddd, J=3.6, 5.0, 8.9 Hz), 4.63 (1H, dd, J=8.9, 12.2 Hz), 4.80 (1H, dd, J=3.2, 7.1 Hz), 5.19 (1H, dd, J=3.2, 5.0 Hz), 5.43 (1H, t, J=3.2 Hz).

¹³C NMR (CDCl₃): 20.53 ppm, 20.67, 20.71, 26.87, 28.40, 60.53, 62.26, 66.64, 67.33, 69.57, 69.99, 70.59, 169.41, 169.65, 170.74.

[α]_D: −39.6° (C 9.59, CHCl₃).

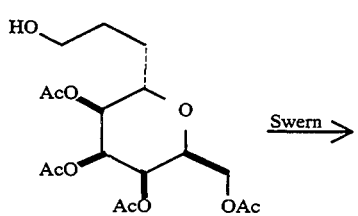

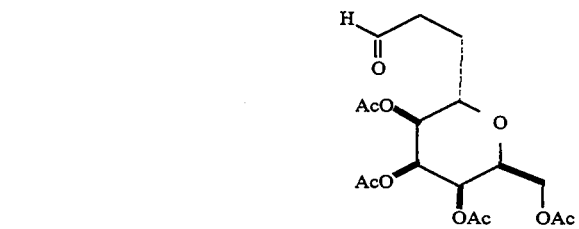

To a solution of oxallyl chloride (483 μL, 5.55 mmol) in CH₂Cl₂ (20 mL) at −78° C. under argon was added DMSO (872 μL, 12.3 mmol) dropwise. The resulting solution was stirred for 15 min at −78° C. before a solution of the primary alcohol (1.015 g, 2.60 mmol) in CH₂Cl₂ (10 mL) was slowly added. After 1 h at −78° C., triethylamine (2.00 mL) was added and the resulting clear solution was stirred for an additional 20 min at −78° C. then allowed to warm to room temperature. The reaction mixture was washed with saturated aqueous NH₄Cl (30 mL), diluted with diethyl ether (50 mL), and washed with H₂O and saturated aqueous NaCl (50 mL ea.). The combined aqueous washes were back-extracted with diethyl ether (50 mL) and the combined organic phases were dried over Na₂SO₄, filtered, and concentrated to give a crude aidehyde. This material was used directly without further purification.

IR (film): 2939 cm⁻¹ 2851, 2731, 1748, 1653, 1617, 1576, 1559, 1539, 1521, 1507, 1436, 1372, 1227, 1119, 1074, 1044, 964, 908.

¹H NMR (CDCl₃): δ1.68 (1H, m), 1.87 (1H, m), 1.95 (3, s), 1.97 (3H, s), 2.00 (3H, s), 2.03 (3H, s), 2.45 (2H, m), 3.86 (1H, m), 3.93 (1H, dd, J=3.1, 13.1 Hz), 4.09 (1H, m) 4.68 (1H, dd, J=9.7, 13.1 Hz), 4.69 (1H, m), 5.08 (1H, dd, J=3.1, 5.8 Hz), 5.41 (1H, dd, J=3.0, 3.1 Hz), 9.67 (1H, s).

¹³C NMR (CDCl₃): 20.52 ppm, 20.60, 20.75, 23.32, 39.37, 59.96, 66.75, 67.52, 67.92, 69.53, 71.31, 169.24, 169.50, 169.61, 170.75, 201.16.

[α]$_D$: −45.9° (C 8.37, CHCl₃).

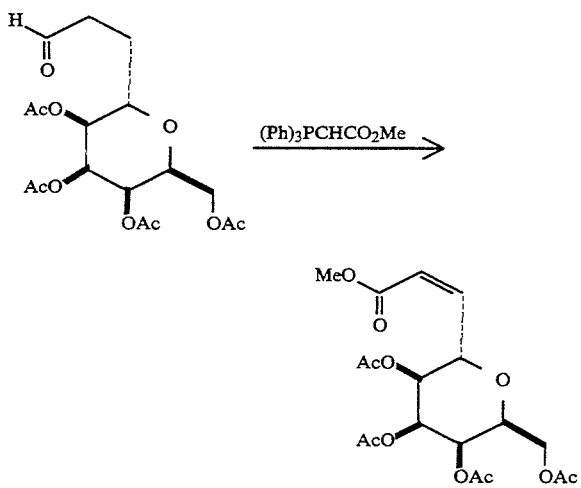

To a stirred solution of the aldehyde (16.23 g, mmol) in CH₂Cl₂ (400 mL) at 0° C. was added carbomethoxymethylene triphenylphosphorane (27.8 g, 83.2 mmol). The resulting solution was allowed to stir at 0° C. for ca. 1 h, then allowed to warm to room temperature and stir for 18.5 h before being washed with saturated aqueous NH₄Cl, H₂O, and saturated aqueous NaCl (200 mL ea.). The organic phase was dried over Na₂SO₄, filtered, and concentrated, and the residue was chromatographed (SiO₂, hexanes-ethyl acetate, 2:1) to give the methyl ester (16.524 g, 37.138 mmol, 88% yield) as a clear oil.

IR (film): 2953 cm⁻¹ 1750, 1658, 1437, 1373, 1321, 1225, 1170, 1117, 1073, 1042, 908.

¹H NMR (CDCl₃): δ1.59–1.73 (2H, m), 2.03 (3H, s), 2.06 (3H:, S), 2.08 (3H, s), 2.11 (3H, s), 2.23–2.40 (2H, m), 3.72 (3H, s), 3.91 (1H, ddd, J=3.3, 7.8, 9.5 Hz), 4.11 (1H, dd, J=3.1, 12.3 Hz), 4.18 (1H, ddd, J=3.1, 5.4, 9.2 Hz), 4.63 (1H, dd, J=9.2, 12.3 Hz), 4.77 (1H, dd, J=3.1, 7.8 Hz), 5.18 (1H, dd, J=3.1, 5.4 Hz), 5.46 (1H, t, J=3.1 Hz), 5.85 (1H, d, J=15.6 Hz), 6.94 (1H, m).

¹³C NMR (CDCl₃): 20.57 ppm, 20.65, 20.78, 27.58, 28.93, 51.39, 60.31, 66.68, 67.43, 68.26, 69.47, 70.94, 121.79, 147.87, 166.85, 169.35, 169.54, 169.67, 170.71.

[α]$_D$: −23.7° (C 1.41 CHCl₃).

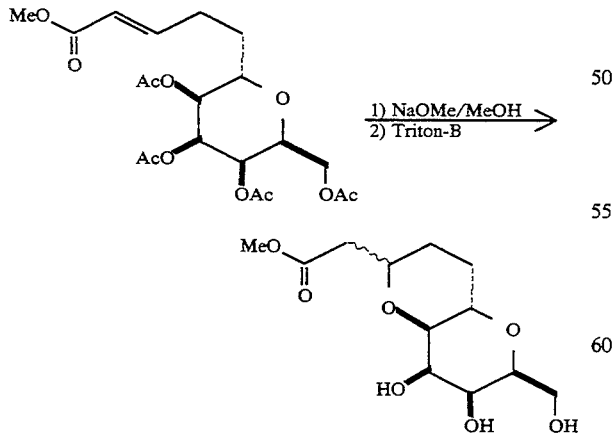

Anhydrous methyl acetate (25 mL) was added to a solution of sodium methoxide in methanol (prepared from 8 g Na in 500 mL MeOH), and the resulting solution was added via cannula to a stirred solution of the methyl ester (16.2 g, 36.4 mmol) in methanol (250 mL) and methyl acetate (25 mL) at 0° C. The resulting solution was stirred at 0° C. for 30 min before a solution of triton B (10 mL of a 40% solution in methanol) was added. The resulting yellow solution was stirred at 0° C. for 1 h, then allowed to warm to room temperature with stirring. Solid NH₄Cl (20 g) was added and the solvents were removed in vacuo. The residue was suspended in methyl acetate (200 mL) and filtered through a fritted glass funnel. The solids were washed with additional methyl acetate (2×100 mL) and the combined filtrate and washes were concentrated to a yellow oil. Column chromatography on SiO₂ (methyl acetate to ethyl acetate/methanol, 10:1) gave the triol as a clear, pale yellow oil and an approximate 2.5:1 mixture of C3 diastereomers: 7.26 g (26.3 mmol, 72% yield).

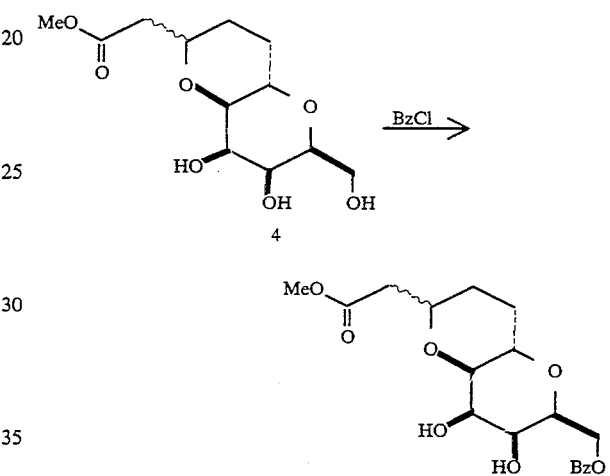

To a stirred solution of the triol (17 mg, 61 μmol) in CH₂Cl₂ (1.0 mL) at 0° C. and under N₂ was added pyridine (100 μL, 1.24 mmol) followed by benzoyl chloride (50 μL, 431 μmol). TLC (ethyl acetate) showed no remaining starting material after 10 min. The reaction solution was diluted with diethyl ether (2 mL) and washed with H₂O and brine. The organic phase was dried over Na₂SO₄, filtered, concentrated, and chromatographed (SiO₂, ethyl acetate) to give the primary benzoate as a clear oil: 21 mg (55 μmol, 89% yield).

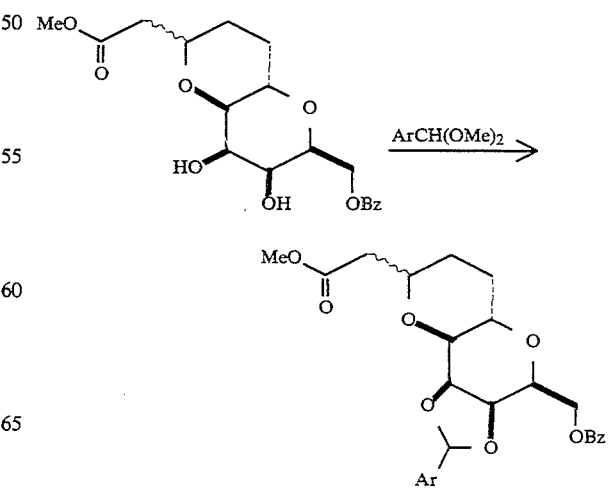

To a stirred solution of the benzoate (436 mg, 1.13 μmol) in benzene (20 mL) at room temperature was added anisaldehyde dimethyl acetal (412 mL, 2.4 mmol) followed by pyridinium p-toluene sulfonate (10 mg). The resulting solution was stirred at room temperature. After 30 min, crushed 4Å molecular sieves (0.5 g) were added and stirring was continued. Solid NaHCO₃ (1 g) was added after 6 h and the resulting mixture was filtered through Celite with diethyl ether washes. The filtrate was concentrated and the residue was purified by SiO₂ column chromatography (1:1 hexanes/ethyl acetate to 10:1 ethyl acetate/methanol) to give the anisylidene (356 mg, 714 μmol, 62% yield) as a clear, colorless oil, and recovered diol (157 mg, 415 μmol).

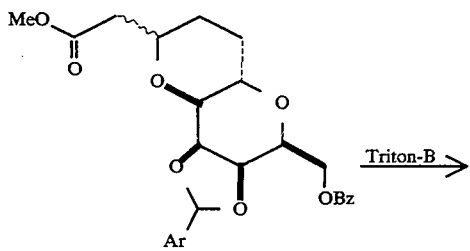

To a stirred solution of the C3 epimers of the anisylidene (356 mg, 714 μmol) in benzene (30 mL) at room temperature was added methyl acetate (100 μL) followed by a solution of triton B (30 μL of 40% solution in methanol). The resultant pale yellow solution was stirred at room temperature for 10 min before saturated aqueous NH₄Cl (20 mL) and diethyl ether (30 mL) were added. The separated organic phase was washed with H₂O and brine (30 mL ea), dried over Na₂SO₄, filtered, and concentrated to an oil: ¹H NMR analysis of the crude product showed only one isomer. This material was used without further purification.

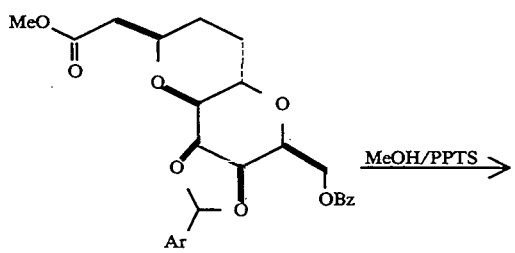

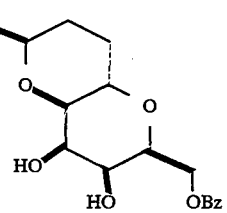

To a stirred solution of the anisylidine (3.37 g, 6.74 mmol) in methanol (150 mL) at room temperature was added pyridinium p-toluene sulfonate (PPTS, 50 mg). After stirring at room temperature for 13 h, additional PPTS (50 mg) was added. After a total of 15 h, TLC (1:1:1 hexanes/ethyl acetate/CHCl₃) showed no remaining starting material. Solid NaHCO₃ (250 mg) and pyridine (250 μL) were added and the mixture was concentrated. The residue was suspended in ethyl acetate, filtered, concentrated, and chromatographed (SiO₂, ethyl acetate) to give the diol as a colorless oil: 2.53 g (6.65 mmol, 99% yield).

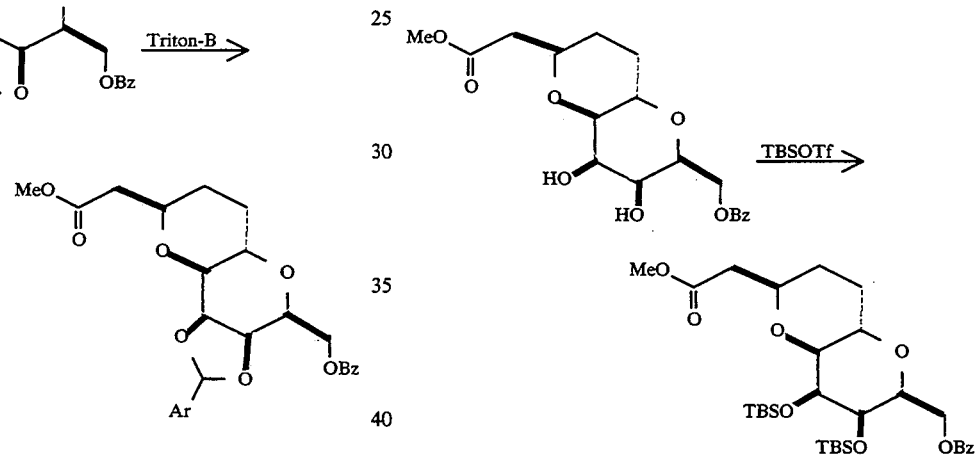

To a stirred solution of the diol (2.53 g, 6.65 mmol) in CH₂Cl₂ (200 mL) at 0° C. and under argon was added triethylamine (7.81 mL, 56 mmol), followed by t-butyldimethylsilyl trifluoromethane sulfonate (6.43 mL, 28 mmol). The resulting solution was allowed to slowly warm to room temperature and stir over 14 h. TLC (3:1:1 hexanes/ethyl acetate/CHCl₃) showed one spot (R_f ca. 0.85). The reaction solution was diluted with diethyl ether (300 mL) and washed with saturated aqueous NH₄Cl, H₂O, and brine (200 mL ea.). The organic phase was dried over Na₂SO₄, filtered and concentrated. Silica gel column chromatography (8:1 hexanes/ethyl acetate) and vacuum-line concentration overnight gave the disilyl ether as a clear, colorless oil: 3.897 g (6.41 mmol, 96% yield).

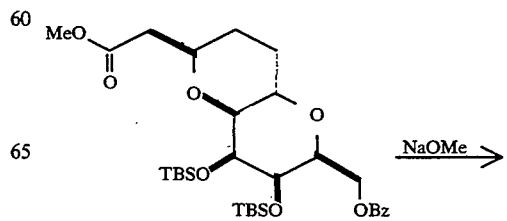

-continued

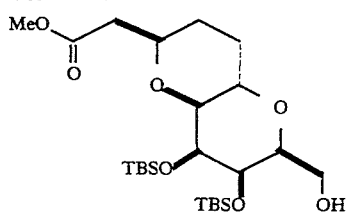

To a stirred solution of the disilyl ether (3.89 g, 6.40 mmol) in methanol (150 mL) and methyl acetate (6 mL) at 0° C. was added a solution of sodium methoxide in methanol (prepared from 0.5 g Na in 50 mL methanol). After stirring at 0° C. for 30 min, the cooling bath was removed, and after a total of 280 min, TLC (3:1:1 hexanes/ethyl acetate/CHCl₃) showed no remaining starting material. Solid NH₄Cl (2 g) was added and the resulting white suspension was concentrated in vacuo. The residue was suspended in diethyl ether (200 mL) and washed with H₂O (2×100 mL) and brine (100 mL). The organic phase was dried over Na₂SO₄, filtered and concentrated. Silica gel column chromatography (4:1 hexanes/ethyl acetate) gave the primary alcohol as a crystalline solid: 2.906 g (5.74 mmol, 90% yield).

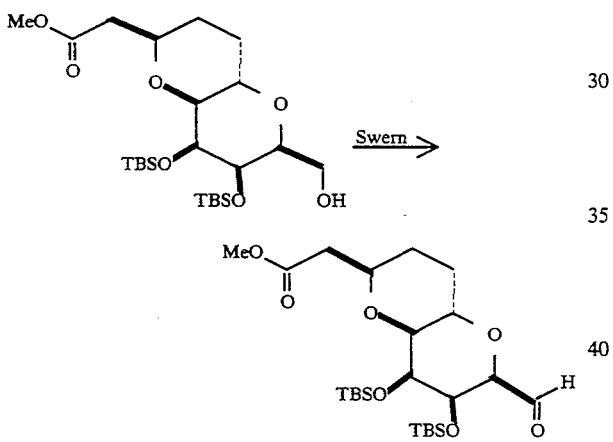

Dimethyl sulfoxide (963 μl, 13.58 mmol) was added dropwise to a stirred solution of oxallyl chloride (533 μL, 6.126 mmol) in CH₂Cl₂ (20 mL) at −78° C. under argon. After stirring for 20 min at −78° C. a solution of the alcohol (636 mg, 1.26 mmol) in CH₂Cl₂ (10.0 mL) was slowly After stirring for 1 h at −78° C., triethylamine (2.21 mL.) was added, the cooling bath was removed, and thee mixture stirred for an additional 30 min. Saturated aqueous NH₄Cl (50 ml.) and diethyl ether (50 mL) were added, and the separated organic phase was washed with H₂O (2×50 mL) and brine (50 mL). Drying over Na₂SO₄, filtration, concentration, and silica gel column chromatography gave the aldehyde as a clear oil: 551 mg (1.10 mmol, 87% yield).

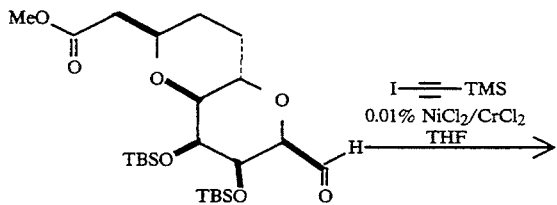

-continued

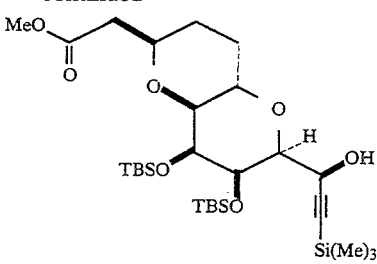

To a stirred solution of the aldehyde (551 mg, 1.10 mmol) and iodotrimethylsilyacetylene (reference to 1-iodo-2-trimethylsilylethyne: Commercon, A. et al. Tetrahedron. 36:1215, 1980) (1.25 g, 5.6 mmol) in THF under N₂ and at room temperature was added 0.01% NiCl₂/CrCl₂ (ca. 200 mg). Additional 0.01% NiCl₂/CrCl₂ was added after 10.5 h (ca. 100 mg), and after 16 h (ca. 250 mg). After 31 h total, the reaction mixture was diluted with saturated aqueous NH₄Cl (5 mL) and extracted wtih ethyl acetate (4×4 mL). The combined ethyl acetate extracts were washed with H₂O (2×10 mL) and brine (5 mL), dried over Na₂SO₄, filtered, and concnetrated, Silica gel column chromatography (8:1 hexanes/ethyl acetate) gave the higher R_f major C11 diastereomer (529 mg, 882 μmol, 80%) and a mixture (109 mg) of the lower R_f undesired C11 diastereomer and starting aidehyde. ¹H NMR of the crude product mixture before chromatography showed an approximate 10:1 ratio of diastereomeric adducts.

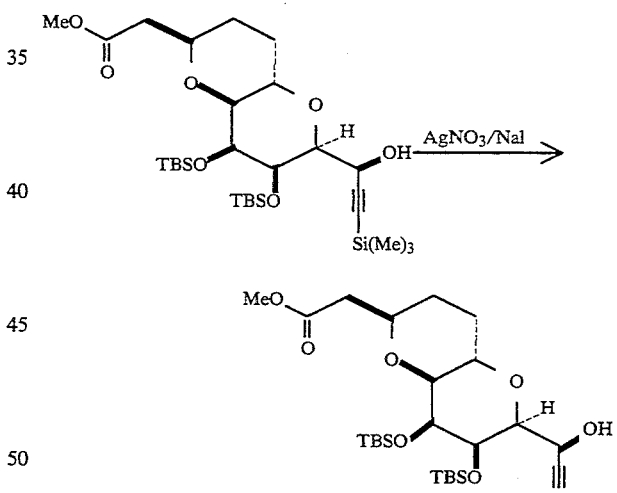

To a stirred solution of the major C11 diastereomer (241 mg, 402 μmol) in ethanol-H₂O (5 mL, 4:1 v/v) at 0° C. was added a solution of AgNO₃ (138 mg, 804 μmol) in ethanol-H₂O (0.5 mL, 3:1 v/v). The resulting suspension was stirred at 0° C. for 20 min (TLC showed no starting material). A solution of NaI (240 mg, 1.608 mmol) in H₂O (0.5 mL) was added dropwise, and stirring was continued at 0° C. for an additional 30 min. The yellow suspension was diluted with diethyl ether (10 mL) and filtered through celite along with additional ether washes (4×10 mL). The combined filtrate and washes were concentrated by rotary evaporation to an aqueous suspension that was extracted with diethyl ether (4×5 mL). The combined organic extract was dried over Na₂SO₄, filtered, and concentrated. Silica gel column chromatography gave the de-trimethylsilylated product (206 mg, 390 μmol, 97% yield) as a crystalline solid. [After: Tetrahedron Lett. 28:3923–3926, 1987.]

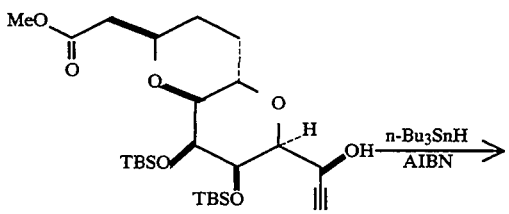

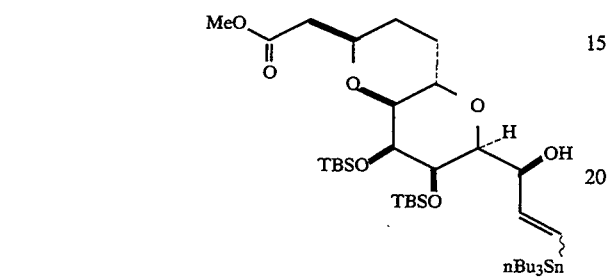

A stirred solution of the de-trimethylsilylated product (52 mg, 98.5 μmol), tri-n-butylstannane (134 μL, mol), and AIBN (2 mg) in de-gassed toluene under argon was placed in a pre-heated oil bath at 80° C. After 30 min, TLC (5:1:1 hexanes/ethyl acetate/CHCl₃) showed complete conversion to two higher R$_f$ spots. The reaction mixture was cooled to room temperature, concentrated in vacuo, and the residue was chromatographed (SiO₂, hexanes→hexanes-ethyl acetate, 5:1) to give the higher R$_f$ E-vinyl stannane (58 mg, 71 μmol, 72% yield) and lower R$_f$ Z-vinyl stannane (18 mg, 22 μmol, 22% yield) as clear, colorless oils.

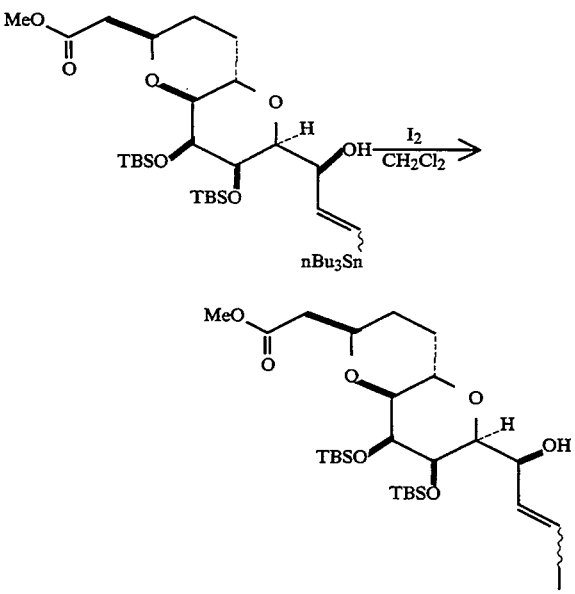

To a stirred solution of the E-vinyl stannane (58 mg, 70 μmol) in CH₂Cl₂ (1 mL) at 0° C. was added a solution of I₂ in CH₂Cl₂ (ca. 360 μL, of a 50 mg I₂/mL CH₂Cl₂ solution, ca. 71 μmol) just until the reaction mixture remained faint pink. After an additional 30 min at 0° C., TLC (5:1:1 hexanes/ethyl acetate/CHCl₃) showed complete conversion to a higher R$_f$ spot. The solution was diluted with diethyl ether (2 mL) and washed with aqueous 10% Na₂S₂O₃ (2×1 mL), H₂O, and brine (1 mL ea). The organic phase was dried over Na₂SO₄, filtered, and concentrated. Purification of the residue by silica gel column chromatography (hexanes-ethyl acetate, 4:1) gave the E-vinyl iodide as a clear, colorless oil: 46 mg (70 μmol, ca. 100% yield).

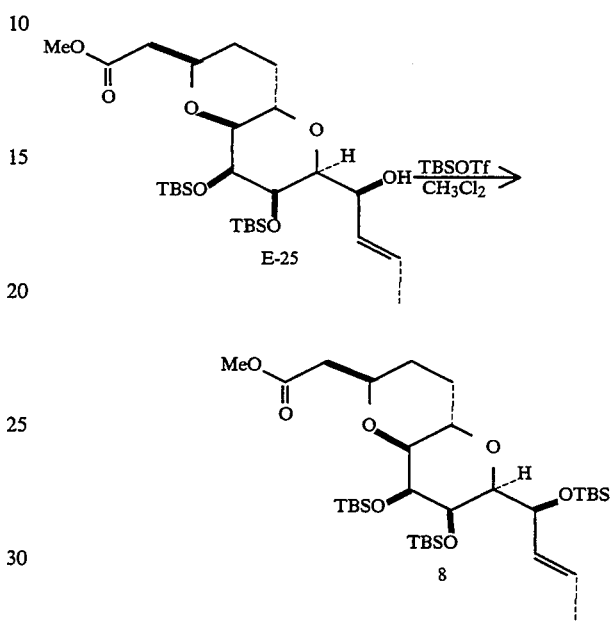

To a stirred solution of the E-vinyl iodide (42 mg, 64 μmol) in CH₂Cl₂ (2 mL) at 0° C. under argon was added triethylamine (179 μL, 1.28 mmol) followed by t-butyldimethylsilyltrifluoromethane sulfonate (149 μL, 640 mmol). The cooling bath was removed and the reaction mixture was allowed to warm to room temperature and stir for 3 h. TLC (5:1:1 hexanes/ethyl acetate/CHCl₃) at this time showed no remaining starting material. The reaction solution was diluted with diethyl ether (5 mL) and washed with saturated aqueous NaHCO₃ (5 mL), H₂O (5 mL), and brine (2 mL). Drying over Na₂SO₄, filtration, concentration, and SiO₂ column chromatography (hexanes-ethyl acetate, 5:1) gave compound 8 as a clear, colorless oil: 49 mg, 63 mmol, 99% yield).

Example 2

A more concise synthesis as depicted in Scheme 3 of compound 8 was developed.

Scheme 3

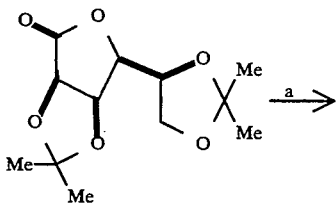

61

-continued
Scheme 3

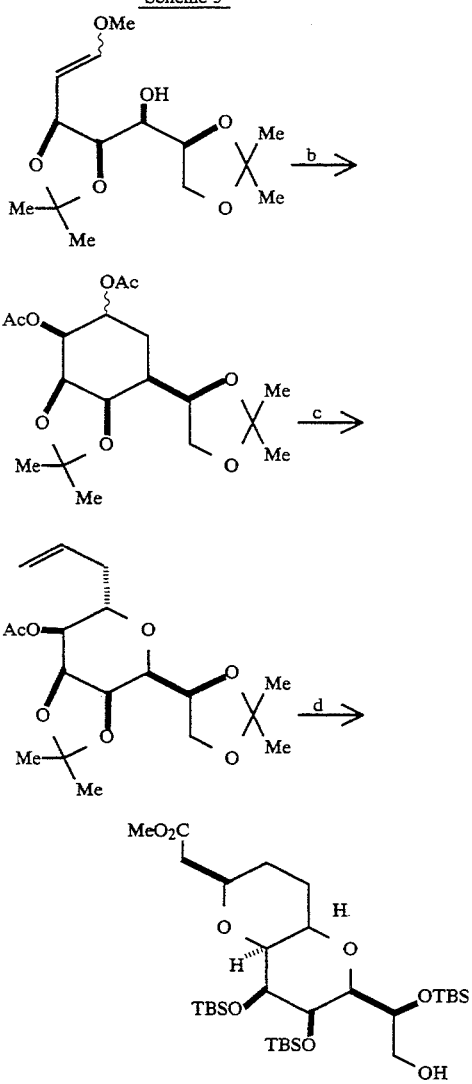

Reagents and reaction conditions. a. DI-BAL/CH$_2$Cl$_2$/−78° C. 2. MeOCH$_2$PPh$_3$Cl/t-BuOK/t-BuOH-THF/50° C. h 1 OsO$_4$/N,N'-his(mesitylmethyl)-1,2-diaminoethane/−78° C. 2. Ac$_2$O/py/RT. c. CH$_2$=CHCH$_2$TMS/TMSOTf/MeCN/0° C. d. Follow the reaction conditions given on pages 73–81.

Compound 9

Compound 9 was prepared from compounds 7 and 8, as follows.

(1) Conversion of C14 alcohol to C14 aldehyde

To a stirred solution of the C14 alcohol derived from compound 7 (46.9 mg, 53.8 μmole) in CH$_2$Cl$_2$ (4 mL) was added solid NaHCO$_3$ (50 mg) followed by the Dess-Martin periodinane reagent (45.6 mg, 108 μmole). TLC (3:1:1 hexanes/ethyl acetate/CHCl$_3$) showed no remaining starting material after 1 h. The reaction mixture was diluted with diethyl ether (16 mL) and washed for 20 min with an aqueous solution saturated with NaHCO$_3$ and containing 10% Na$_2$S$_2$O$_3$ by wt. The separated organic phase was washed with additional aqueous NaHCO$_3$/Na$_2$S$_2$O$_3$ for 10 min, H$_2$O, and brine (10 mL ea.). The organic phase was dried over Na$_2$SO$_4$, filtered, and concentrated. The residue was filtered through a short pad of SiO$_2$ (1:1 hexanes/ethyl acetate), and the filtrate was concentrated to afford the C27 epimeric C14 aldehydes (44 mg, 51 μmole, 94% yield) as a clear colorless oil.

(2) C.13–C.14 coupling

To a stirred solution of the C14 aldehyde (62 mg, 71 μmole) and the vinyl iodide (compound 8) (179 mg, 214 μmole) in DMF (2 mL) under nitrogen was added 0.1% NiCl$_2$/CrCl$_2$ (ca. 200 mg). The resulting green mixture was stirred at room temperature. After 14 h, TLC (3:11 hexanes/ethyl acetate/CHCl$_3$) showed approximately 50% conversion, and additional 0.1% NiCl$_2$/CrCl$_2$ (ca. 200 mg) was added. After a total of 39 h, TLC showed no remaining aldehyde. The reaction mixture was diluted with saturated aqueous NH$_4$Cl (12 mL) and H$_2$O (2 mL) and extracted with ethyl acetate (4×10 mL), dried over Na$_2$SO$_4$, filtered, and concentrated. The residue was purified by SiO$_2$ column chromatography to give the coupled allylic alcohol (79.1 mg, 56.7 μmole, 80% yield) as a colorless foam.

(3) Preparation of of pentasilyl enone (C.14 ketone)

To a stirred solution of the coupled allylic alcohols (59 mg, 39 μmole) in CH$_2$Cl$_2$ (2 mL) was added solid NaHCO$_3$ (50 mg) followed by the Dess-Martin periodinane reagent (66 mg, 156 μmole). Additional Dess-Martin reagent (33 mg, 78 μmole) and NaHCO$_3$ (50 mg) were added after 1 h. After a total of 90 min, the reaction mixture was diluted with diethyl ether (16 mL) and washed with an aqueous solution saturated with NaHCO$_3$ and containing 10% Na$_2$S$_2$O$_3$ by wt for 20 min. The separated organic phase was washed with additional aqueous NaHCO$_3$/Na$_2$S$_2$O$_3$ for 10 min, H$_2$O, and brine (10 mL ea.). The organic phase was dried over Na$_2$So$_4$, filtered, and concentrated. The residue was purified by SiO$_2$ column chromatography followed by PTLC (5:1:1 hexanes/ethyl acetate/CHCl$_3$) to give the enone (50.1 mg, 33 μmole 85% yield) as a clear, colorless oil.

(4) Removal of C.41 p-methoxyphenylmethyl (MPM) to produce C30 alcohol

To a stirred mixture of the C30 MPM ether (mixture of C27 epimers) (50 mg, 33 μmole) in CH$_2$Cl$_2$ (2.00 mL), aqueous phosphate buffer (200 μL, pH 7.00), and tert-butanol (20 μL) was added DDQ (15.0 mg, 66 μmole). The reaction flask containing the resulting mixture was immersed in a sonication bath (H$_2$O, room temperature) and sonicated for 30 sec, removed from the bath and stirred without sonication for approximately 3–5 min, and sonicated for an additional 30 sec. At this point, HPTLC (3:1:1 hexanes/ethyl acetate/tert-butyl methyl ether) showed approximately 50% conversion. Additional DDQ (15.0 mg) was added and the mixture was sonicated for an additional 2×30 sec and stirred for a total of 20 min. TLC showed no remaining starting material. The reaction mixture was washed with saturated aqueous NaHCO$_3$ (2×2 mL) and H$_2$O (2 mL). The combined aqueous phases were extracted with CH$_2$Cl$_2$ (2×1 mL), and the combined organic fractions were washed with brine (2 mL), dried over Na$_2$SO$_4$, filtered, and concentrated. The residue was purified by PTLC 3:1:1 hexanes/ethyl acetate/tert-butyl methyl ether, 2 elutions) to afford the higher R$_f$ desired C27 epimer (31.4 mg, 22.5 μmole, 66% yield), and the lower R$_f$ undesired C27 epimer (6.4 mg, 14% yield) as clear, colorless oils.

(5) Preparation of C30 C.1 carboxylic acid

To a stirred solution of the methyl ester (the higher R$_f$ C27 epimer, 31.4 mg, 22.5 μmole) in THF (2.00 mL) at room temperature was added 1M aqueous LiOH (666 μL). The resulting mixture was stirred at room temperature for 36 h, at which time TLC (ethyl acetate) showed only a trace of starting material. The THF was removed by rotary evaporation at room temperature, and the resulting aqueous suspension was diluted with H$_2$O (2 mL), cooled to 0° C., and with rapid stirring was carefully acidified to ca. pH 3 with 0.5 M aqueous HCl. The aqueous mixture was extracted with diethyl ether (5×2 mL), and the combined extracts were washed with H$_2$O and brine (2 mL ea.). The ether phase was dried over Na$_2$SO$_4$, filtered, and concentrated. The residue was chromatographed on a short column (ca. 2 cm) of SiO$_2$ (ethyl acetate) to give the carboxylic acid (29.7 mg, 21.5 μmole, 96% yield) as a colorless foam.

(6) Preparation of lactone (compound 9)

To a stirred solution of the C30 hydroxy-C1 carboxylic acid (29.7 mg, 21.5 μmole) in THF (225 μL) at room temperature under argon was added triethylamine (7.5 μL, 54 μmole), followed by 2,4,6-trichlorobenzoyl chloride (4.2 μL, 27 μmole). The resulting mixture was stirred at room temperature for 2 h, then filtered through a fritted glass filter along with dry toluene washes under argon. The combined filtrate and washes were diluted to 11.25 mL with dry toluene, and the resulting clear, colorless solution was added via syringe pump over 14 h to a stirred 70° C. solution of N,N-dimethylaminopyridine (16.5 mg, 135 μmole) in toluene (10 mL) under argon. The syringe was rinsed with dry toluene (2×0.5 mL) and the rinses were added to the reaction solution. After an additional 2 h (16 h total), the reaction solution was cooled to room temperature, diluted with diethyl ether (20 mL), and washed with 0.5 M aqueous HCl (2×5 mL), H$_2$O, and brine (5 mL ea.). The combined aqueous fractions were extracted with diethyl ether (2×5 mL) and the combined organic phases were dried over Na$_2$SO$_4$, filtered, and concentrated. The residue was purified by PTLC 5:1 hexanes/ethyl acetate) to afford the lactone (23.3 mg, 81% yield) as a clear, colorless oil.

Compound 10

Compound 10 was synthesized from compound 9 by either of the following two procedure.

Example 1

To a stirred solution of compound 9 (35.7 mg, 26.2 μmole) in THF (2.62 mL) and anhydrous methyl acetate (262 μL) was added an approximate 1 M solution of tetrabutylammonium fluoride (TBAF) in THF (79 μL, pH ca. 6.8). After stirring at room temperature for 36 h, TLC (10:1 ethyl acetate/methanol) showed complete desilyation. The reaction solution was filtered through a 2 cm pad of SiO$_2$ (silica gel 60, 230–400 mesh, ethyl acetate) to remove the TBAF. The filtrate was concentrated and the residue dried on a high vacuum line for ca. 1 h before being used in the next step without further purification. $^1$H NMR (C$_6$D$_6$) indicated an approximate 5:1 ratio of diastereomeric Michael-type adducts.

The above product mixture was dissolved in CH$_2$Cl$_2$ (2.0 mL) at room temperature, and to the stirred solution was added pyridinium p-toluenesulfonate (2 mg). After stirring at room temperature for 18 h, TLC (10:1 ethyl acetate/methanol) showed complete conversion to the desired higher R$_f$ polycyclic ketal and a minor lower R$_f$ by-product. The reaction solution was filtered directly through a 1 cm pad of SiO$_2$ with 20:1 ethyl acetate/methanol. The combined filtrate was concentrated and the residue was used without further purification.

To a stirred solution of the crude diol in CH$_2$Cl$_2$ (2.0 mL) at room temperature was added pyridine (17 μL, 210 μmole) followed by p-nitrobenzoyl chloride (19.3 mg, 104 μmole). After stirring at room temperature for 16 h, TLC (ethyl acetate) showed no remaining starting material. The solution was concentrated by rotary evaporation and the residue was suspended in diethyl ether (5 mL) and filtered through a short pad of Celite along with additional ether washes. The filtrate was concentrted and the products were separated by PTLC (ethyl acetate) to afford the higher R$_f$ C38 p-nitrobenzoate/C35 alcohol/C14–C18 polycyclic ketal (15.5 mg, 16.7 μmol, 64% yield over 3 steps and an impure lower R$_f$ C14 ketone by-product.

To a stirred solution of the higher Rf polycyclic ketal (15.5 mg, 16.7 μmole) in DMF (675 μL) was added pyridine (45 μL, 556 μmole), follwed by tert-butyldimethylsilyl chloride (16.4 mg, 109 μmole) and AgNO$_3$ (18.8 mg, 111 μmole). The resulting white suspenseion was stirred in the dark at room temperature for 18 h, at which time TLC showed no remaining starting material. The mixture was diluted with diethyl ether (5 mL) and filtered through Celite along with additional ether washes. The combined filtrate was washed with saturated aqueous NH$_4$Cl, H$_2$O, and brine (5 mL ea.), dried over Na$_2$SO$_4$, filtered through a short pad of SiO$_2$ (ethyl acetate), and concentrated. The residue was purified by PTLC (1:1 hexanes/ethyl acetate) to give the secondary silyl ether (16.1 mg, 15.5 μmole, 93% yield) as a clear, colorless oil.

To a stirred solution of the secondary silyl ether (16 mg, 15 μmole) in a methanol (1 mL) at room temperature was added solid K$_2$CO$_3$ (ca. 0.2 mg). The resulting mixture was stirred at room temperature for 2.5 h, at which time TLC showed no remaining starting material. Toluene (1 mL) and acetic acid (5 μL) were added and the methanol was removed by rotary evaporation. The resulting suspension was filtered through a short pad of SiO$_2$ along with ethyl acetate. The combined filtrate was concentrated and the residue was purified by PTLC (ethyl acetate) to give the primary alcohol (12.8 mg, 14.4 μmole, 93% yield) as a clear, colorless oil. This is compound 10.

Example 2

Compound 10 was also synthesized by an alternative route as set forth below:

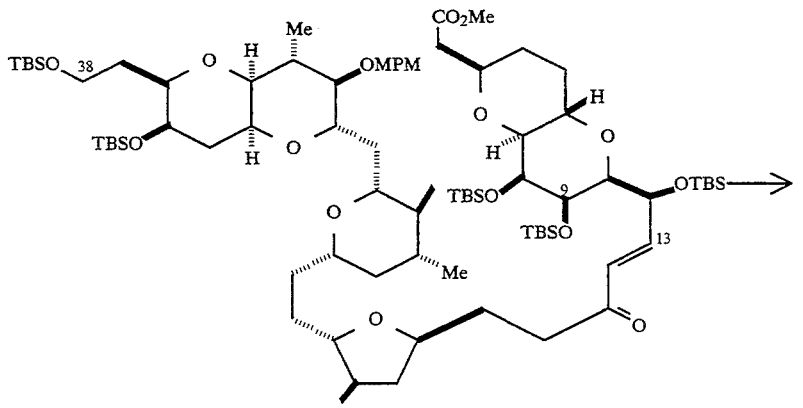

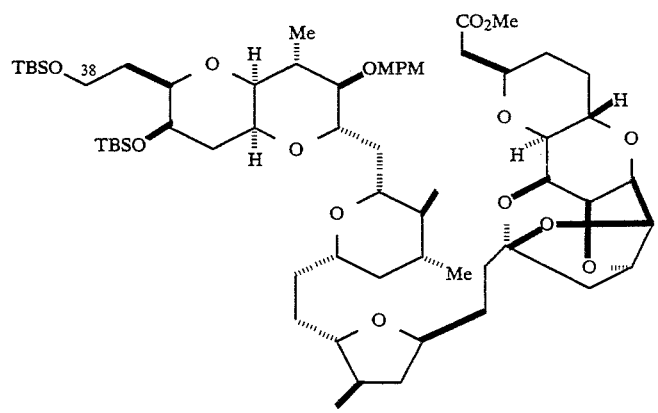

Preparation of cyclic ketal

To a stirred solution of the pentasilyl enone (prepared from the aldehyde derived from 7 and 8 according to the procedures given pages 78–79, 35.0 mg, 23.1 mmol) in THF (5.4 ml) and anhydrous methyl acetate (1.8 ml) was added a 1 M solution of TBAF in THF (1.8 ml, ca pH=7.4). After stirring at room temperature for 21 h, the reaction mixture was concentrated and chromatographed on SiO$_2$ (AcOEt100%- 5%MeOH/CHCl$_3$) to give a mixture of the desired ketone, the undesired ketone and the desilylated enone (30.5 mg).

The above product mixture was dissolved in CH$_2$Cl$_2$ (2.3 ml) at room temperature, and to the stirred solution was added pyridinium p-toluenesulfonate (PPTS) (2 mg). After 11.5 h, additional PPTS (1 mg) was added. After a total of 17 h, the reaction mixture was added saturated aqueous NaHCO$_3$ and extracted with CH$_2$Cl$_2$ (10 ml×3). The combined organic extracts were washed with brine, dried over Na$_2$SO$_4$, filtered and concentrated. The residue was purified by SiO$_2$ column chromatography (AcOEt100%-2%MeOH/AcOEt5-%MeOH/CHCl$_3$) to give the cyclic ketal (KT1-287-1) (15.3 mg, 72% over 2 steps).

Preparation of di-TBS ether

To a stirred solution of diol (KT1-287-1) (15.3 mg, 16.5 mmol) in CH$_2$Cl$_2$ (1 ml) at room temperature was added imidazole (10 mg, 147 mmol) followed by tert-butyldimethylsilyl chloride (9 mg, 60 mmol). After stirring at room temperature for 2 h, the reaction mixture was added water and extracted with CH$_2$Cl$_2$ (10 ml×2). The combined organic extracts were washed with brine, dried over Na$_2$SO$_4$, filtered and concentrated. The residue was purified by SiO$_2$ column chromatography (10%AcOEt/hexanes-30%AcOEt/hexanes50%AcOEt/hexanes) to give the primary TBS ether (KT2-8-1) (13.3 mg, 12.8 mmol, 78%).

The above primary TBS ether was dissolved in CH$_2$Cl$_2$ (1 ml), and to the stirred solution at 0° C. was added triethylamine (14 ml, 102.4 mmol) followed by tert-butyldimethylsilyltrifuluolomthane sulfonate (TBSOTf) (12 ml, 51.2 mmol). After stirring at 0° C. for 30 min, the reaction mixture was added saturated aqueous NaHCO$_3$ (2 ml), brine (5 ml) and extracted with CH$_2$Cl$_2$ (10 ml×2). The combined organic extracts were dried over Na$_2$SO$_4$, filtered and concentrated. The residue was purified by SiO$_2$ column chromatography (10%AcOEt/hexanes-30%AcOEt/hexanes) to give the di-TBS ether (14.4 mg, 12.4 mmol, 98%).

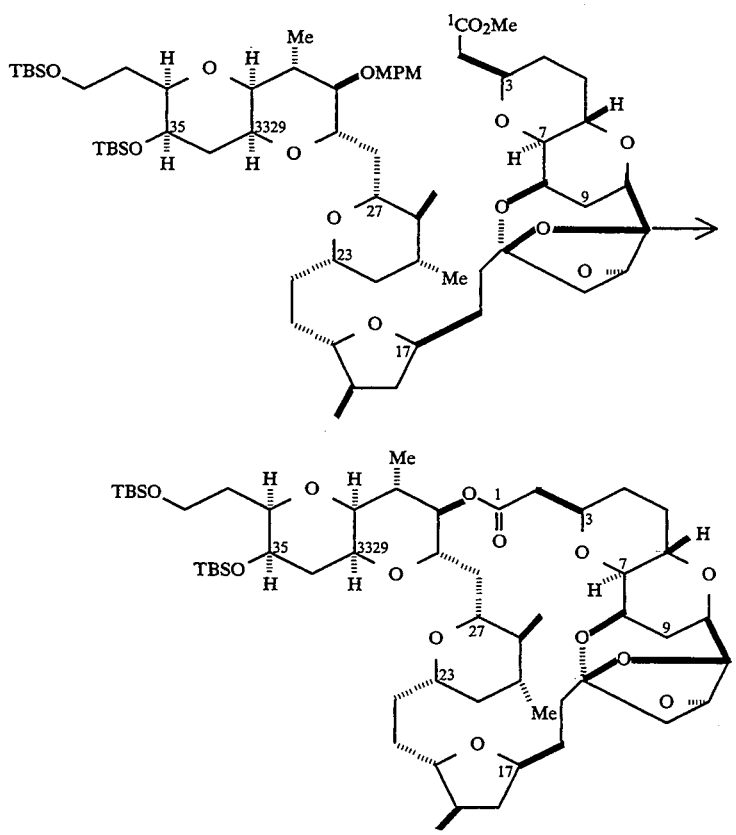

35

Preparation of C-30 alcohol

To a stirred mixture of the MPM ether (KT-2-8-2) (14.4 mg, 12.4 mmol) in CH2Cl2 (560 ml), aqueous phosphate buffer (56 ml), tert butanol (5.6 ml) was added DDQ (5.6 mg, 24.8 mmol). The resulting mixture was sonicated for 30 sec, and stirred for 3 min, and sonicated for an additional 30 sec, and then stirred for 3 min. The reaction mixture was added saturated aqueous NaHCO3 (2 ml) and extracted with CH2Cl2 (10 ml×3). The combined organic extracts were washed with brine, dried over Na2SO4, filtered and concentrated. The residue was purified by PTLC (hexanes:AcOEt:-bezene=1.5:1:1, 2 elutions) to afford the higher Rf desired C-27 diastereomer (8.5 mg, 8.2 mmol, 66%) (KT2-9-1) and the lower Rf undesired C-27 diastereomer (2.6 mg, 2.5 mmol, 20%) (KT2-9-2) as a colorless oil.

Preparation of carboxylic acid

To a stirred solution of the methylester (KT2-9-1) (8.5 mg, 8.2 mmol) in THF (550 ml) at room temperature was added 1 M aqueous LiOH (250 ml). After stirring at room temperature for 9 h,THF was removed under reduced pressure. To this residue, CH2Cl2 (10 ml) and brine (10 ml) were added, and the resulting mixture was acidifide to ca. pH=3 with 0.1 M HCl. The mixture was shaken and organic phase was separated. The aqueous phase was extracted with CH2Cl2 (10 ml×2), and the combined organic extracts were washed with brine, dried over Na2SO4, filtered and concentrated. The residue was chromatographed on a SiO2 short column (CHCl3-5%MeOH/CHCl3-10%MeOH/CHCl3) to give the carboxylic acid (KT2-9-1) (8.3 mg, 8.2 mmol, 100%)

Preparation of lactone

To a stirred solution of the carboxylic acid (KT-2-9-1) (8.3 mg, 8.2 mmol) in THF (250 ml) at room temperature under argon was added triethylamine (4.6 ml, 33.2 mmol) followed by 2,4,6-trichlorobenzoyl chloride (2.6 ml, 16.6 mmol). The resulting mixture was stirred at room temperature for 2 h, then diluted with toluene (6 ml). The resulting solution was added via syringepump over 8.5 h to a stirred 80° C. solution of N,N-dimethylaminopyridine (DMAP) (6.3 mg, 51.4 mmol) in toluene (2 ml) under argon. The syringe was rinsed with dry toluene (1 ml×2) and the rinses were added to the reaction solution. After 11 h, additional DMAP (6.3 mg, 51.4 mmol) and triethylamine (4.6 ml, 33.2 mmol) in toluene (1 ml) were added. After a total of 32 h, the reaction mixture was cooled to room temperature, added brine (10 ml). The resulting mixture was acidified to ca. pH=3 with 0.1 M HCl, extracted with ether (10 ml), then CH2Cl2 (10 ml×2). The combined organic extracts were dried over Na2SO4, filtered and concentrated. The residue was purified by PTLC (40%AcO-Et/hexanes) to afford the lactone 9 (6.6 mg, 6.6 mmol, 80%).

Note that the above pentasilyl enone was also prepared by the Horner-Emmons reoute as shown below.

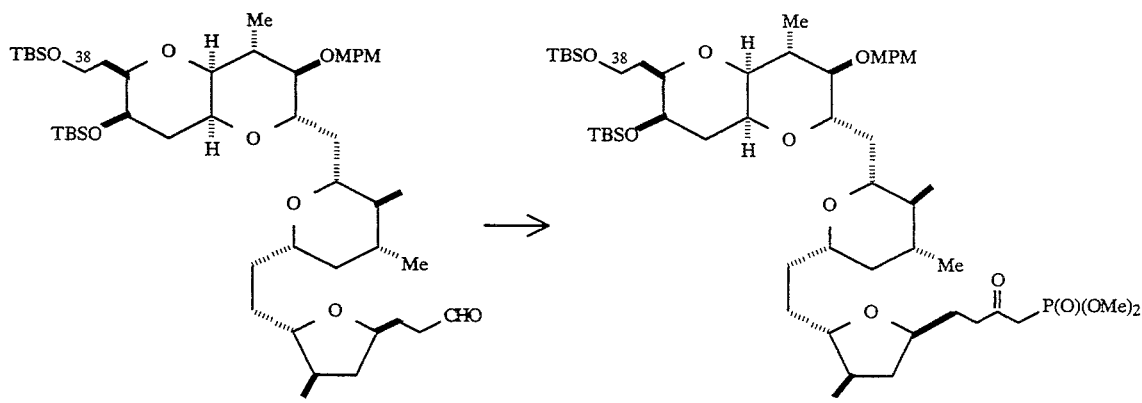

Preparation of C-14 carboxylic acid

To a stirred solution of C-14 aldehyde (77.7 mg, 0.125 mmol) in tert-buthanol (2.5 ml) and 2-methyl-2-butene (0.6 ml) at room temperature, a soulution of $NaClO_2$ (100 mg, 1.1 mmol) and $NaH_2PO_4$ (100 mg, 0.72 mmol) in water (1 ml) was added dropwise over 10 min. After stirring at room temperature for 30 min, the rection mixture was added water (5 ml) and extracted with AcOEt (10 ml×3). The combined extracts were washed with brine, dried over $Na_2SO_4$, filtered and concentrated to give the carboxylic acid (82.2 mg) as a clear oil. This crude product was used without further purification.

Preparation of methyl ester

To a stirred solution of the carboxylic acid (82.2 mg) in diethyl ether (5 ml) at 0° C. was added a solution of diazomethane in diethyl ether (excess). After stirring at 0° C. for 10 min, the mixture was concentrated and the residue was purified by $SiO_2$ column chromatography (5%AcOEt/hexanes-10%AcOEt/hexanes) to give the C-14 methyl ester (72.4 mg, 0.11 mmol, 89% over 2 steps) as a clear oil. Preparation of keto phosphonate To a stirred solution of dimethyl methylphosphonate (120 ml, 1.1 mmol) in THF (2 ml) at −78° C. a solution of n-buthyllithium in hexanes (780 ml of 1.31 M, 1.0 mmol) was added dropwise. The mixture was stirred at −78° C. for 1 h before a solution of methyl ester (72.4 mg, 0.11 mmol) in THF (3.5 ml) was added dropwise at −78° C. After stirring at −78° C. for 50 min, the reaction mixture was added a saturated aqueous solution of $NH_4Cl$ and extracted with AcOEt (10 ml×3). The combined extracts were washed with brine, dried over $Na_2SO_4$, filtered and concentrated. The residue was purified by $SiO_2$ column chromatography (50%AcOEt/hexanes-80%AcOEt/hexanes) to give the keto phosphonate (73.5 mg, 0.099 mmol, 89%) as a clear oil.

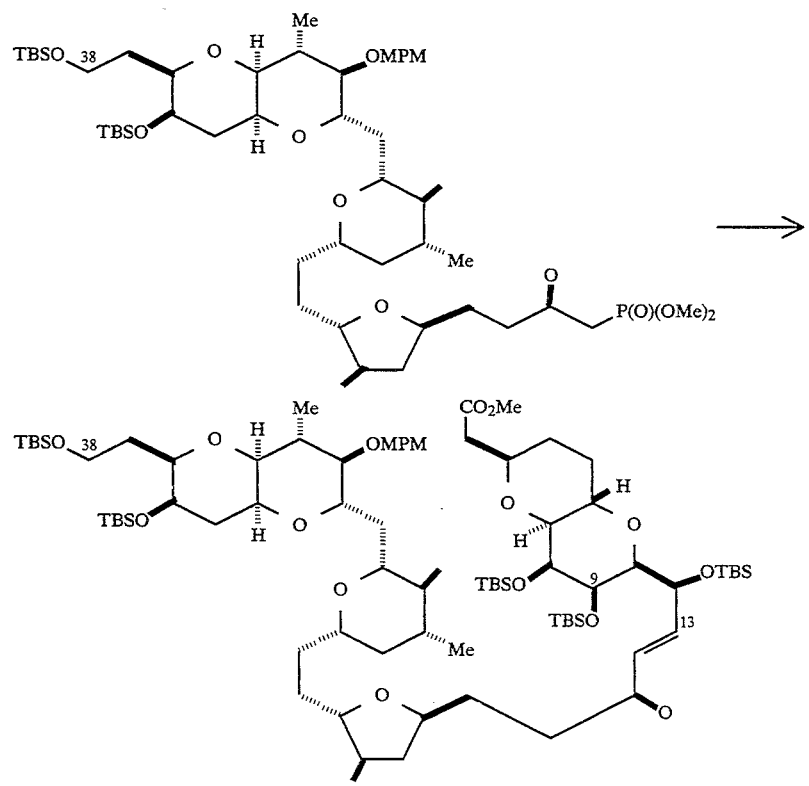

Preparation of enone

To a stirred solution of the keto phosphonate (56.0 mg, 0.075 mmol) in THF (2 ml) at 0° C., a 5% suspention of NaH in minerl oil (36 mg, 0.075 mmol) was added. The mixture was stirred at 0° C. for 1 h before a solution of C-12 aldehyde (42 mg, 0.065 mmol) in THF (3 ml) was added at 0° C. The reaction mixture was slowly warmed up to room temperature over 30 min. The reaction mixture was recooled to 0° C. and a saturated aqueous solution of NH₄Cl (5 ml) was added. The mixture was extracted with AcOEt (10 ml×3) and the combined extracts were washed with rine, dried over Na₂SO₄, filtered and concentrated. The residue was purified by SiO₂ column chromatography (10%AcOEt/hexanes-20%AcOEt/hexanes-50%AcOEt/hexanes-80%AcOEt/hexanes) to give the enone (35.0 mg, 0.023 mmol, 85% of convertion yield based on keto phosphonate) and the recovered keto phosphonate (30 mg, 0.048 mmol, 89%) as a clear oil.

Compound 11

Compound 11 was synthesized according to the following producedure.

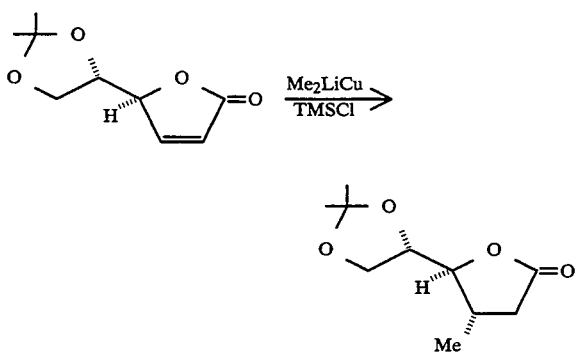

To a flame-dried, nitrogen cooled 250-ml 3-neck flask equipped with a magnetic stirbar and nitrogen inlet was added freshly prepared CuBr-DMS complex (5.57 g, 27.2 mmol). The flask was evacuated again and charged with nitrogen. Dry THF (80 mL) was introduced via syringe and the resulting suspension cooled to −78° C. Methyllithium (Aldrich, 1.45 M in ether, 38 mL) was added dropwise via syringe over 15 min. The yellow suspension eventaully became clear and colorless. Freshly distilled TMSCl (6.9 mL, 54.4 mmol) was introduced next dropwise via syringe. The resulting colorless solution was stirred for 5-10 min. The butenolide (2.55 g, 13.9 mmol) was dissolved in 5 mL of dry THF and added dropwise over 1-15 min. The resulting-reaction was stirred at −78° C. for 1 h, during which time the color changed from yellwo to orange. The cooling bath was removed and mixture stirred at room temperature for 8 h. The dark green reaction was quenched by cautious dropwise addition of 35 mL saturated 10% NH₄OH/NH₄Cl. The flask was opened to the air and stirred for 12 h. The aqueous layer turned bright blue during this time. The organic layer was decanted and the aqueous layer was extracted with ethyl acetate (3×50 mL). The combined organic layers were washed with saturated ammonium chloride, brine, and dried with sodium suflate. The solvents were evaporated to give nearly pure product (2.64 g, 13.2 mmol, 95% yield) as an oil. A sample was subjected to silica gel chromatography (65% ether/hexanes) to give analytically pure product.

IR (film): 2985 cm⁻¹ 2936, 2887, 1779, 1456, 1419, 1380, 1372, 1257, 1211, 1158, 1128, 1093, 1062, 1025, 987, 966, 948, 914, 870, 827.

¹H NMR (CDCl₃): δ1.17 (2 H, d, J=6.9 Hz), 1.36 (3 H, s), 1.38 (3 H, s), 2.11 (1 H, dd, J=5.8, 17.5 Hz), 2.59 (1 H, ddtd, J=4.7, 5.8, 6.9, 8.9 Hz), 2.83 (1 H, dd, J=8.9, 17.5 Hz), 3.92 (1 H, dd, J=7.5, 8.2 Hz), 4.04 (1 H, dd, 2.3, 4.7 Hz), 4.07 (1 H, dd, J=6.9, 8.2 Hz), 4.21 (1 H, ddd, J=2.3, 6.9, 7.5 Hz).

¹³C NMR (CDCl₃): δ19.49, 25.70, 25.89, 32.20, 36.58, 65.48, 76.26, 84.40, 109.99, 176.33.

MS (FAB): 201 amu (M⁺ +H, rel. intensity 25%), 185 (21), 147 (15), 73 (100).

[α]_D: +21.5° (C 2.00 CH₂Cl₂).

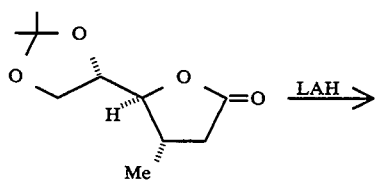

To a suspension of LAH (190 mg, 5.0 mmol) in 10 mL of dry ether cooled to 0° C. was added dropwise a solution of the lactone (500 mg, 2.5 mmol) in 1 mL of ether. TLC (50% ethyl acetate/hexanes) indicated a complete reaction after 0.5 h. To the reaction mixture was added 200 μL H₂O, 200 μL 15% aqueous NaOH, and 600 μL H₂O. The mixture was stirred until a white precipitate appeared. The solution was filtered through a pad of Celite and washed with ether. The solvent was evaporated to give a nearly quantitative yield of a slightly yellow oil. The product was used without further purification for the subsequent reaction.

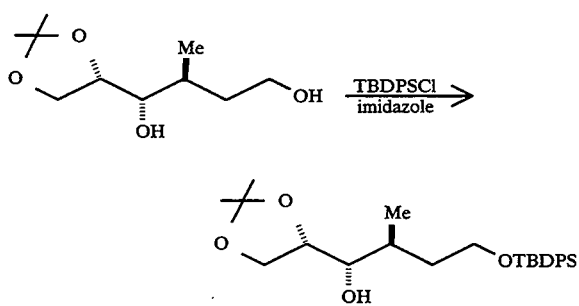

To a solution of the diol (747 mg. 3.66 mmol) in dichloromethane (10 mL) was added imidazole (500 mg, 7.32 mmol). The mixture was acooled to 0° C., and t-butyldiphenylsilychloride was added dropwise. The reaction mixture was allowed to warm to room temperature for 1 h, after which TLC (15% ethyl acetate/hexanes) indicated the reaction was complete. The mixture was quenched with water and extracted with dichloromethane. The organic layers were washed with brine, and dried with sodium sulfate. The solvents were removed in vacuo, and the resulting oil subjected to silica gel column chromatography (15% ethyl acetate/hexanes) to yield a pure product (1.50 g, 94% yield).

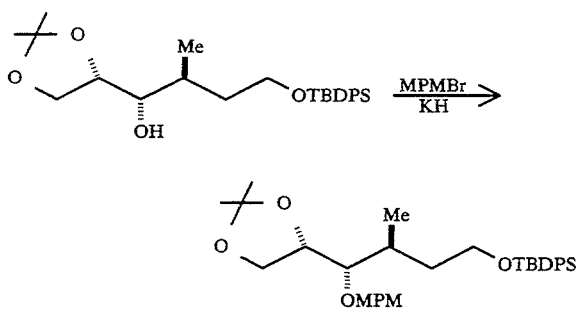

A solution of the alcohol (126 mg, 0,285 mmol) and freshly prepared MPMBr (86 mg, 0.428 mmol) were dissolved in dry THF (15 mL) and cooled to 0° C. To this mixture was added oil-free KH (200 mg, 5.09 mmol) portion wise. The reaction was warmed to room temperature for 1.5 h, then diluted with ether and quenched with saturated ammonium chloride. The organic layer was removed, and the aqueous layer extrated with ether (3×10 mL). The combined organic layers were washed with brine, dried over sodium sulfate, and filtered. The solvents were removed and the viscous oil purified via silica gel column chromatography (10% ethyl acetate/hexanes) to give the product (148 mg, 92% yield).

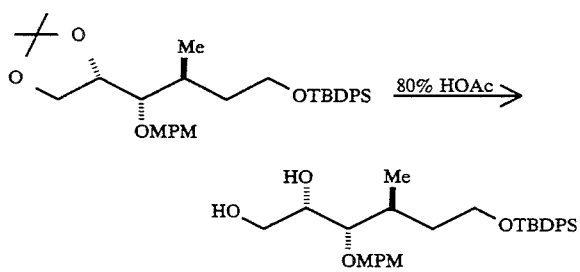

To a solution of the acetonide (7.50 g, xx mmol) in THF (10 mL) was added 80% HOAc (40 mL) at room temperature. The reaction was carefully monitored by TLC-(50% ethyl acetate/hexanes). The reaction is generally complete within 4 h. The mixture was diluted with ethyl acetate, and quenched with water. Solid sodium bicarbonate was added to consume the excess acetic acid. The aqueous layer was then extracted with more ethyl acetate. The combined organic layers were dried over magnesium sulfate, and the solvents removed in vacuo to yield the diol (5.6 g, 80% yield) as a viscous oil.

IR (film) 1034 cm$^{-1}$ 1159, 1249, 1514, 1612, 1724, 2961, 435.

$^1$H NMR (CDCl$_3$, 500 mHz): δ1.06 (3 H, d, J=6.9 Hz), 1.19 (9 H, s), 1.53 (1 H, m), 1.85 (1 H, m), 1.96 (1 H, m), 2.04 (1 H, m), 2.51 (1 H, d, J=6.5 Hz), 3.31 (1 H, m), 3.59 (2 H, m), 3.72 (1 H, m), 3.81 (3 H, s, -OCH$_3$), 4.10 (1 H, m), 4.14 (1 H, m), 4.46 (1 H, d, J=10.9 Hz), 4.63 (1 H, d, J=10.9 Hz), 6.89 (2 H, d, J=8.5 Hz), 7.25 (2 H, d, J=8.5 Hz).

HRMS (FAB) calcd for C$_{20}$H$_{32}$O$_6$ (M$^+$+Na) 391.2097, found (M$^+$+Na) 391.2119.

[α]$_D$−9.2° (c 1.2, MeOH).

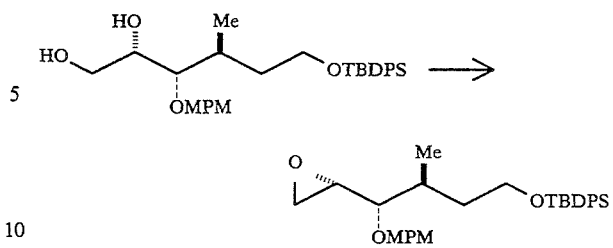

To a suspension of NaH (60% in oil, 2.33 g, 58 mmol) in THF (300 mL) at room temperature was added a solution of the diol (3.18 g, 6 mmol) in THF (20 mL). After being stirred for 40 min, the mixture was cooled to 0° C. and TsIm (1.49 g, 6.7 mmol) was added portionwise. The mixture was stirred at 4° C. overnight. The reaction was quenched by the addition of water and the organic layer was separared. The aqueous layer was extracted with ether. The organic layer was dried over NaSO$_4$ and the solvents were removed by rotary evaporation. The residue was column chromatographed (Hexane:EtOAc=8:1) to give the epoxide (2.53 g, 83% yield). For better result, slower addition of TsIm as a solution is suggested.

IR (film) 821 cm$^{-1}$ 1159, 1285, 1514, 1613, 1726, 2970, $^1$H NMR (CDCl$_3$): δ1.07 (9 H, s, t-Bu), 1.51 (1 H, m), 1.89 (1 H, m), 1.95 (1 H, m), 2.52 (1 H, m), 2.81 (2 H, m), 3.05 (1 H, m), 3.80 (3 H, s), 4.09 (2 H, m), 4.49 (1 H, d, J=11.5 Hz), 4.78 (1 H, Hz), 7.29 (2 H, d, J=8.6 Hz). 7.29 (2 H, d, J=8.6 Hz).

HRMS (FAB) calcd for C$_{20}$H$_{30}$O$_5$+Na 373.1991, found 373.2007.

[α]$_D$−12.2° (c 0.98, MeOH).

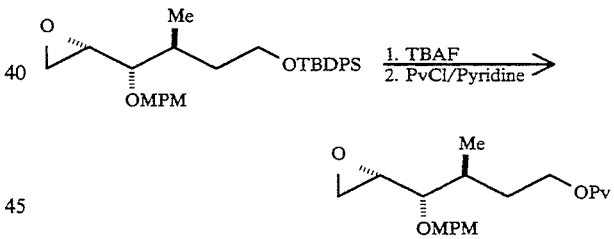

To a solution of TBDPS ether (790 mg, 1.56 mmol) in THF (30 mL) was added TBAF (5 mL, 5 mmol) at room temperature. After stirring for 2 h, the reaction mixture was concentrated, diluted with EtOAc, and saturated aqueous NH$_4$Cl. The organic layer was separated and washed with water followed by brine. The organic layer was dried over sodium sufate and concentrated under reduced pressure. The residue was purified by column chromatography with 25% EtOAc in hexames to afford 406 mg of alcohol as a colorless oil.

The purified alcohol was dissolved in CH$_2$Cl$_2$ (10 mL) and treated with pyridine (0.90 mL, 10.9 mmol) and PvCl (1.20 mL, 9.39 mmol) followed by a catalytic amount of DMAP. The reaction was purified by column chromatography with 33% EtOAc in hexane to afford the pivaloate (505 mg, 92% yield over 2 steps) as oil.

IR (film) 821 cm$^{-1}$ 1159, 1285, 1514, 1613, 1726, 2970.

$^1$H NMR (CDCl$_3$): δ1.07 (9 H, s, t-Bu), 1.51 (1 H, m), 1.89 (1 H, m), 1.95 (1 H, m), 2.52 (1 H, m), 2.81 (2 H, m), 3.05 (1 H, m), 3.80 (3 H, s), 4.09 (2 H, m), 4.49 (1 H, d, J=11.5 Hz), 4.78 (1 H, d, J=11.5 Hz), 6.87 (2 H, d, J=8.6 Hz), 7.29 (2 H, d, J=8.6 Hz).0

HRMS (FAB) calcd for $C_{20}H_{30}O_5+Na$ 373.1991, found 373.2007.

$[\alpha]_D$ −12.2° (c 0.98, MeOH).

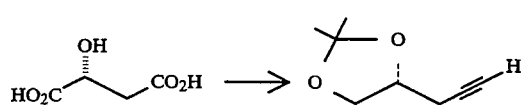

To a solution of $BH_3$ $SMe_2$ (87.5 mL, 0.923 mol) and trimethyl borate (91 mL, 0.80 mol) in 200 mL of TH at 0° C. was added dropwise a solution of D-(+)-malic acid (35 g, 0.261 mol) in THF (150 mL). The solution was warmed up to room temperature and was stirred overnight. Methanol (230 mL) was added dropwise and solvents were evaporated. Further three coevaporations with methanol (100 mL) and concentration in vacuo gave the crude product.

The crude product mixture was divided into two portions. Each portion was dissolved in 950 mL of acetone and TsOH. $H_2O$ (1.0 g) was added. After each solution being stirred overnight, triethylamine (1 mL) was added and the mixture was stirred for a while. The solvent was removed by rotary evaporation. The combining residue was column chromatographed (Hexane: Acetone=7:3) to give 33 g (86%, two steps) of the mixture of product.

The mixture of products (33 g) was divided into 5 different batches. Two batches were oxidized by Swern's method and three batches were oxidized by the PCC method. PCC method was better than Swern's method for this particular substrate. All together 18.0 g (55%) of the aldehyde was obtained.

The mixture of aldehyde (18 g) was divided into 5 g (34.7 mmol) and 13 g (90.2 mmol) batches. The following is a procedure for the 13 g scale reaction. To a suspension of KO$^t$Bu (13.3 g. 119 mmol) in 350 mL of THF at −78° C. was added dropwise DAMP (16.2, 108 mmol). After the mixture being stirred for 15 min, a solution of the aldehyde in 40 mL of THF was added dropwise (ca.. 10 min). After 12 h stirring at this temperature, water (100 mL) was added. The organic layer was separated and was diluted with methylene chloride (350 mL). This organic layer was washed with water (4×70 mL) and brine (50 mL). The combined aqueous layer was extracted with methylene chloride (150 mL and 50 mL). These extracts were washed with brine (30 mL). All combined organic layers were dried (NaSO$_4$). Solvents were distilled off after extracts of the 5 g reaction mixture had been combined. Vacuum distillation of the residue gave 9.24 g (52%) of the desired product (bp. 62°–64° C./ca. 25 mmHg).

IR (film) 732 cm$^{-1}$ 910, 1069, 2270, 2901, 2963, 3021, 3309.

$^1$H NMR (CDCl$_3$): δ1.36 (3 H, s), 1.43 (3 H, s), 2.00 (1 H, t, J=2.6 Hz), 2.42 (1 H, ddd, J=2.6, 7.3, 16.5 Hz), 2.53 (1H, ddd, J=2.6, 5.2, 14.0 Hz), 3.77 (1 H, dd, J=6.2, 8.5 Hz), 4.11 (1 H, dd, J=6.0, 8.5 Hz), 4.24 (1 H, m)

HRMS (CI) calcd for $C_8H_{12}O_2+H$ 141.0915, found (M+H)+ 141.0923.

$[\alpha]_D$ −38.7° (C 1.68, MeOH).

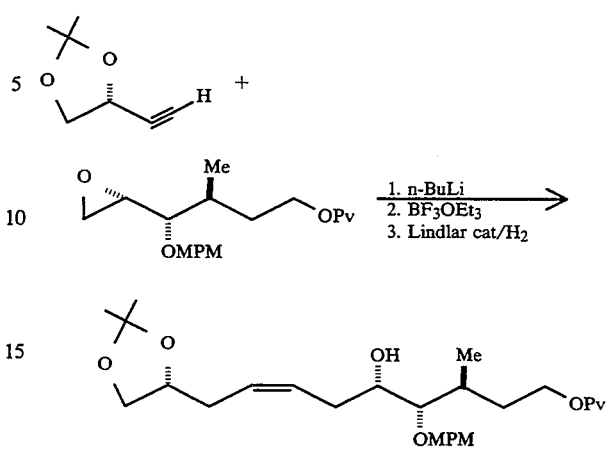

To a solution of acetylene (257 mg, 1.82 mmol) in THF (13 mL) was added n-BuLi (1.67 mmol) at −78° C. After stirring for 1 h, BF$_3$.OEt$_2$ (0.20 mL, 1.60 mmol) was added to the anion solution and the reaction mixture was stirred for 20 min. To the reaction mixture was added a solution of epoxide (257 mg. 0.733 mmol) in THF (4 mL) over 20 min. After stirring for 1 h, it was stirred at −45° C. for another 20 min and quenched with saturated NH$_4$Cl. After normal workup, the residue was purified by column chromatography with 20% ethyl acetate in hexanes to afford the alkyne (317 mg, 88.8% yield).

To the above solution of alkyne in hexanes (26 mL) was added quinoline (0.69 mL) followed by Pd/CaCO$_3$ (173 mg). To the reaction mixture was attached a hydrogen balloon and the reaction mixture was stirred for 50 min. The reaction mixture was filtered through Celite and the filtrate was washed with 10% HCl (2×10 mL), water, saturated aqueous NaHCO$_3$, and brine. After drying and concentration, it gave the homoallylic alcohol (310 mg. 97.8% yield).

IR (Film) 1514, cm$^{-1}$ 1612 1725 2978 3502

$^1$H NMR (CDCl$_3$): δ1.03 (3 H, d, J=6.9 Hz), 1.19 (9 H, s), 1.34 (3 H, s), 1.41 (3 H, s), 1.51 (1 H, m), 1.88 (1 H, m), 1.96 (1 H, m), 2.20–2.42 (4 H, m), 2.44 (1 H, d), 3.14 (1 H, m), 3.54 (1 H, t, J=7.6 Hz), 3.69 (1 H, m), 3.80 (3 H, s), 4.02 (1 H, dd), 4.07∼4.17 (2 H, m), 4.57 (2 H, dd), 5.56 (2 H, m), 6.88 (2 H, d), 7.26 (2 H, d).

HRMS calcd for $C_{28}H_{44}O_7+Na$ (M+ +Na) 515.2985, found 515.2972.

$[\alpha]_D$ −7.3° (c 1.1, MeOH).

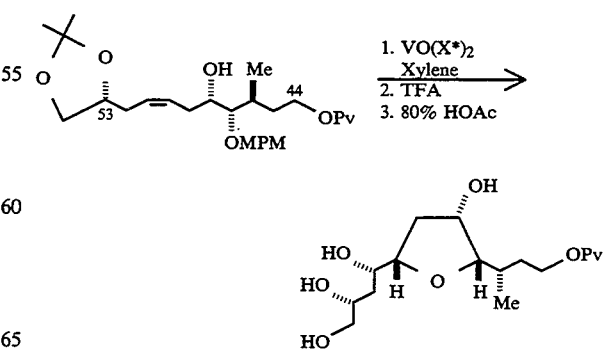

To a solution of alkene (1.01 g, 2.23 mmol) in xylene (18 mL) was added VO(X*)2 (10 mg) followed by 3 M t-BuOOH (743 μL). The reaction mixture was stirred for 30 min at room temperature. Additional catalyst (3 mg) and t-BuOOH (185 μL) were added. After 12 h, catalyst (3 mg) and t-BuOOH (75 μL) were added and the reaction mixture was stirred for an additional 12 h. (The reaction was stopped before it showed a higher spot than starting material on TLC plate. The reaction time could be changed.) After reductive workup with sodium thiosulfate solution, the crude compound was dissolved in CH$_2$Cl$_2$ (35 mL). The solution was treated with TFA (1 eq.) for 10 min to produce a mixture of cyclized products. To the reaction mixture was added 80% HOAc (40 mL). The reaction mixture was stirred for 3 h, concentrated under reduced pressure, and purified by preparative TLC with 9% MeOH in EtOAc to afford the desired tetraol (420 mg, 59.6% yield) along with undesired tetraol (57 mg. 8.2% yield). (* X=2,2,6,6-Tetramethyl-3,5-heptanedione.)

s), 0.39 (3 H, s), 0.85 (3 H, d, J=6.8 Hz), 0.97 (9 H, s, t-Bu), 1.02 (9 H, s, t-Bu), 1.06 (9 H, s, t-Bu), 1.07 (9 H, s, t-Bu), 1.11 (1 H, t, J=7.1 Hz), 1.55 (1 H, m), 1.64 (1 H, m), 1.76 (1 H, m), 1.89 (1 H, m), 1.99 (1 H, m), 2.04 (1 H, m), 2.18 (1 H, m), 3.03 (1 H, dd, J=3.4, 9.4 Hz), 3.25 (1 H, q, J=7.1 Hz), 3.64 (1 H, m), 3.70 (1 H, m), 3.81 (1 H, dd, J=3.9, 10.4 Hz), 3.87 (1 H, m), 3.89 (1 H, m), 4.04 (1 H, m), 4.25 (1 H, m).

HRMS (FAB) calcd for C$_{36}$H$_{80}$O$_6$Si$_4$+Na 743.4929, found 743.4937.

[α]$_D$−1.5° (c 2.3, MeOH).

To a solution of the above alcohol (35 mg. 0.048 mmol) in CH$_2$Cl$_2$ (2.5 mL) was added Dess-Martin reagent (42 mg. 2 eq.) with solid NaHCO$_3$ (2 eq.) to buffer this reaction system. The reaction mixture was stirred for 1.5 h, and worked up with sodium thiosulfate (6 eq.) solution in saturated aqueous NaHCO$_3$. After extraction, drying, and concentration, the residue was purified by column chromatography with 20% EtOAc in hexanes to give 34 mg of aldehyde in quantitative yield.

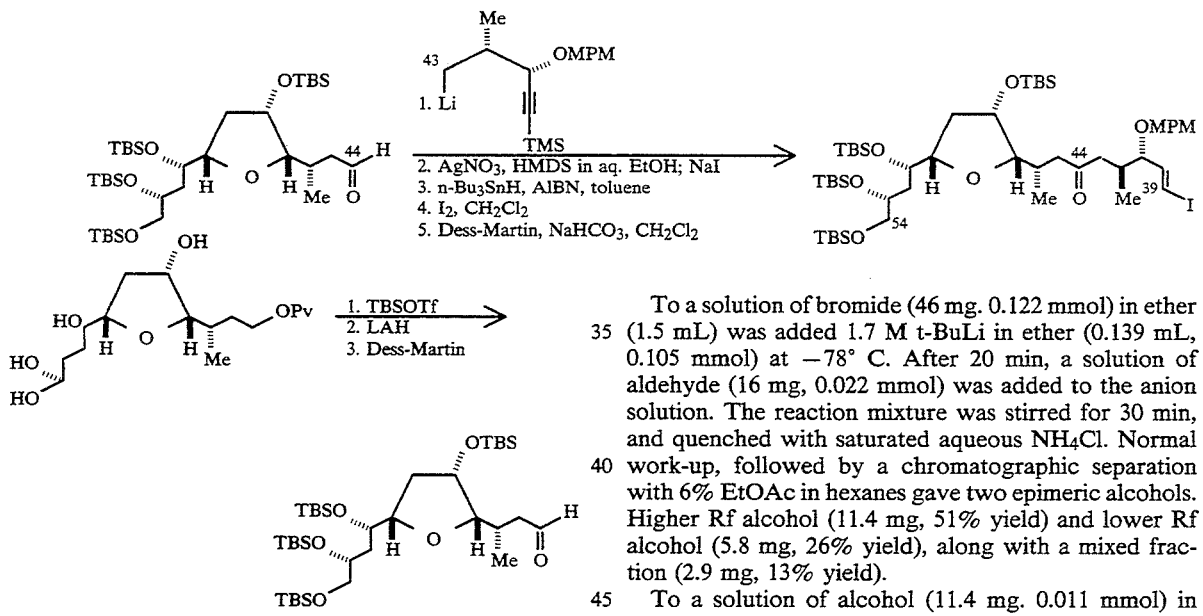

To a solution of tetraol (42.1 mg. 0.120 mmol) in CH$_2$Cl$_2$ (2 mL) at 0° C. was added TBSOTf (0.194 mL, 0.845 mmol) and NEt$_3$ (0.202 mL, 1.45 mmol). The reaction mixture was stirred for 1.6 h and quenched with saturated aqueous NaHCO$_3$. The mixture was extracted with ether (3×5 mL) and the combined organic layers were washed with water and brine. The solvent was dried over Na$_2$SO$_4$, filtered, and concentrated. The residue was purified by column chromatography with 60% EtOAc in hexanes.

The purified compund (89.3 mg) was dissolved in ether (10 mL) and treated with 1.6M LAH in ether (2 eq.) at 0° C. After stirring for 5 min, the reaction mixture was quenched with saturated aqueous Rochelle salt. The reaction mixture was stirred until it formed a clear solution. Normal extraction and purification by column chromatography with 12% EtOAc in hexanes gave the alcohol (67 mg, 83.9% yield).

IR (film) 775 cm$^{-1}$ 836, 1078, 1254, 1473, 2857, 2929, 2955, 3450.

$^1$H NMR (C$_6$D$_5$): δ0.00 (3 H, s), 0.04 (3 H, s), 0.14 (3 H, S), 0.25 (3 H, s), 0.27 (3 H, s), 0.28 (3 H, s) 0.29 (3 H,

To a solution of bromide (46 mg. 0.122 mmol) in ether (1.5 mL) was added 1.7 M t-BuLi in ether (0.139 mL, 0.105 mmol) at −78° C. After 20 min, a solution of aldehyde (16 mg, 0.022 mmol) was added to the anion solution. The reaction mixture was stirred for 30 min, and quenched with saturated aqueous NH$_4$Cl. Normal work-up, followed by a chromatographic separation with 6% EtOAc in hexanes gave two epimeric alcohols. Higher Rf alcohol (11.4 mg, 51% yield) and lower Rf alcohol (5.8 mg, 26% yield), along with a mixed fraction (2.9 mg, 13% yield).

To a solution of alcohol (11.4 mg. 0.011 mmol) in ethanol (2 mL) was added hexamethyldisilamide ("HMDS", 16.7 μL, 0.077 mmol) followed by a solution of AgNO$_3$ (11.5 mg, 0.067 mmol) in 65% aqueous ethanol (1.06 mL). The reaction mixture was stirred for 1 h until the formation of a brown precipitate and clear solution indicated completion of the reaction. The reaction mixture was diluted with ether (2 mL) and treated with a solution of NaI (20 mg, 0.132 mmol) in 0.4 mL of H$_2$O. It was stirred for 20 min and filtered through Celite. The filtrae was extracted with ethyl acetate (3×7 mL). The combined organic layers were concentrated and the residue was filterd through a short SiO$_2$ plug to afford ∼11 mg of acetylene. This acetylene was dried by azeotropic removal of water and dissolved in toluene (1 mL).

To the above solution was added n-Bu$_3$SnH (0.1 mL, 0.15 mmol) followed by a catalytic amount of AIBN. The reaction mixture was heated to 80° C. for 1 h, concentrated, and purified by column chromatography with 6% ethyl acetate in hexanes to give the vinyl tin (10.7 mg, 80% yield).

To a purified vinyl tin solution in dichloromethane (1 mL) was added a solution of iodine (2.6 mg, 0.013 mmol) at 0° C. until the iodine color persisted. The reaction mixture was worked up as usual with NaHSO₃ solution and the crude residue was purified by column chromatography with 6% ethyl acetate in hexanes to give the vinyl iodide. The vinyliodide in 1 mL of CH₂Cl₂ was treated with Dess-Martin reagent (2 eq.) for 1 h. After reductive worked up, the residue was purified by column chromatography with 4% EtOAc in hexanes to afford 9.8 mg of the ketone in quantitive yield.)

Normally this 3-step reaction after coupling gave ~82% yield of compound 11 in a large scale.

IR (film) 791 cm⁻¹ 863, 1084, 1271, 1622, 1727, 2856, 2929.

¹H NMR (C₆D₆): δ0.01 (3 H, s), 0.02 (3 H, s), 0.14 (6 H, s), 0.25 (3 H, s), 0.26 (3 H, (3 H, s), 0.27 (3 H, s), 0.28 (3 H, s), 0.87 (3 H, d, J Hz), 0.96 (9 H, s), 0.98 (3 H, d, J=6.8 Hz), 1.02 (9 H, s), 1.07 (9 H, s), 1.08 (9 H, s), 1.35 (1 H, br s), 1.58 (1 H, m), 1.76 (1 H, M), 1.91 (1 H, m), 1.99 (1 H, m), 2.20 H, dd, J=8.7, 16.7 Hz), 2.29 (1 10.2, 16.7 Hz), 2.39 (1 H, m), 2.53 (1 H, dd, J−4.2, 16.7 Hz), 2.67 (1 H, m), 2.97 (1 H, dd, J=2.2, 16.7 Hz), 3.10 (1 H, m), 3.30 (1 H, m), 3.32 (3 H, s), 3.69 (1 H, dd, J=6.0, 10.3 Hz), 3.76 (1 H, m), 3.80 (1 H, dd, J=3.5, 10.3 Hz), 3.92 (1 H, m), 4.00 (1 H, m), 4.05 (1 H, d, J =11.5 Hz), 4.26 (1 H, m), 4.35 (1 H, d, J=11.5 Hz), 6.01 (1 H, d, J=14.5 Hz), 6.33 (1 H, dd, J=7.8, 14.5 Hz), 6.79 (2 H, d, J=8.6 Hz), 7.13 (2 H, d, J=8.6 Hz).

HRMS (FAB) calcd for C₅₀H₉₅O₈ISi₄+Na 1085.5048, found 1085.5022.

[α]_D−16.8° (c 1.4 CHCl₃).

Compound 12

Compound 12 was synthesized according to the procedure shown in Scheme 4.

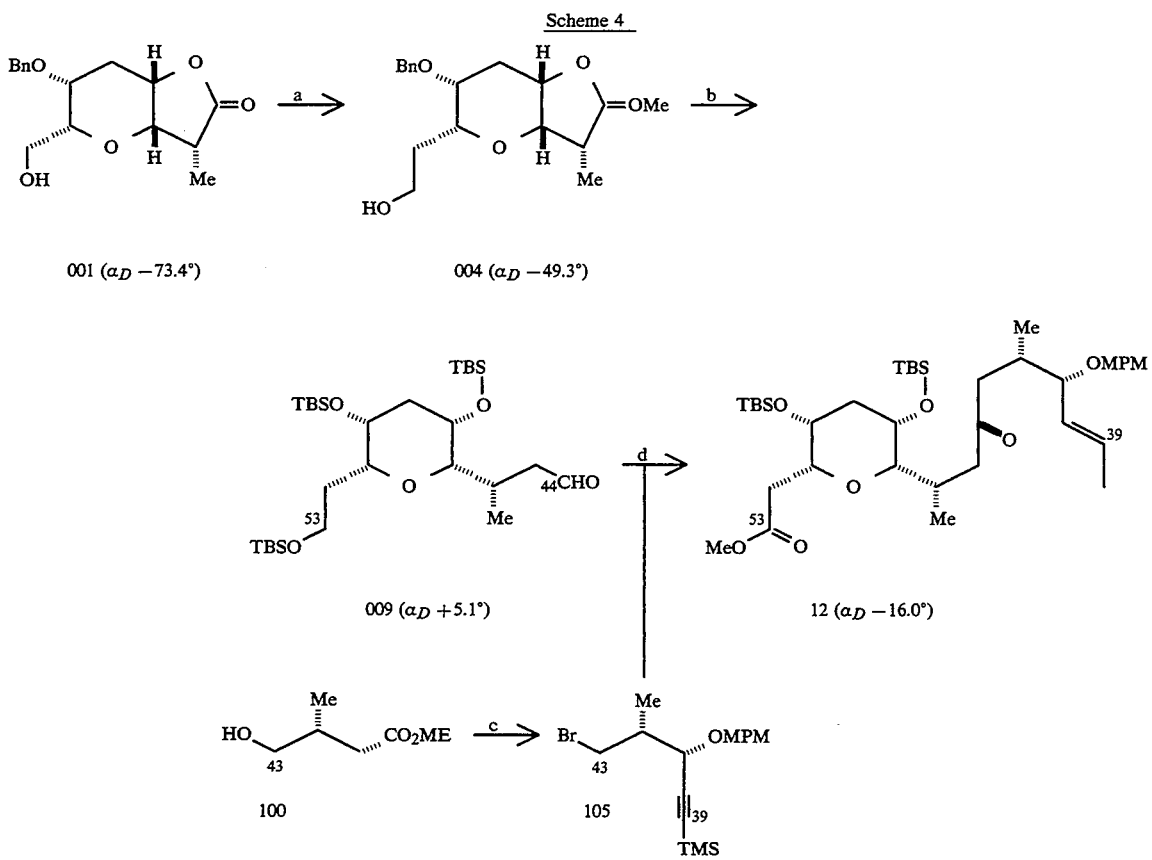

The above γ-lactose 001 is readily available from D-galactose glycal via Ireland-Claisen rearrangement and iodolacorrization

Step a (1) Preparation of nitrile

The lactose was treated by, according to standard procedures, with DEBAL/CH₂Cl₂/−78° C.→0° C.; p-TsOH/MeOH at room temperature; and Tf₂O/-Py/CH₂Cl₂/−42°, followed by treatment with NaCN/DMF at room temperature to yield the nitrile 002.

(2) Reduction of nitrile

Diisobutylaluminumhydride ("Dibal-H" 0.60 mL 0.60 mmol) was added to a solution of nitrile 001 (80.0 mg, 0,252 mmol) in methylene chloride (3.0 mL) cooled to −78° C. The reaction mixture was stirred for 2 h at −78° C. and then quenched by the addition of methanol (1 mL) followed by saturated aqueous ammonium chloride (1 mL). The mixture was diluted with ether (6.0 mL) and the resulting solution was warmed to room temperature. After 2 h at room temperature, a heterogeneous solution was obtained and the white precipitate was removed via filtration through a bed of Celite. The filtrate was washed with aqueous 1 N HCl (10 mL), saturated NaHCO₃ (20 mL) and brine (30 mL). The organic extract was then dried over solid sodium sulfate and the solvent removed in vacuo to provide the aldehyde 002 as a yellow oil (88 mg) which was used directly in the next step without further purification.

(3) Reduction of aldehyde

A solution of aldehyde 003 (80 mg, 0.25 mmol) in MeOH/CH$_2$Cl$_2$ (3:1; 4.0 mL) was cooled to 0° C. Sodium borohydride ("NaBH$_4$" 30 mg 0.79 mmol) was added in portions to this solution and the resulting mixture was stirred at 0° C. for 1 h. The mixture was then concentrated under reduced pressure and the resulting oil was partitioned between ethyl acetate (20 mL) and water (10 mL). The organic layer was removed, washed with brine, dried over Na$_2$SO$_4$ and concentrated in vacuo. The residual oil was purified by flash chromatography (hexanes/ethyl acetate; 3:2) to provide benzylether 004 (65 mg, 81% yield) as a colorless oil.

IR (film): 697, 1011, 1097, 1454, 1496, 2877, 2919, 3466 br, cm$^{-1}$.

$^1$H NMR (500 MHz, CDCl$_3$): δ1.12 (3H, d, J=7.2 Hz), 1.56 (1H, m), 1.63 (1H, ddd, J=4.1, 4.1, 15.8 Hz), 2.17-2.21 (2H, m), 2.41 (1H, br s), 2.57 (1H, ddd, J=2.0, 2.0, 15.8 Hz), 3.29 (1H, m), 3.41 (3H, s), 3.50 (1H, m), 3.72-3.85 (2H, m), 3.83-4.09 (1H, m), 4.10 (1H, m), 4.41 (1H, d, J=12.2 Hz), 4.78 (1H, d, J=12.2 Hz), 4.85 (1H, d, J=5.8 Hz).

HRMS calcd for C$_{18}$H$_{27}$O$_5$[M+H]+323.1858, found 323.1837.

[α]$_D$: −49.3° (C 0.41, MeOH).

Step b

(1) Hydrogenolysis of henzylether 004

A suspension of palladium hydroxide (Perleman's catalyst) in absolute ethanol (0.5 mL) was added to a solution of henzyl ether 004 (61 mg, 0.196 mmol) in absolute ethanol (2.5 mL) cooled to 0° C. An atmosphere of hydrogen gas was introduced using an inflated balloon and the resulting mixture was stirred at room temperature for 17 h. The suspension was filtered through Celite and the filtrate was concentrated in vacuo to provide alcohol (45 mg, 99% yield) as a colorless oil. Analysis of this product by NMR suggested no further purification was required.

(2) Preparation of trisilyated triol 005 from methyl glycoside 004

Ethanethiol (3 mL) was added to a solution of methyl glycoside 003 (43 mg, 0.186 mmol) in methylene chloride (3 mL) cooled to 0° C. Boron trifluoride etherate (0.1 mL, 0.80 mmol) was added and the mixture was stirred at 0° C. for 4 h. The reaction mixture was poured into a separatory funnel containing ice-cold ethyl acetate and saturated sodium bicarbonate solution. The aqueous layer was thoroughly extracted with ethyl acetate followed by methylene chloride and the combined organic extracts were dried by treatment of sodium sulfate. The organic solution was concentrated in vacuo and the residual oil purified by a short plug of silica (ethyl acetate) to provide the triol 004A (66 mg) as a yellow oil.

To a solution of the triol 004A (66 mg) in methylene chloride (2 mL) cooled to 0° C. was added triethylamine (0.15 mL, 1.1 mmol) followed by TBSOTf (0.128 mL, 0.55 mmol). The reaction mixture was stirred at 0° C. for 1 h and after this time additional triethylamine (0.15 mL, 1.1 mmol) and TBSOTf (0.128 mL, 0.55 mmol) was added. The mixture was warmed to room temperature and stirred for an additional 2 h. The reaction mixture was quenched by the addition of a saturated sodium bicarbonate solution and the resulting mixture was thoroughly extracted with ether. The combined organic extracts were washed with brine, dried over Na$_2$SO$_4$ and concentrated in vacuo. The residual oil was purified by flash chromatography (hexanes/ethyl acetate; 15:1) to provide the trisilyated triol 005 (96 mg, 70% yield from diol methyl glycoside) as a light yellow oil.

(3) Conversion of diethylthioacetal 005 to alcohol 006

Sodium bicarbonate (83.0 mg, 0.97 mmol) followed by iodine (83.0 mg, 0.327 mmol) was added to a solution of diethyl thioacetal 005 (138 mg, 0.218 mmol) in acetone/water (9:1) at 0° C. After 2.5 h, further quantities of sodium bicarbonate (4.5 eq) and iodine (1.5 eq) were added and the mixture was stirred for an additional 1 h. The reaction mixture was diluted with ethyl acetate (20 mL) and the resulting solution washed with saturated aqueous sodium thiosulfate, saturated aqueous NaHCO$_3$, and brine. The organic solution was dried with sodium sulfate and concentrated under reduced pressure to afford 137 mg of the crude aldehyde 004A which was used directly in the next step.

To a solution of the aldehyde (137 mg) in methanol/methylene chloride (15 mL; 2:1) at 0° C. was added sodium borohydride (50 mg) in portions. The solution was stirred at 0° C. for 30 min, then concentrated under reduced pressure. The residual oil was partitioned between ethyl acetate (50 mL) and water (20 mL) and the organic layer was washed with brine, dried over solid Na$_2$SO$_4$ and concentrated in vacuo. The crude oil was purified by flash chromatography (hexanes:ethyl acetate, 3:1) to provide alcohol 006 (106 mg, 93% yield) as a colorless oil.

(4) Synthesis of nitrile 008

Methanesulfonyl chloride (60 mL, 0.774 mmol) was added to a solution of alcohol 006 and triethylamine (125 mL, 0.838 mmol) in methylene chloride (5.0 mL) and the reaction mixture was stirred at room temperature for 10 min. The mixture was diluted with methylene chloride (20 mL) and quenched by the addition of saturated aqueous ammonium chloride (20 mL). The organic extract was washed with aqueous sodium bicarbonate followed by brine, dried over solid Na$_2$SO$_4$, and concentrated in vacuo. The crude oil (400 mg) was used directly in the next step without further purification.

Sodium cyanide (350 mg) was added to a solution of mesylate (400 mg) in DMSO (4 mL) and the mixture was stirred at 60° C. for 3 h. The reaction mixture was cooled to room temperature and diluted with ice-cold brine. The mixture was exhaustively extracted with ethyl acetate and the combined organics were washed with brine, dried over Na$_2$SO$_4$, and concentrated in vacuo. The residual oil was purified by flash chromatography (hexanes/ethyl acetate; 9:1) to afford the nitrile 008 (338 mg, 92% yield).

IR (film): 772, 837, 1006, 1019, 1030, 1100, 1255, 1386, 1463, 1472, 2125, 2857, 2884, 2929, 2955 cm$^{-1}$.

$^1$H NMR (500 MHz, CDCl$_{3l}$): δ0.02 (9H, s), 0.04 (3H, s), 0.05 (3H, s), 0.09 (3H, s), 0.86 (9H, s), 0.88 (9H, s), 0.89 (9H, s), 1.04 (3H, d, J=6.7 Hz), 1.49 (1H, m), 1.84 (1H, ddd, J =4.2, 4.4, 10.6 Hz), 1.93 (1H, m), 2.00 (1H, d, J=14.9 Hz), 2.30 (1H, m), 2.46 (1H, dd, J=7.5, 16.7 Hz), 2.60 (1H, dd, J=3.2, 16.6 Hz), 2.94 (1H, d, J=8.9 Hz), 3.42 (1H, d, J=10.2 Hz), 3.60 (1H, m), 3.69-3.73 (2H, m), 3.81 (1H, m).

HRMS calcd for $C_{29}H_{62}O_4Si_3N$ [M +H]+572.3986, found 572.3997.

$[\alpha]_D$: −0.87° (C 1.95, MeOH).

(5) Preparation of aldehyde 009 from nitrile 008

A solution of diisobutylaluminum hydride in hexanes (1.0 M, 2.5 mL, 2.5 mmol) was added dropwise to a stirred solution of nitrile 008 (310 mg, 0.543 mmol) in methylene chloride (5 mL) cooled to −78° C. The reaction mixture was stirred for an additional 1.5 h and quenched by the consecutive addition of methanol (6 mL), a saturated ammonium chloride solution (6 mL) and ether (6 mL). The mixture was warmed to room temperature and stirred for an additional 1 h. The mixture was filtered through Celite and the Celite pad was washed with ether. The filtrate was washed with a saturated ammonium chloride solution (20 mL) followed by brine, dried over solid $Na_2SO_4$, and concentrated in vacuo. The residual oil was purified by flash chromatography (hexanes/ethyl acetate; 9:1) to afford the aldehyde 009 (296 mg, 96% yield) as a colorless oil.

Step c

Compound 105, a bromide, was synthesized according to the following procedure. The bromide will eventually be reacted with aldehyde 009 to yield compound 12. The bromide was synthesized from (S)-(+)-methyl 3-hydroxy-2-methylpropionate 100 (Aldrich) in approximately 40% overall yield, in several steps:

(1) Conversion of β-hydroxy ester 100 to alcohol 101 p-Toluenesulfonic acid (80 mg, 0.42 mmol) was added to a solution of alcohol 100 (21.0 g, 0.177 mol) and dihydropyran (26 mL, 0.284 mol) in ethyl ether (180 mL) and the mixture was stirred at room temperature for 20 h. The reaction mixture was quenched by the addition of a saturated sodium bicarbonate solution and the resulting mixture was thoroughly extracted with ether. The combined organics were washed with brine, dried over solid $Na_2SO_4$ and concentrated in vacuo to provide 40 g of the THP ether 100A. The crude product was used directly in the next step without further purification.

Lithium aluminum hydride (10.0 g, 0.263 mol) was added slowly over 1 h to an ice-cold solution of ether. The ester 100A (40 g) in ether (200 mL) was then added dropwise to the slurry and the resulting mixture was stirred at 0° for 12 h. The reaction mixture was quenched by the successive addition of ethyl acetate (40 mL), water (40 mL), 1 N sodium hydroxide solution (40 mL) and water (40 mL). The resulting slurry was filtered through Celite and the Celite pad was washed with ether. The filtrate was washed with brine and the organic extract dried over solid $Na_2SO_4$, and concentrated in vacuo. The residual oil was purified by vacuum distallation to afford the alcohol 101 (29.0 g, 94% yield), b.p. 105° C. (0.1 Torr).

(2) Swern oxidation of alcohol 101

Oxalyl chloride (12.0 mL, 0.137 mol) was added to methylene chloride (60 mL) cooled to −78° C. A solution of dimethyl sulfoxide (13 mL, 0.183 mol) in methylene chloride (30 mL) was then added dropwise over 15 min. A solution of alcohol 101 (16.0 g, 0.091 mol) in methylene chloride (30 mL) was added dropwise over 20 min and the resulting mixture was stirred for 30 min at −78° C. A solution of triethylamine (64.1 mL, 0.459 mol) in methylene chloride (30 mL) was then added and the mixture was stirred for 30 min at −78° C. The reaction mixture was them removed from the cooling bath and warmed to 0° C. over 15 min. The reaction slurry was then partitioned between benzene/ether (600 mL; 4:1) and water (800 mL). The organic layer was removed and washed with water (2×500 mL) and brine. The organic extract was then dried over solid $Na_2SO_4$ and concentrated in vacuo to provide 15.8 g of the aldehyde 102 as a light yellow oil. The crude aldehyde was used immediately in the next step without further purification.

(3) 1,2-Addition to aldehyde 102

A solution of butyllithium in hexanes (50.0 mL, 0.105 mol) was added to a solution of trimethylsilylacetylene in ether (400 mL) at −78° C. The mixture was warmed to 30° C. and stirred for 30 min. The solution was cooled to −78° C. and a solution of aldehyde 101 (14.0 g, 0.091 mol) in ether (30 mL) was added dropwise over 20 min. The reaction mixture was maintained for 1 h at −78° C. and quenched by the addition of a saturated ammonium chloride solution. The resulting mixture was warmed to 0° C. and exhaustively extracted with ethyl ether. The combined organic extracts were washed with brine, dried over solid $Na_2BO_4$ and concentrated in vacuo. The residual oil (22 g) was purified by flash chromatography (hexanes/chloroform/ethyl acetate; 10:4:1) to provide 5.5 g of desired alcohol, 7.1 g of mixed fractions and 6.1 g of undesired alcohol (55% overall yield from alcohol 101).

(4) MPM protection of propargyl alcohol 103

A solution of propargyl alcohol (2.0 g, 7.40 mmol) in methylene chloride (10 mL) was added to a solution p-methoxybenzyltrichloroimidate in methylene chloride (500 mL) cooled to 0° C. A solution of boron trifluroetherate in methylene chloride (0.2 N, 0.7 mL, 0.14 mmol) was added dropwise and the initially yellow solution took on an orange color. After 10 min, TLC analysis indicated the reaction was complete. The reaction mixture was quenched by the addition of a saturated sodium bicarbonate solution. The organic layer was removed and the remaining aqueous layer was thoroughly extracted with methylene chloride. The combined organic extracts were washed with brine, dried over solid $Na_2SO_4$ and concentrated in vacuo. The residual solid was dissolved in equal amounts of benzene and hexanes and applied to a column of silica. Gradient elution with hexanes/ethyl acetate (50:1, 50:5) provided the protected alcohol 104 (2.49 g, 83% yield) as a light yellow oil.

(5) Solvolsis of THP-protected alcohol 104

Camphorsulfonic acid (100 mg, 0.43 mmol) was added to a solution of THP ether 104 (2.0 g, 4.9 mmol) in methanol (50 mL). The reaction mixture was stirred at room temperature for 9.5 h, then quenched by the addition of solid sodium bicarbonate (36 mg, 0.43 mmol). The mixture was stirred for 20 min, then concentrated in vacuo. The residual oil was partitioned between ether (40 mL) and water (20 mL) and the organic extract was washed with brine, dried over solid $Na_2SO_4$, and concentrated in vacuo. The residual oil was purified by flash chromatography (hexanes/ethyl acetate; 9:1) to provide the alcohol 104 (1.3 g, 87% yield) as a colorless oil.

(6) Conversion of alcohol 104 to bromide 105

Triethylamine (0.228 mL, 1.52 mmol) was added to a solution of alcohol 104 (380 mg, 1.17 mmol) in methylene chloride (5 mL) cooled to 0° C. Methanesulfonyl chloride was added and the solution was stirred for 30 min at 0° C. The reaction mixture was then diluted with methylene chloride (20 mL) and quenched by the addition of a saturated ammonium chloride solution (30 mL). The organic layer was washed consecutively with a 0.3 N HCl solution (20 mL), saturated sodium bicarbonate solution, and brine. The organic solution was then dried over solid $Na_2SO_4$, and concentrated in vacuo. The crude oil (470 mg) was used directly in the next step without further purification.

Lithium bromide (1.02 g, 11.7 mmol) was added to a solution of mesylate 104A (470 mg) in THF (10 mL) at room temperature. The reaction mixture was stirred for 2 h at reflux, then cooled to room temperature and transferred to a separatory funnel containing ether (40 mL) and water (30 mL). The organic layer was removed, washed with brine, dried over solid $Na_2SO_4$, and concentrated in vacuo. The residual oil was purified by flash chromatography to provide the bromide 105 (418 mg, 93% yield) as a light yellow oil.

IR (film): 760, 843, 1023, 1037, 1073, 1251, 1514, 1612, 2168, 2835, 2936, 2961 $cm^{-1}$.

$^1$H NMR (500 MHz, $CDCl_3$): δ0.18 (3H, s), 1.11 (3H, d, J=6.7 Hz), 2.11 (1H, m), 3.46–3.52 (2H, m), 3.78 (3H, s), 4.04 (1H, d, J=7.1 Hz), 4.41 (1H, d, J=11.1 Hz), 4.70 (1H, d, J=11.1 Hz).

HRMS calcd for $C_{17}H_{25}O_2Br$ [M]+368.0807, found 368.0810.

$[\alpha]_D$: −70.6° (C 1.33, MeOH).

Step d (1) Coupling of Bromide 105 and aldehyde 009

A solution of t-butyllithium (0.71 mL, 1.21 mmol) in hexane was added to a solution of bromide 105 (249 mg, 0.674 mmol) in ether at −78° C. The solution was stirred for 20 min at −78° C and after this time a solution of the aldehyde 009 (73 mg, 0.127 mmol) in ether (3 mL) was added via cannula over 1 min. The reaction mixture was stirred for 30 min at −78° C., then quenched by the addition of saturated ammonium chloride (20 mL). The resulting mixture was warmed to room temperature, then exhaustively extracted with ether. The combined organic extracts were washed with brine, dried over solid $Na_2SO_4$, and concentrated in vacuo. The residual oil was purified by flash chromatography (hexanes/ethyl acetate; 9:1) to provide alcohol 011 (94 mg, 86% yield) as a mixture of diastereoisomers.

(2) Deprotection of TMS protected alkyne 011

A solution of silver nitrate (256 mg, 1.51 mmol) in absolute ethanol (10 mL) and water (6.0 mL) was added dropwise over 15 min to a solution of protected alkyne 011 (227 mg, 0.262 mmol) in absolute ethanol (41 mL) and HMDS (0.387 mL, 1.83 mmol). The reaction mixture was stirred for 2 h at room temperature, then quenched by the addition of sodium iodide (472 mg, 3.14 mmol) in ether (20 mL). The mixture was filtered through Celite and the Celite pad was washed with ether. The filtrate was concentrated and the residue partitioned between ether (30 mL) and water. The organic layer was washed with brine, dried over solid $Na_2SO_4$ and concentrated in vacuo. The residual oil was purified by flash chromatography (hexanes/ethyle acetate; 4:1) to provide the terminal alkyne 012 (206 mg, 99% yield) as a colorless oil.

(3) Preparation of vinyl stannane 012A

A solution of alkyne 012 (45 mg, 0.057 mmol) and AIBH (5 mg) in toluene (3 mL) and tributyltin hydride (0.3 mL) was stirred at 80° C. After 1 h, tributyltin hydride (0.4 mL) was added and the solution was stirred for an additional 1 h. The mixture was cooled to room temperature and concentrated in vacuo. The residual oil was purified by flash chromatography (hexanes/ethyl acetate; 5:1) to provide vinyl stannane 012A (56 mg, 92% yield) as a mixture of geometric isomers (trans:cis, 9:1).

(4) Preparation of vinyl iodide 013

A solution of iodine (15 mg, 0.059 mmol) in methylene chloride (1 mL) was added dropwise to a solution of vinyl stannane 012A (56 mg, 0.0517 mmol) in methylene chloride (4 mL) cooled to 0° C. The light pink solution was stirred for 10 min at 0° C., then diluted with methylene chloride (20 mL). The resulting mixture was washed with a sodium thiosulfate solution (30 mL) and brine. The organic extract was then dried over solid $Na_2SO_4$ and concentrated in vacuo. The residual oil was purified by flash chromatography (hexanes/ethyl acetate; 5:1) to afford the vinyl iodide 013 (44 mg, 94% yield) as a light yellow oil.

(5) Dess-Martin oxidation of alcohol 014

Dess-Martin periodane (100 mg, 0,235 mmol) was added in portions to a solution of alcohol 014 (44 mg, 0.048 mmol) in methylene chloride cooled to 0° C. Sodium bicarbonate (8.0 mg) was then added and the solution was stirred at 0° C. for 2 h. The mixture was diluted with ether (10 mL) and quenched by the addition of a saturated sodium bicarbonate solution (8 mL) containing 4 dissolved crystals of sodium thiosulfate. The solution was vigorously stirred for 1 h. The mixture was then thoroughly extracted with ether and the combined organic extracts were washed with brine and dried over solid $Na_2SO_4$. The solvent was removed in vacuo and the residual oil was purified by flash chromatography (hexanes/ethyl acetate; 4:1) to provide the aidehyde, compound 12, (40 mg, 91% yield) as a colorless oil.

SYNTHESIS OF HALICHONDRIN-RELATED COMPOUNDS

There are numerous ways to attach modified left halves on the right half of compound 10 or its C.35 stereoisomer. Scheme 5 below shows five of these possibilities with the representative experimental procedures given below. These coupling reactions can be applied for the nor right half 18 or its C.35 stereoisomer as well. In addition, using the steps a and b, C.35 and C.38 diesters and diethers can be prepared from 10, 18, and their C.35 stereoisomers.

Scheme 5

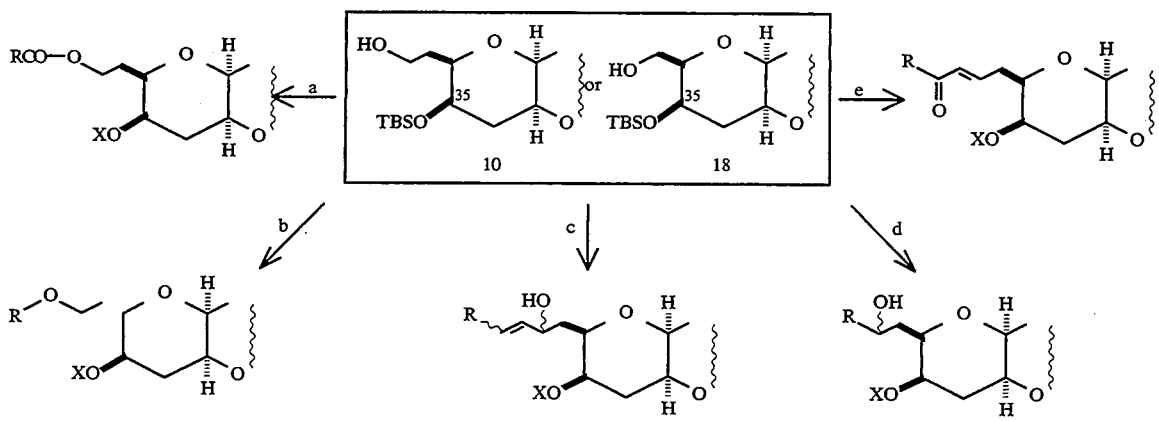

An example for acylation (step a)

To a solution of compound 10 (2.0 mg/0.1 mL of anhydrous $CH_2Cl_2$) were added $TBSO(CH_2)_7CO_2H$ (1.0 mg), DCC (1.0 mg) and DMAP (ca. 0.01 mg) at 0° C. After stirring overnight at room temperature, the reaction mixture concentrated under reduced pressure, and the residue was purified by PTLC (hexanes/ethyl acetate 1:2), to give the ester (2.3 mg, 91% yield) as a clear oil.

An example for etherification (step b)

To a solution of compound 10 (2.0 mg/0.1 mL of anhydrous THF) were added NaH (5% mineral oil dispersion, 1.08 mg) and a trace amount of imidazole at 0° C. The mixture was stirred for 30 minutes at 0° C. and then for 15 minutes at room temperature. $MeO_2C(CH_2)_7OSO_2Me$ (1.14 mg/0.1 mL of anhydrous THF) was added to this solution dropwise at 0° C. After stirring for 2 h at 0° C., the reaction was quenched by addition of a drop of methanol. The reaction mixture was diluted with $CH_2Cl_2$ and washed with brine. The organic layer was separated, dried ($Na_2SO_4$) and concentrated under reduced pressure. The residue was purified by PTLC (hexanes/ethyl acetate 1:2), to give the ether (1.53 mg, 65% yield) as a clear oil.

Examples for Ni(II)/Cr(II)-mediated coupling (step c)

See the text under the subheadings Compound 1 and Compound 2 above.

An example for cuprate coupling (step d)

To a stirred solution of $TBSO(CH_2)_8I$ (370 mg, 1.0 mmol) in pentane (4 mL), was added t-BuLi (1.7 M solution in pentane, 1.17 mL, 2.0 mole) dropwise at −78° C. After 10 min, lithum 2-thienylcyanocuprate (0.25 M solution in THF, 4.0 mL, 1.07 mmole) was added dropwise at −78° C. The resulting cloudy solution was stirred for 10 min at 78° C., then slowly warmed to −10° C. over 0.5 h. Approximately 0.1 ml of the reagent solution thus prepared was transferred to a samll flask, then cooled to −30° C. To this solution was added the aldehyde prepared from compound 10 (2.0 mg/0.05 mL of THF; see the text under the subheading Compound 1 above). The reaction mixture was stirred at 0° C. for 1 h then warmed to room temperature. The reaction was quenched with 10:1 (v/v) $NH_4Cl/NH_4OH$ solution, diluted with EtOAc, and washed with brine. The organic layer was dried ($MgSO_4$) and concentrated under reduced pressure. The residue was purified by PTLC (hexanes/ethyl acetate 1:2), to give the alcohols (1.75 mg, 69% yield) as a slightly yellow oil

An example for Horner-Emmons reaction (step e)

A ketophosphonate $TBSO(CH_2)_7COCH_2P(O)(OMe)_2$ (2.58 mg/0.1 mL of anhydrous THF) was added to a suspention of NaH (5.0% in mineral oil, 2.17 mg) in THF (0.1 mL). After stirring for 35 min at room temperature under Ar, the mixture was cooled in an ice bath, and a THF solution of the aldehyde prepared from compound 10 (2.0 mg/0.1 mL of THF; also see the text under the subheading Compound i above) was added dropwise. Stirring was continued for 30 min at 0° C. and 30 min at room temperature. The reaction mixture was diluted with ether, applied to a short pad of silica gel, and eluted with ethyl acetate. The solvent was removed, and the residue was purified by PTLC (hexanes/ethyl acetate 1:2), to give the enone (1.22 mg, 47% direct yield).

DETERMINATION OF ANTI-TUMOR ACTIVITY (1) In vitro growth inhibitory property

Synthetic halichondrin B I was tested in growth inhibition assays against several different tumor cell lines to obtain $IC_{50}$ values. See Table 1 below. For comparison, the National Cancer Instititute reported growth inhibitory effects of natural halichondrin B against L1210 murine leukemia cells at $IC_{50}=0.3$ nM [J. Biol. Chem. 266:15882–15889 (1991)] and Hirata and Uemura reported $IC_{50}=0.08$ nM against B-16 murine melanoma cells [Pure Appl. Chem. 58:701–710 (1986)]. Both references are hereby incorporated in their entirety.

TABLE 1

| IN VITRO GROWTH INHIBITION BY SYNETHETIC HALICHONRDIN B 1 | | | |
|---|---|---|---|
| Cell line | Species | Type | $IC_{50}$, nM |
| LOX | human | melanoma | 0.08 |
| HT-1080 | human | fibrosarcoma | 0.01 |
| HL-60 | human | monocytic lekemia | 0.12 |
| HT-29 | human | colon carcinoma | 0.19 |
| DK-1 | human | ras-transforming fibroblasts | 0.18 |
| SK-OV-3 | human | ovarian carcinoma | 0.12 |
| Caov-3 | human | ovarian carcinoma | 0.25 |
| OVCA 433 | human | ovarian carcinoma | 0.16 |
| NIH:OVCAR-3 | human | ovarian carcinoma | 0.06 |
| MCF-7 | human | breast carcinoma | 0.20 |

TABLE 1-continued

IN VITRO GROWTH INHIBITION BY SYNETHETIC HALICHONRDIN B 1

| Cell line | Species | Type | $IC_{50}$, nM |
|---|---|---|---|
| MG-63 | human | osteosarcoma | 0.13 |

Figure 3:
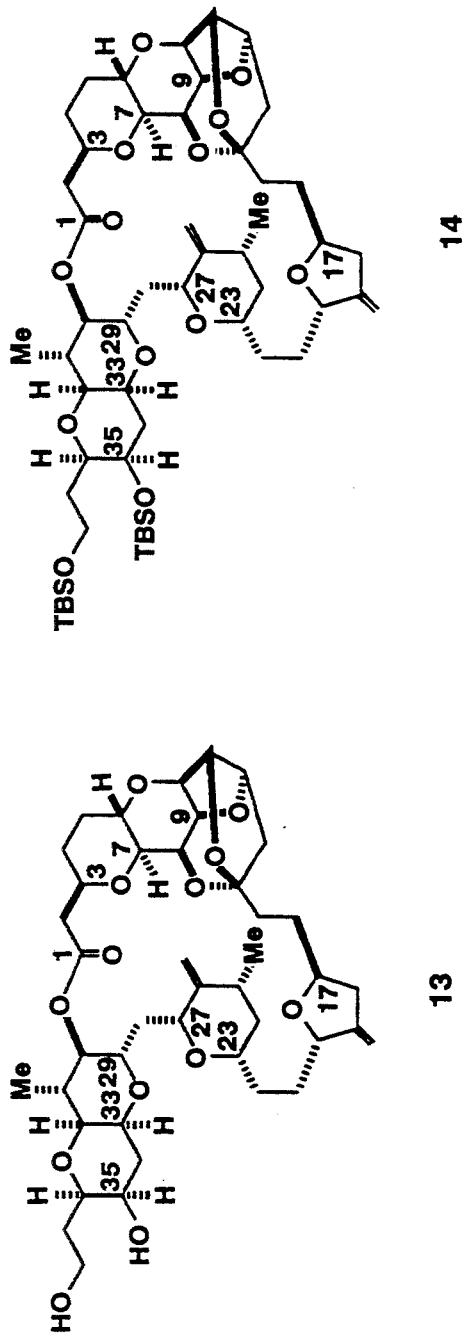
FIG. 3 shows the structures of four tested halichondrin-related compounds.
Figure 3:
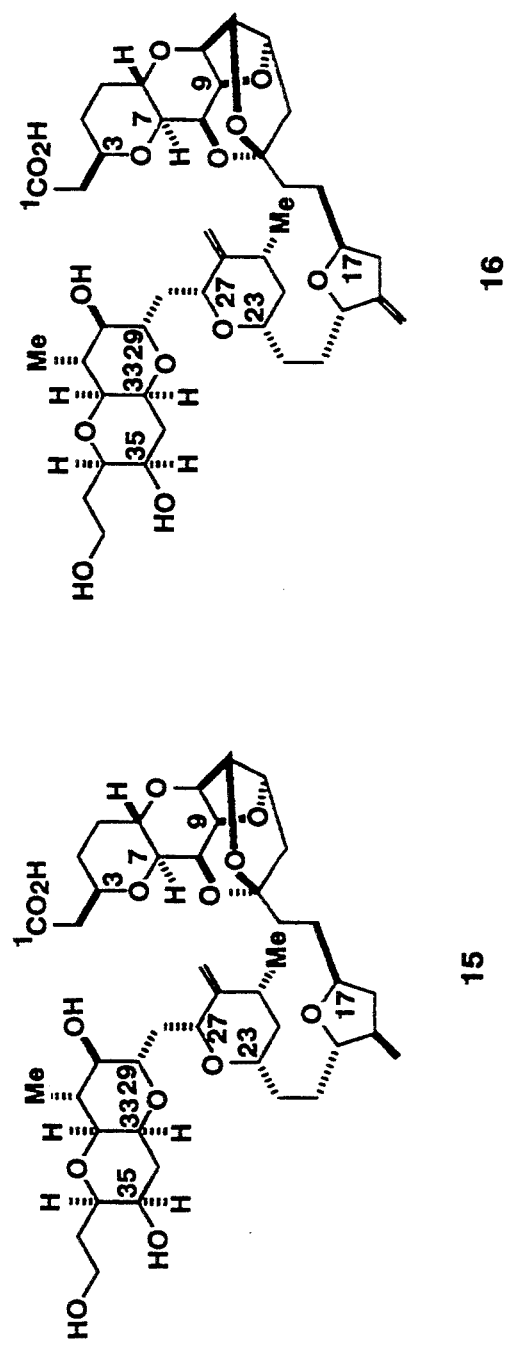

In addition, several synthetic halichondrin-related compounds were tested. As examples, both compounds 13 and 14 possessed significant growth inhibitory potency against LOX and HT-1080 cells, while compounds 15 and 16 did not show significant activity (Table 2). For the structures of compounds 13–16, see FIG. 3.

TABLE 2

IN VITRO GROWTH INHIBITION BY SYNTHETIC COMPOUNDS 13, 14*

| Cell line | Species | Type | 13 | 14 |
|---|---|---|---|---|
| LOX | human | melanoma | 0.73 | 2.3 |
| HT-1080 | human | fibrosarcoma | 0.31 | 1.6 |

*$IC_{50}$, in nM (2) In vivo anti-tumor effects of synthetic halichondrin B

In vivo anti-tumor effects of synthetic halichondrin B I was demonstrated by using LOX melanoma on nude mice. The ability of 25 μg/kg halichondrin B to inhibit growth of subcutaneous LOX human melanoma tumors in both female and male nude mice (20 females, 20 males; 10 each sex control and HB-treated) was demonstrated as follows.

Mice received $1 \times 10^6$ LOX cells via s.c. injection on day 0, with complete injection randomization across sexes and treatment groups. On days 3–7 and 10–14, male and female experimental mice received 25 μg/kg of synthetic halichondrin B 1 via i.p. injection in saline; controls received saline alone. Halichondrin B treatment prevented tumor growth almost completely in both sexes. These results cannot be explained by variable cell inoculation, since tumor onset was essentially simultaneous on day 3 in all 4 groups, reaching 90–100% penetrance by day 6. Tumors in the halichondrin B-treated mice simply failed to grow after an initial period of development into visible but very small tumors. One female halichondrin B-treated mouse completely lost her tumor on day 14; this loss persisted until the end of the experiment on day 17. Importantly, after the initial development period, tumors in halichondrin B-treated mice actually regressed.

Other Embodiments

From the above description, one skilled in the art can easily ascertain the essential characteristics of the present invention, and without departing from the spirit and scope thereof, can make various changes and modifications of the invention to adapt it to various usages and conditions. For example, the total carbon number of A and B in the formula on page 2 can be 40, 50 or higher (not Counting any alcohol protecting groups). Also, in the same formula, the number of carbons embraced by ()m and ()n ranges from 0–3. The same situation can also apply to other formulas set forth in this disclosure.

Thus, other embodiments are also within the claims.

What is claimed is:

1. A compound of the following structure:

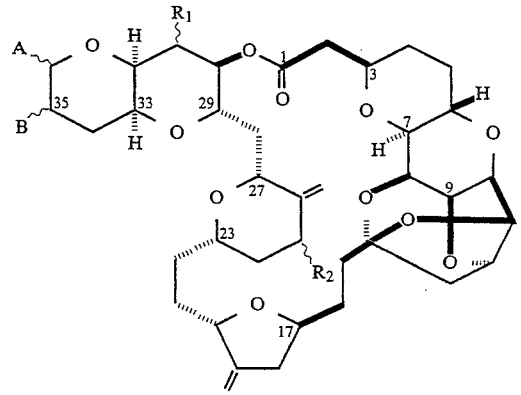

in which each of $R_1$ and $R_2$ is H- or $C_{1-6}$ alkyl; and each of A and B is H-, HO- with or without an alcohol protecting group, an unsubstituted hydrocarbon, or a substituted hydrocarbon with or without an alcohol protecting group; wherein the total carbon number of A and B ranges from 0–18, not counting the carbons in any alcohol protecting groups, and said alcohol protecting group is $R_5$-O-, $R_5$-CO-O-, $R_5$-O-CO-O-, or

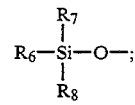

$R_5$ being $C_{1-10}$ alkyl, $C_{2-10}$ alkenyl, $C_{2-10}$ alkynyl, $C_{7-20}$ aralkyl, $C_{7-20}$ alkaryl, phenyl or tetrahydropyranyl, and each of $R_6$, $R_7$ and $R_8$ being $C_{1-6}$ alkyl, $C_{2-6}$ alkenyl or phenyl.

2. The compound of claim 1, wherein each of A and B is HO-, HO- linked to said alcohol protecting group, or a substituted hydrocarbon selected from the group consisting of $R_3$-CO-$R_4$-, $R_3$-CH(OH)-$R_4$-, $R_3$-H(OH)-$R_4$- linked to said alcohol protecting group, $R_3$-O-CO-, $R_3$-O-CO-$R_4$-, HO-$R_4$-, and HO-$R_4$- linked to said alcohol protecting group; each of $R_3$ and $R_4$ being alkyl, alkenyl or alkynyl.

3. The compound of claim 2, wherein the total carbon number of A and B ranges from 0–15, not counting the carbons in any alcohol protecting groups.

4. The compound of claim 3, wherein the total carbon number of A and B ranges from 0–12, not counting the carbons in any alcohol protecting groups 5. The compound of claim 2, wherein each of A and B is HO-, HO- linked to said alcohol protecting group, HO-$R_4$-, or HO-$R_4$- linked to said alcohol protecting group.

6. The compound of claim 5, wherein B is HO- or HO- linked to said alcohol protecting group.

7. The compound of claim 6, wherein A is HO-$R_4$- or HO-$R_4$- linked to said alcohol protecting group.

8. The compound of claim 2, wherein the stereochemistries of C.25, C.31, C.35 and C.36 are R, S, R and R, respectively.

9. The compound of claim 7, wherein the stereochemistries of C.25, C.31, C.35 and C.36 are R, S, R and R, respectively.

10. The compound of claim 2, wherein the stereochemistries of C.25, C.31, C.35 and C.36 are S, R, S and S, respectively.

11. The compound of claim 7, wherein the stereochemistries of C.25, C.31, C.35 and C.36 are S, R, S and S, respectively.

* * * * *

UNITED STATES PATENT AND TRADEMARK OFFICE
CERTIFICATE OF CORRECTION

PATENT NO. : 5,436,238

DATED : July 25, 1995

INVENTOR(S) : Yoshito Kishi et al.

It is certified that error appears in the above-identified patent and that said Letters Patent is hereby corrected as shown below:

Cover page, right column, line 10, replace "9" with --(--.

Page 2, left column, replace "Access" with --Acces--.

Col. 1, lines 27-28, delete the first occurrence of "homohalichondrin B".

Col. 1, line 45, add --B⌇-- to $C_{35}$ of the formula.

Col. 2, line 38 should read: $CH_2=CH-CH_2-O-CO-O-$.

Col. 2, line 47, replace "conovalent" with --monovalent--.

Col. 3, line 45, replace "$R_5$" with --$R_8$--.

Col. 4, line 1, replace "of", second occurrence, with --or--.

Col. 5, line 23, replace ">C(SCH$_3$)" with -->C(SCH$_3$)$_2$--.

Col. 6, line 58, after "$C_{1-5}$" insert a space.

Col. 8, top formula, the bar between the third oxygen atom from the right and the first carbon atom to its left should be bold.

Col. 7, formula above 3($\alpha_D$-27.2°), add double bar to the lower left carbon atom.

Col. 9, last formula, the bar between the third oxygen atom from the right and the first carbon atom to its left should be bold.

UNITED STATES PATENT AND TRADEMARK OFFICE
CERTIFICATE OF CORRECTION

PATENT NO. : 5,436,238

DATED : July 25, 1995

INVENTOR(S) : Yoshito Kishi et al.

It is certified that error appears in the above-identified patent and that said Letters Patent is hereby corrected as shown below:

Col. 11, last formula, right side, replace "36" with --35--.

Col. 12, line 6, replace "S" with --8--.

Col. 12, line 7, put the word "trans" in italic type.

Col. 12, line 16, replace "p-TsOH·Py" with --p-TsOH•Py--.

Col. 12, line 16, replace "1H" with --$^{1}$H--.

Col. 12, line 21, replace "5-6:1" with --5:1 to 6:1--.

Col. 12, line 29, underline "Compound 10".

Col. 12, line 33, put the word "trans" in italic type.

Col. 12, line 54, replace "B1" with --B 1--.

Col. 15, line 21, replace "(M+)" with --(M$^{+}$)--.

Col. 16, line 7, replace "C" with --c--.

Col. 16, line 20, replace "get" with --gel--.

Col. 18, line 22, replace "19g" with --1.9g--.

Col. 18, line 27, after "606cm$^{-1}$" insert a comma.

Col. 18, line 29, replace "OAC" with --OAc--.

Col. 18, line 30, replace "OAC" with --OAc--.

UNITED STATES PATENT AND TRADEMARK OFFICE
CERTIFICATE OF CORRECTION

PATENT NO. : 5,436,238

DATED : July 25, 1995

INVENTOR(S) : Yoshito Kishi et al.

It is certified that error appears in the above-identified patent and that said Letters Patent is hereby corrected as shown below:

Col. 18, line 37, replace "C1.81" with --c1.81--.

Col. 18, line 53, replace "$BF_3.OEt_2$" with --$BF^3 \cdot OEt_2$--.

Col. 18, line 62, after "702 $cm^{-1}$" insert a comma.

Col. 18, line 65, replace "J.4.5" with --J=4.5--.

Col. 19, line 3, replace "C1.25" with --c1.25--.

Col. 20, line 15, after "703 $cm^{-1}$" insert a comma.

Col. 20, line 50, insert a period after "(10mL)".

Col. 21, line 27, insert a comma after "$cm^{-1}$".

Col. 21, line 35, replace "(C1.1,)" with --(c1.1,)--.

Col. 22, line 12, insert a comma after "$cm^{-1}$".

Col. 22, line 15, delete "m)".

Col. 22, line 15, replace "(9H, S)," with --(9H, s)--.

Col. 22, line 15, insert --m-- after "(2H,".

Col. 22, line 21, replace "C 5.91" with --c 5.91--.

Col. 22, line 22, replace "calcl" with --calcd--.

Col. 22, line 48, delete ")" after "$Na_2SO_4$".

Col. 22, line 53, insert a comma after "$cm^{-1}$".

UNITED STATES PATENT AND TRADEMARK OFFICE
CERTIFICATE OF CORRECTION

PATENT NO. : 5,436,238

DATED : July 25, 1995

INVENTOR(S) : Yoshito Kishi et al.

It is certified that error appears in the above-identified patent and that said Letters Patent is hereby corrected as shown below:

Col. 22, line 66, replace "(C 1.43," with --(c 1.43,--.

Col. 23, line 32, insert a comma after "$cm^{-1}$".

Col. 23, line 41, replace "(C 1.15," with --(c 1.15,--.

Col. 24, line 66, insert a period between 1 and 2 --(1.2 eq)--.

Col. 25, line 34, insert a comma after "$cm^{-1}$".

Col. 25, line 40, replace "(C4.9,)" with --(c4.9,)--.

Col. 26, line 34, insert --88%-- before "yield"

Col. 26, line 68, insert a comma after "$cm^{-1}$".

Col. 27, line 47 insert a comma after "$cm^{-1}$".

Col. 28, line 33, insert a comma after "$cm^{-1}$".

Col. 28, line 39, replace "$C_{21}H_{35}O_{41}$" with --$C_{21}H_{35}O_4I$--.

Col. 29, line 5, insert a comma after "$cm^{-1}$".

Col 29, line 19, replace "wt" with --et--.

Col. 29, upper left formula, replace "HO⌒" with -- HO⌒ --.

Col. 31, line 63, insert --$I_2$-- before "(59.25g,)".

Col. 34, line 67, replace "3,685" with --3.685--.

UNITED STATES PATENT AND TRADEMARK OFFICE
CERTIFICATE OF CORRECTION

PATENT NO.  : 5,436,238

DATED       : July 25, 1995

INVENTOR(S) : Yoshito Kishi et al.

It is certified that error appears in the above-identified patent and that said Letters Patent is hereby corrected as shown below:

Col. 35, line 34, in the formula, the bended bold bar should be straight, connecting the two carbon atoms.

Col. 35, line 64, delete "m " after the comma.

Col. 38, line 14, replace "$BF_3.OEt_2$" with --$BF_3 \cdot OEt_2$--.

Col. 38, line 46, replace "HF.pyridine" with --HF·pyridine--.

Col. 41, line 24, insert a comma after "$cm^{-1}$".

Col. 41, line 36, replace "C 0.99" with --c 0.99--.

Col. 42, line 1, replace "aldhyde" with --aldehyde--.

Col. 43, top formula, insert boldface line between the first H from right and the carbon atom above it.

Col. 43, line 42, insert a comma after "$cm^{-1}$".

Col. 43, line 44, replace "C 3.3" with --c 3.3--.

Col. 43, line 45, replace "$C_{541} H92O_{10}Si_2$" with --$C_{54}H_{92}O_{10}Si_2$--.

Col. 44, line 53, replace "113 3" with --113.3--.

Col. 45, line 55, insert "0°C" after "at".

Col. 46, second formula, replace "HO⁄ " with --HO⁄ --.

Col. 46, line 56, replace "C 6.65" with --c 6.65--.

UNITED STATES PATENT AND TRADEMARK OFFICE
CERTIFICATE OF CORRECTION

PATENT NO.   : 5,436,238

DATED        : July 25, 1995

INVENTOR(S) : Yoshito Kishi et al.

It is certified that error appears in the above-identified patent and that said Letters Patent is hereby corrected as shown below:

Col. 47, line 29, insert a comma after "cm$^{-1}$".

Col. 47, line 40, replace "C 2.86" with --c 2.86--.

Col. 48, line 19, insert a comma after "cm$^{-1}$".

Col. 48, line 22, replace "S", both occurrences, with --s--.

Col. 48, line 30, replace "C 9.99" with --c 9.99--.

Col. 49, line 2, before "L-" insert "α,β-".

Col. 49, line 4, replace "C 1.3" with --c 1.3--.

Col. 49, line 49, replace "-" with a period.

Col. 49, line 52, insert a comma after "cm$^{-1}$".

Col. 49, line 55, replace "3.91" with --3.91--.

Col. 49, line 65, replace "1HNMR" with --$^{1}$HNMR--.

Col. 49, line 68, insert --53:-- after "Chem.".

Col. 50, line 31, replace "ethyle" with --ethyl--.

Col. 50, line 33, replace "16,207" with --16.207--.

Col. 50, line 34, insert a comma after "cm$^{-1}$".

Col. 50, line 49, replace "C 0.81" with --c 0.81--.

Col. 51, line 21, insert a comma after "cm$^{-1}$".

UNITED STATES PATENT AND TRADEMARK OFFICE
CERTIFICATE OF CORRECTION

PATENT NO. : 5,436,238

DATED : July 25, 1995

INVENTOR(S) : Yoshito Kishi et al.

It is certified that error appears in the above-identified patent and that said Letters Patent is hereby corrected as shown below:

Col. 51, line 35, replace "C 0.93" with --c 0.93--.

Col. 51, line 57, replace "3-3.1" with --3.3.1--.

Col. 51, line 66, replace "extacted" with --extracted--.

Col. 52, line 7, insert a comma after "$cm^{-1}$".

Col. 52, line 10, replace "4.08" with --4.08--.

Col. 52, line 18 replace "C 9.59" with --c 9.59--.

Col. 52, line 55, replace "aidehyde" with --aldehyde--.

Col. 52, line 57, insert a comma after "$cm^{-1}$".

Col. 52, line 61, replace "(3, s)" with --(3H, s)--.

Col. 53, line 1, replace "C 8.37 with --c 8.37--.

Col. 53, line 22, insert --42-- before "mmol"

Col. 53, line 33, insert a comma after "$cm^{-1}$".

Col. 53, line 45, replace "C 1.41" with --c 1.41--.

Col. 57, line 50, insert the word --added-- after "slowly".

Col. 57, line 52, replace "thee" with --the--.

Col. 58, line 25, replace "concnetrated," with --concentrated.--.

UNITED STATES PATENT AND TRADEMARK OFFICE
CERTIFICATE OF CORRECTION

PATENT NO. : 5,436,238

DATED : July 25, 1995

INVENTOR(S) : Yoshito Kishi et al.

It is certified that error appears in the above-identified patent and that said Letters Patent is hereby corrected as shown below:

Col. 58, line 29, replace "aidehyde" with --aldehyde--.

Col. 59, line 25, insert --493 $\mu$-- before "mol", second occurrence.

Col. 59, line 33, insert a space after "$R_f$".

Col. 60, line 16, delete "₃" in the formula, insert --₂--.

Col. 61, bottom formula, insert a bar between the right H and the carbon atom to its lower left.

Col. 61, line 46, replace "h 1" with --b,1,-- and replace "N'-his" with --N'-bis--.

Col. 62, line 15, replace "aidehyde" with --aldehyde--.

Col. 62, line 23, delete one of the two "of"s.

Col. 64, line 12, insert a space after "$R_f$".

Col. 64, line 27, replace "concentrted" with --concentrated--.

Col. 64, lines 29 and 32 insert a space after "$R_f$".

Col. 67, insert boldface bar between the $C_9$ atom and the oxygen atom below it.

Col. 69, line 25, replace "rection" with --reaction--.

UNITED STATES PATENT AND TRADEMARK OFFICE
CERTIFICATE OF CORRECTION

PATENT NO. : 5,436,238

DATED : July 25, 1995

INVENTOR(S) : Yoshito Kishi et al.

It is certified that error appears in the above-identified patent and that said Letters Patent is hereby corrected as shown below:

Col. 70, line 20, "Preparation of keto phosphonate" is a heading and should be in a single line.

Col. 71, line 2, replace "suspention" with --suspension--.

Col. 71, line 3, replace "Nail" with --NaH--.

Col. 71, line 3, replace "minerl" with --mineral--.

Col. 71, line 13, replace "rine" with --brine--.

Col. 71, line 18, replace "convertion" with --conversion--.

Col. 71, line 56, replace "yellwo" with --yellow--.

Col. 71, line 66, replace "suflate" with --sulfate--.

Col. 72, line 3, insert a comma after "$cm^{-1}$".

Col. 72, line 16 replace "C 2.00" with --c 2.00--.

Col. 72, line 61, replace "acooled" with --cooled--.

Col. 73, line 2, replace "get" with --gel--.

Col. 73, line 18 replace "0,285" with --0.285--.

Col. 73, line 25, replace "extrated" with --extracted--.

Col. 73, line 56 insert a comma after "$cm^{-1}$".

Col. 73, line 57 insert --3-- before "435".

UNITED STATES PATENT AND TRADEMARK OFFICE
CERTIFICATE OF CORRECTION

PATENT NO.   : 5,436,238

DATED        : July 25, 1995

INVENTOR(S)  : Yoshito Kishi et al.

It is certified that error appears in the above-identified patent and that said Letters Patent is hereby corrected as shown below:

Col. 74, line 19, replace "separared" with --separated--.

Col. 74, line 26, insert a comma after "cm$^{-1}$".

Col. 74, line 27, replace "2970," with --2970.--.

Col. 74, line 31, replace "(1H, Hz), 7.29" with --(1H, d, J=11.5 Hz), 6.87--.

Col. 74, line 54, replace "sufate" with --sulfate--.

Col. 74, lines 56 and 57, replace "hexames" with --hexanes--.

Col. 74, line 65, insert a comma after "cm$^{-1}$".

Col. 75, line 15, replace "TH" with --THF--.

Col. 75, line 25, replace "TsOH.H$_2$O" with --TsOH·H$_2$O--.

Col. 75, line 43, replace "DAMP" with --DMAP--.

Col. 75, line 58, insert a comma after "cm$^{-1}$".

Col. 75, line 65, insert a period after "m)".

Col. 75, line 68, replace "C" with --c--.

Col. 76, line 22, replace "BF$_3$.OEt$_2$" with --BF$_3$·OEt$_2$--.

Col. 76, line 41, delete the comma after "1514"; insert a comma after "cm$^{-1}$".

UNITED STATES PATENT AND TRADEMARK OFFICE
CERTIFICATE OF CORRECTION

PATENT NO. : 5,436,238

DATED : July 25, 1995

INVENTOR(S) : Yoshito Kishi et al.

It is certified that error appears in the above-identified patent and that said Letters Patent is hereby corrected as shown below:

Col. 76, line 41, insert a period after "3502".

Col. 77, line 57, replace "compund" with --compound--.

Col. 77, line 65, insert a comma after "$cm^{-1}$".

Col. 77, line 68, replace "S" with --s--.

Col. 78, line 55, replace "filtrae" with --filtrate--.

Col. 79, line 50, insert a comma after "$cm^{-1}$".

Col. 79, line 53, delete "(3H,", first occurrence after "0.26".

Col. 79, line 54, insert --=6.8-- after "J".

Col. 79, line 56, replace "M" with --m--.

Col. 79, line 57, replace "2.20 H" with --2.20 (1 H--.

Col. 79, line 57, replace "1 10.2" with --1 H, dd, J=10.2--.

Col. 79, line 58, delete dash and insert "=" after "J".

Col. 80, line 53, insert "002" after "nitrile".

Col. 80, line 56, replace "0,252" with --0.252--.

Col. 81, line 3, insert --003-- after "aldehyde".

UNITED STATES PATENT AND TRADEMARK OFFICE
CERTIFICATE OF CORRECTION

PATENT NO. : 5,436,238

DATED : July 25, 1995

INVENTOR(S) : Yoshito Kishi et al.

It is certified that error appears in the above-identified patent and that said Letters Patent is hereby corrected as shown below:

Col. 81, line 7, insert a comma before "30 mg".

Col. 81, line 28, replace "C 0.41" with --c 0.41--.

Col. 81, line 30, replace "henzylether" with --benzylether--.

Col. 81, line 34, replace "henzyl" with --benzyl--.

Col. 81, line 48, replace "trifluride" with --trifluoride--.

Col. 82, line 61, replace "$CDCl_{31}$" with --$CDCl_3$--.

Col. 83, line 3, replace "C 1.95" with --c 1.95--.

Col. 83, line 56, replace "distallation" with --distillation--.

Col. 84, line 26, replace "$Na_2BO_4$" with --$Na_2SO_4$--.

Col. 84, line 30, replace "mixted" with --mixed--.

Col. 84, line 30, replace "55%" with --85%--.

Col. 85, line 36, replace "C" with --c--.

Col. 85, line 38, "Step d" should be on a separate line.

Col. 86, line 5, replace "ethyle" with --ethyl--.

Col. 86, line 39, replace "0,235" with --0.235--.

UNITED STATES PATENT AND TRADEMARK OFFICE
CERTIFICATE OF CORRECTION

PATENT NO.  : 5,436,238

DATED       : July 25, 1995

INVENTOR(S) : Yoshito Kishi et al.

It is certified that error appears in the above-identified patent and that said Letters Patent is hereby corrected as shown below:

Col. 86, line 54, replace "aidehyde" with --aldehyde--.

Col. 87, lower left formula, replace " [formula] " with -- [formula] --.

Col. 87, line 54, replace "2.0 mole" with --2.0 mmole--.

Col. 87, line 55, replace "lithum" with --lithium--.

Col. 87, line 61, replace "samll" with --small--.

Col. 88, top right formula, replace " [formula] " with -- [formula] --.

Col. 88, line 28, replace "suspention" with --suspension--.

Col. 88, line 33, replace "Compound i" with --Compound 1--.

Col. 88, line 45, replace "B I" with --B 1--.

Col. 88, line 58, replace "synethetic" with --synthetic--.

Col. 88, line 62, replace "lekemia" with --leukemia--.

Col. 89, line 3, replace "synethetic" with --synthetic--.

UNITED STATES PATENT AND TRADEMARK OFFICE
CERTIFICATE OF CORRECTION

PATENT NO. : 5,436,238
DATED : July 25, 1995
INVENTOR(S) : Yoshito Kishi et al.

It is certified that error appears in the above-identified patent and that said Letters Patent is hereby corrected as shown below:

Col. 89, lines 27 and 28, replace "B I" with --B 1--.

Col. 89, line 62, replace "Counting" with --counting--.

Col. 90, line 39, replace "$R_3$-H(OH)" with --$R_3$-CH(OH)--.

Signed and Sealed this

Twenty-eighth Day of April, 1998

Attest:

BRUCE LEHMAN

Attesting Officer

Commissioner of Patents and Trademarks